(12) United States Patent
Gilbertie et al.

(10) Patent No.: US 11,951,134 B2
(45) Date of Patent: Apr. 9, 2024

(54) CATIONIC PLATELET LYSATE COMPOSITIONS AND RELATED METHODS

(71) Applicants: North Carolina State University, Raleigh, NC (US); The Trustees of the University of Pennsylvania, Philadelphia, PA (US)

(72) Inventors: Jessica M. Gilbertie, Cary, NC (US); Lauren V. Schnabel, Holly Springs, NC (US); Thomas P. Schaer, Landenberg, PA (US)

(73) Assignees: North Carolina State University, Raleigh, NC (US); The Trustees of the University of Pennsylvania, Philadelphia, PA (US)

( * ) Notice: Subject to any disclaimer, the term of this patent is extended or adjusted under 35 U.S.C. 154(b) by 62 days.

(21) Appl. No.: 17/039,418

(22) Filed: Sep. 30, 2020

(65) Prior Publication Data
US 2021/0128626 A1 May 6, 2021

Related U.S. Application Data

(60) Provisional application No. 62/908,318, filed on Sep. 30, 2019.

(51) Int. Cl.
| *A61K 35/19* | (2015.01) |
| *A61K 35/15* | (2015.01) |
| *A61K 35/18* | (2015.01) |
| *A61P 17/02* | (2006.01) |

(52) U.S. Cl.
CPC .............. *A61K 35/19* (2013.01); *A61K 35/15* (2013.01); *A61K 35/18* (2013.01); *A61P 17/02* (2018.01)

(58) Field of Classification Search
CPC ........ A61K 35/19; A61K 35/15; A61K 35/18; A61K 31/7036; A61K 35/16; A61K 35/17; A61K 38/02; A61P 17/02; A61P 19/02; A61P 29/00; A61P 31/04
See application file for complete search history.

(56) References Cited

U.S. PATENT DOCUMENTS

| 7,638,149 | B2 | 12/2009 | Msika et al. |
| 8,168,230 | B2 | 5/2012 | Evangelista |
| 10,925,901 | B2 | 2/2021 | Dietz et al. |
| 11,197,893 | B2* | 12/2021 | Ceballos ................. A61K 35/19 |
| 11,304,981 | B2 | 4/2022 | Houze et al. |
| 2002/0192632 | A1* | 12/2002 | Hei ........................ A61K 35/19 435/2 |
| 2008/0279745 | A1 | 11/2008 | Dorn et al. |
| 2009/0023211 | A1* | 1/2009 | Persson ................. C12N 5/0018 426/647 |
| 2009/0240042 | A1 | 9/2009 | Dorn et al. |
| 2017/0151287 | A1* | 6/2017 | von Maltzahn ........ A61K 35/19 |
| 2018/0236007 | A1 | 8/2018 | Shin et al. |

FOREIGN PATENT DOCUMENTS

| CN | 102465148 A | 5/2012 |
| CN | 103784474 B | 5/2015 |
| CN | 106191127 B | 1/2020 |
| CN | 106754668 B | 8/2020 |
| KR | 10-2015-0029280 | 3/2015 |
| WO | WO-89/10398 A1 | 11/1989 |
| WO | WO 93/08812 * | 5/1993 |
| WO | WO-2006/023911 A2 | 3/2006 |
| WO | WO-2009/114785 A2 | 9/2009 |
| WO | WO-2017/211906 A1 | 12/2017 |

OTHER PUBLICATIONS

Farghali H. et al. Antimicrobial Action of Autologous PRP on MRSA Infected Skin Wounds in Dogs. Nature Research vol. 9 12722-37, Sep. 2019. (Year: 2019).*
Zhang, W. et al. PRP for the Treatment of Tissue Infection. Tissue Engineering B 25(3)225-236, 2019. (Year: 2019).*
Aigner et al., (2010) "Histopathology atlas of animal model systems—overview of guiding principles." Osteoarthr. Cartil., vol. 18, pp. S2-S6.
Al Mohajer et al., (2014) "The expanding horizon of prosthetic joint infections." J. Appl. Biomater. Funct. Mater., vol. 12, pp. 1-12.
Al-Ajlouni et al., (2014) "Safety and Efficacy of Autologous Intra-articular Platelet Lysates in Early and Intermediate Knee Osteoarthrosis in Humans." Clin. J. Sports Med., pp. 1-5.
Altaie et al.,(2018) "Platelet lysate enhances synovial fluid multipotential stromal cells functions: Implications for therapeutic use." Cytotherapy, vol. 20, pp. 1-25.

(Continued)

*Primary Examiner* — Aaron J Kosar
(74) *Attorney, Agent, or Firm* — Jenkins, Taylor, & Hunt P.A.

(57) ABSTRACT

An acellular, anion-depleted platelet-derived peptide-rich composition comprising proteins, polypeptides and peptides <10 kDa in size, wherein the composition has anti-microbial and/or anti-inflammatory activity is disclosed. The composition can be substantially free of non-active and immunogenic factors. The composition can have a platelet-to-bacteria ratio $\geq 1000:1$. The composition can comprise plasma at a range of $\geq 10\%$ to $\leq 50\%$ plasma, optionally about 10% plasma. Methods of using the composition are also disclosed. Also disclosed is a method for preparing an acellular platelet-derived peptide-rich composition having anti-microbial and/or anti-inflammatory activity, the method comprising: providing a starting material comprising platelet-rich plasma processed to contain $\geq 1,000,000$ platelet/$\mu L$, $\leq 100$ leukocytes/$\mu L$ and $\leq 10$ erythrocyte/$\mu L$ in plasma; lysing and/or activating the starting material; contacting the starting material with an ion exchange matrix and/or a size exchange matrix; and isolating the acellular platelet-derived peptide-rich composition.

11 Claims, 33 Drawing Sheets

(32 of 33 Drawing Sheet(s) Filed in Color)

(56) References Cited

OTHER PUBLICATIONS

Altaie, et al., (2016) "Use of platelet lysate for bone regeneration—are we ready for clinical translation?" World J. Stem Cells, vol. 8, pp. 47-55.
Aprianto et al., (2018) "High-resolution analysis of the pneumococcal transcriptome under a wide range of infection-relevant conditions." Nucleic Acids Res., vol. 46, pp. 9990-10006.
Arciola et al.,(2015) "Polysaccharide intercellular adhesin in biofilm: structural and regulate aspects." Front. Cell. Infect. Microbiol., vol. 5, Article No. 7; pp. 1-10.
Astori et al., (2016) "Platelet lysate as a substitute for animal serum for the ex-vivo expansion of mesenchymal stem/stromal cells: Present and future." Stem Cell Res. Ther., vol. 7, pp. 1-8.
Bankhead et al., (2017) "QuPath: Open source software for digital pathology image analysis," Sci. Rep., vol. 7, Article No. 16878.
Barton et al.,(2007) "Demonstration of a novel technique to quantitatively assess inflammatory mediators and cells in rat knee joints." J. Inflamm., vol. 4, Article 13 pp. 1-8.
Bay et al., (2018) "Bacterial Aggregates Establish at the Edges of Acute Epidermal Wounds." Adv. Would Care, bol. 7, pp. 105-113.
Beenken et al., (2004) "Global gene expression in *Staphylococcus aureus* biofilms." J. Bacteriol., vol. 186, pp. 4665-4684.
Bernthal et al., (2011) "Protective role of IL-1beta against post-arthroplasty *Staphylococcus aureus* infection." J. Orhtop. Res., vol. 29, pp. 1621-1626.
Bhattacharya et al., (2018) "*Staphylococcus aureus* biofilms release leukocidins to elicit extracellular trap formation and evade neutrophil-mediated killing." Proc. Natl. Acad. Sci., vol. 115, pp. 7416-7421.
Bielecki et al., (2007) "Antibacterial effect of autologous platelet gel enriched with growth factors and other active substances: An in Vitro Study." J. Bone Joint Surg., vol. 89-B, pp. 417-420.
Bjarnsholt et al., (2013) "The in vivo biofilm." Trends Microbiol., vol. 21, pp. 466-474.
Boff et al., (2018) "Neutrophils: Beneficial and Harmful Cell in Septic Arthritis." Int. J. Mol. Sci., vol. 19 pp. 1-28.
Boles et al., (2008) "agr-mediated dispersal of *Staphylococcus aureus* biofilms." PLoS Pathog., vol. 4, Article ID e1000052; pp. 1-13.
Bolt et al., (2008) "Effects of triamcinolone acetonide, sodium hyaluronate, amikacin sulfate, and mepivacaine hydrochloride, alone and in combination, on morphology and matrix composition of lipopolysaccharide-challenged and unchallenged equine articular cartilage explants." Am. J. Vet. Res., vol. 69, pp. 861-867.
Boswell et al., (2014) "Increasing Platelet Concentrations in Leukocyte-Reduced Platelet-Rich Plasma Decrease Collagen Gene Synthesis in Tendons." Am. J. Sports Med., vol. 42, pp. 42-49.
Boswell et al., (2012) "Platelet-rich plasma: A milieu of bioactive factors." Arthrosc. J. Arthrosc. Relat. Surg., vol. 28, pp. 429-439.
Boyle et al., (2018) "General Assembly, Treatment, Antimicrobials: Proceedings of International Consensus on Orthopedic Infections." J. Arthroplasty, vol. 34, pp. 1-13.
Brackman et al.,(2015) "Quorum sensing inhibitors as anti-biofilm agents." Curr. Pharm. Des., vol. 21, pp. 1-7.
Branzk et al.,(2014) "Neutrophils sense microbe size and selectively release neutrophil extracellular traps in response to large pathogens." Nat. Immunol., vol. 15, pp. 1-23.
Burmolle et al., (2010) "Biofilms in chronic infections—A matter of opportunity—Monospecies biofilms in multispecies infections." FEMS Immunol. Med. Microbiol., vol. 59, pp. 324-336.
Burnouf et al., (2013) "Antimicrobial activity of platelet (PLT)-poor plasma, PLT-rich plasma, PLT gel, and solvent/detergent-treated PLT lysate biomaterials against wound bacteria." Transfusion, vol. 53, pp. 138-146.
Burnouf et al., (2016) "Human platelet lysate: Replacing fetal bovine serum as a gold standard for human cell propagation?" Biomaterials, vol. 76, pp. 371-387.
Byron et al., (2008) "Effects of clinically relevant concentrations of glucosamine on equine chondrocytes and synoviocytes in vitro." Am. J. Vet. Res., vol. 69, pp. 1129-1134.
Caceres et al., (2014) "Enhanced in vitro formation and antibiotic resistance of nonattached pseudomonas aeruginosa aggregates through incorporation of neutrophil products." Antimicrob. Agetns Chemother., vol. 58, pp. 6854-6860.
Ceri et al., (1999) "The Calgary Biofilm Device: new technology for rapid determination of antibiotic susceptibilities of bacterial biofilms." J. Clin. Microbiol., vol. 37, pp. 1771-1776.
Chou et al., (2017) "Current methods to manufacture human platelet lysates for cell therapy and tissue engineering: possible trends in product safety and standardization." ISBT Sci. Ser., pp. 168-175.
Cieslik-Bielecka et al.,(2012) "Microbicidal properties of Leukocyte- and Platelet-Rich Plasma/Fibrin (L-PRP/L-PRF): new perspectives." J. Biol. Regul. Homeost. Agents, vol. 26, pp. 43S-52S.
Gilbertie et al., "Oral reserpine administration in horses results in low plasma concentrations that alter platelet biology." Equine Vet J., Article No. 13048 (2018).
Gilbertie et al., "Pooled Platelet-Rich Plasma Lysate Therapy Increases Synoviocyte Proliferation and Hyaluronic Acid Production While Protecting Chondrocytes From Synoviocyte-Derived Inflammatory Mediators." Front. Vet. Sci., vol. 5, Article No. 150 (2018).
Gilbertie et al., "Platelet-rich plasma lysate displays antibiofilm properties and restores antimicrobial activity against synovial fluid biofilm in vitro," J. Orthop. Res., jor.24584 (Jan. 14, 2020).
Gilbertie et al., "Equine or porcine synovial fluid as a novel ex vivo model for the study of bacterial free-floating biofilms that form in human joint infections," PLoS One, vol. 14, Article ID e0221012 (Aug. 15, 2019).
Kidd et al., "Use of matrix metalloproteinases 2 and 9 and white blood cell counts in monitoring the treatment and predicting the survival of horses with septic arthritis." Vet. Rev., vol. 161, pp. 329-334, (2007).
Schnabel et al., "Platelet rich plasma (PRP) enhances anabolic gene expression patterns in flexor digitorum superficialis tendons." J. Orthop. Res., vol. 25, pp. 230-240 (2007).
Sorensen et al., "Human cathelicidin, hCAP-18, is processed to the antimicrobial peptide LL-37 by extracellular cleavage with proteinase 3." Blood, vol. 97, pp. 3951-3959 (2001).
Tang et al., "Antimicrobial peptides from human platelets." Infect. Immun., vol. 70, pp. 6524-6533 (2002).
Trumble et al., "Synovial fluid gelatinase concentrations and matrix metalloproteinase and cytokine expression in naturally occurring join disease in horses." Am. J. Vet. Res., vol. 62, pp. 1467-1477 (2001).
Zhang et al., "Antimicrobial peptides." Curr. Biol., vol. 26, pp. R14-R19 (2016).
Gilbertie, "Bacterial Behavior in Synovial Fluid and Development of a Novel Therapeutic to Combat Infectious Arthritis," North Carolina State University, thesis, 170 pages, Aug. 10, 2020.
Cox et al., "Platelets and the innate immune system: Mechanisms of bacterial-induced platelet activation." J. Thromb. Haemost., vol. 9, pp. 1097-1107 (2011).
Drago et al., "Antimicrobial activity of pure platelet-rich plasma against microorganisms isolated from oral cavity." BMC Microbiol., vol. 13, Article No. 47, 5 pages (2013).
Drago et al., "Plasma components and platelet activation are essential for the antimicrobial properties of autologous platelet-rich plasma: An in vitro study." PLoS One, vol. 9, Article ID e107813, 5 pages (2014).
Garraud et al., "Bench-to-bedside review: Platelets and active immune functions—new clues for immunopathology?" Crit. Care, vol. 17, Article No. 236, 12 pages (2013).
Giraldo et al., "Effects of the breed, sex and age on cellular content and growth factor release from equine pure-platelet rich plasma and pure-platelet rich gel." BMC Vet. Res., vol. 9, Article No. 29, 10 pages (2013).
Intravia et al., "In vitro evaluation of the anti-bacterial effect of two preparations of platelet rich plasma compared with cefazolin and whole blood." Musc. Lig. Tendons J., vol. 4, pp. 79-84 (2014).
Klatte-Schulz et al., "Comparative analysis of different platelet lysates and platelet rich preparations to stimulate tendon cell biology: An in vitro study." Int. J. Mol. Sci., vol. 19, Article No. 212, 18 pages (2018).

(56) References Cited

OTHER PUBLICATIONS

Kraemer et al., "Novel anti-bacterial activities of beta-defensin 1 in human platelets: Suppression of pathogen growth and signaling of neutrophil extracellular trap formation." PLoS Pathog., vol. 7, Article ID e1002355, 9 pages (2011).

Li et al., "Efficacy of leukocyte- and platelet-rich plasma gel (L-PRP gel) in treating osteomyelitis in a rabbit model." J. Orthop. Res., vol. 31, pp. 949-956 (2013).

Li et al., "Unique antimicrobial effects of platelet-rich plasma and its efficacy as a prophylaxis to prevent implant-associated spinal infection." Author Manuscript, Published in final edited form as: Adv. Healthc. Mater., vol. 2, pp. 1277-1284 (2013).

Mercier et al., "Beneficial Influence of Platelets on Antibiotic Efficacy in an In Vitro Model of *Staphylococcus aureus*-Induced Endocarditis." Antimicrob. Agents Chemother., vol. 48, pp. 2551-2557 (2004).

Moojen et al., "Antimicrobial activity of platelet-leukocyte gel against *staphylococcus aureus*." J. Orthop. Res., vol. 26, pp. 404-410 (2008).

O'Brien et al., "Multiple mechanisms for the activation of human platelet aggregation by *Staphylococcus aureus* : Roles for the clumbing factors ClfA and ClfB, the serine-aspartate repeat protein SdrE and protein A." Mol. Microbiol., vol. 44, pp. 1033-1044 (2002).

Rinnovati et al., "The influence of environmental variables on platelet concentration in horse platelet-rich plasma." Acta Vet. Scand., vol. 58, Article No. 45, 5 pages (2016).

Rozalski et al., "Antimicrobial/anti-biofilm activity of expired blood platelets and their released products." Postepy. Hig. Med. Dosw., vol. 67, pp. 321-325 (2013).

Sondergaard et al., "Senescence and quiescence in adipose-derived stromal cells: Effects of human platelet lysate, fetal bovine serum and hyposia." Cyrotherapy, vol. 19, pp. 95-106 (2017).

Sumner et al., Platelet lysate obtained via plateletpheresis performed in standing and awake equine donors. Transfusion, vol. 57, pp. 1755-1762 (2017).

Trier et al., "Platelet Antistaphylococcal Responses Occur through P2X1 and P2Y12 Receptor-Induced Activation and Kinocidin Release." Infect. Immun., vol. 76, pp. 5706-5713 (2008).

Trzeciak-Ryczek et al., "Platelets—An important element of the immune system." Pol. J. Vet. Sci., vol. 16, pp. 407-413 (2013).

Tyrnenopoulou et al., "Evaluation of intra-articular injection of autologous platelet lysate (PL) in horses with osteoarthritis of the distal interphalangeal joint." Vet. Q., vol. 36, pp. 56-62 (2016).

Xiong et al., "Men and Women Differ in the Biochemical Composition of Platelet-Rich Plasma." Am. J. Sports Med., vol. 46, pp. 409-419 (2018).

Xu et al., "IL-18 induces the differentiation of Th1 or Th2 cells depending upon cytokine milieu and genetic background." Eur. J. Immunol., vol. 30, pp. 3147-3156 (2000).

Xu et al., "Plasma fibrinogen may predict persistent infection before reimplantation in two-stage exchange arthroplasty for periprosthetic hip infection." J. Orthop. Surg. Res., vol. 14, Article No. 133, 7 pages (2019).

Yeaman et al., "*Staphylococcus aureus* susceptibility to thrombin-induced platelet microbicidal protein is independent of platelet adherence and aggregation in vitro." Infect. Immun., vol. 60, pp. 2368-2374 (1992).

Yeaman et al., "Thrombin-induced rabbit platelet microbicidal protein is fungicidal in vitro." Antimicrob. Agents Chemother., vol. 37, pp. 546-553 (1993).

Yeaman et al., "Purification and in vitro activities of rabbit platelet microbicidal proteins." Infect. Immun., vol. 65, pp. 1023-1031 (1997).

Zhou et al., "Platelet aggregation testing in platelet-rich plasma: description of procedures with the aim to develop standards in the field." Am. J. Clin. Pathol., vol. 123, pp. 172-183 (2005).

Aktan et al.,(2013) "Equine platelets inhibit *E. coli* growth and can be activated by bacterial lipopolysaccharide and lipteichoic acid although superoxide anion production does not occur and platelet activation is not associated with enhanced production by neutrophils." Vet. Immunol. Immunopathol., vol. 152, pp. 209-217.

Cetinkaya et al.,(2018) "The efficacy of platelet-rich plasma gel in MRSA-related surgical wound infection treatment: an experimental study in an animal model." Eur. J. Trauma Emerg. Surg., vol. 44, pp. 859-867.

Del Bue et al., "Platelet lysate promotes in vitro proliferation of equine mesenchymal stem cells and tenocytes." Vet. Res. Commun., vol. 31 Supply. 1, pp. 289-292 (2007).

Hildner et al., "Human platelet lysate successfully promotes proliferation and subsequent chondrogenic differentiation of adipose-derived stem cells: a comparison with articular chondrocytes." J. Tissue Eng. Regen. Med. (2013).

Mariani et al., "Platelet-rich plasma affects bacterial growth in vitro." Cytotherapy, vol. 16, pp. 1294-1304 (2014).

Moreira et al., "The effect of platelet lysate supplementation of a dextran-based hydrogel on cartilage formation." Biomaterials, vol. 33, pp. 3651-3661 (2012).

Naskou et al., "Innate immune responses of equine monocytes cultured in equine platelet lysate." Vet. Immunol. Immunopathol., vol. 195, pp. 65-71 (2018).

Nguyen et al., "Platelet lysate activates quiescent cell proliferation and reprogramming in human articular cartilage: Involvement of hypoxia inducible factor 1." J. Tissue Eng. Regen. Med., pp. 1-13 (2017).

Pereira et al., "Dual Effect of Platelet Lysate on Human Articular Cartilage: A Maintenance of Chondrogenic Potential and a Transient Proinflammatory Activity Followed by an Inflammation Resolution." Tissue Eng, Part A, vol. 19, pp. 1476-1488 (2013).

Santo et al., "Natural assembly of platelet lysate-loaded nanocarriers into enriched 3D hydrogels for cartilage regeneration." Acta Biomater., vol. 19, pp. 56-65 (2015).

Sundman et al., "The Anti-inflammatory and Matrix Restorative Mechanisms of Platelet-Rich Plasma in Osteoarthritis." Am. J. Sports Med., vol. 42, pp. 35-41 (2014).

Tohidnezhad et al., "Platelets display potent antimicrobial activity and release human beta-defensin 2." Platelets, vol. 23, pp. 217-223 (2012).

* cited by examiner

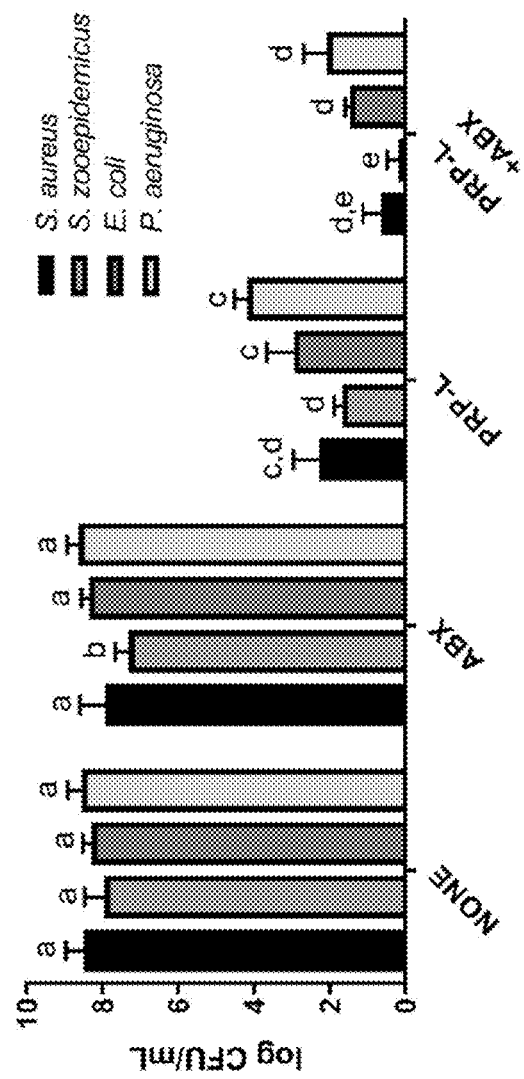
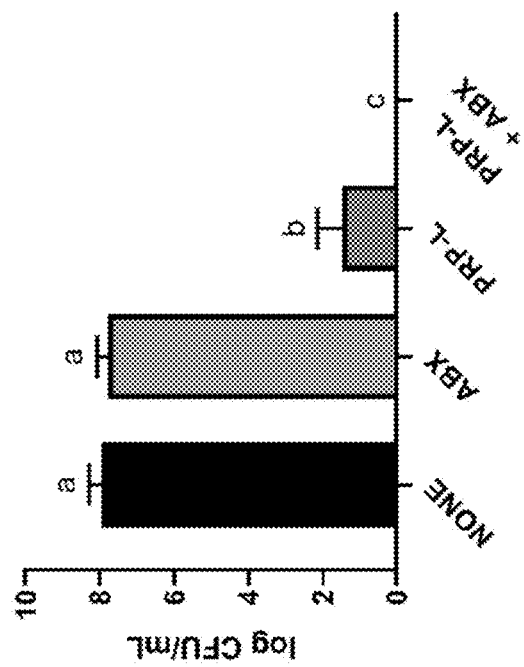
FIG. 3B
FIG. 3A

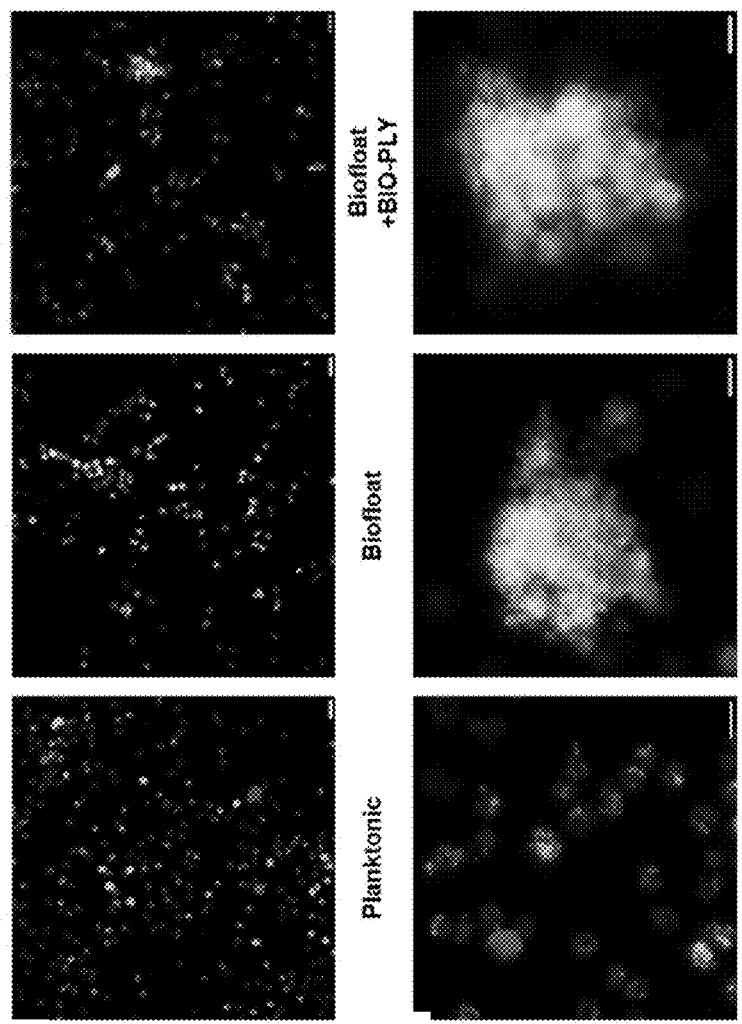
FIG. 8B
FIG. 8C
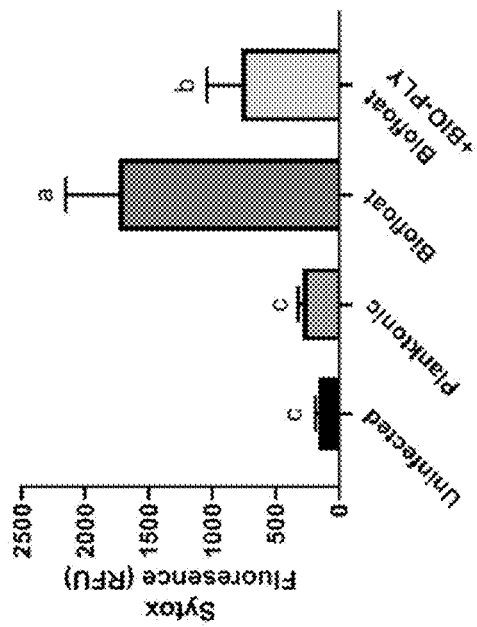
FIG. 8A

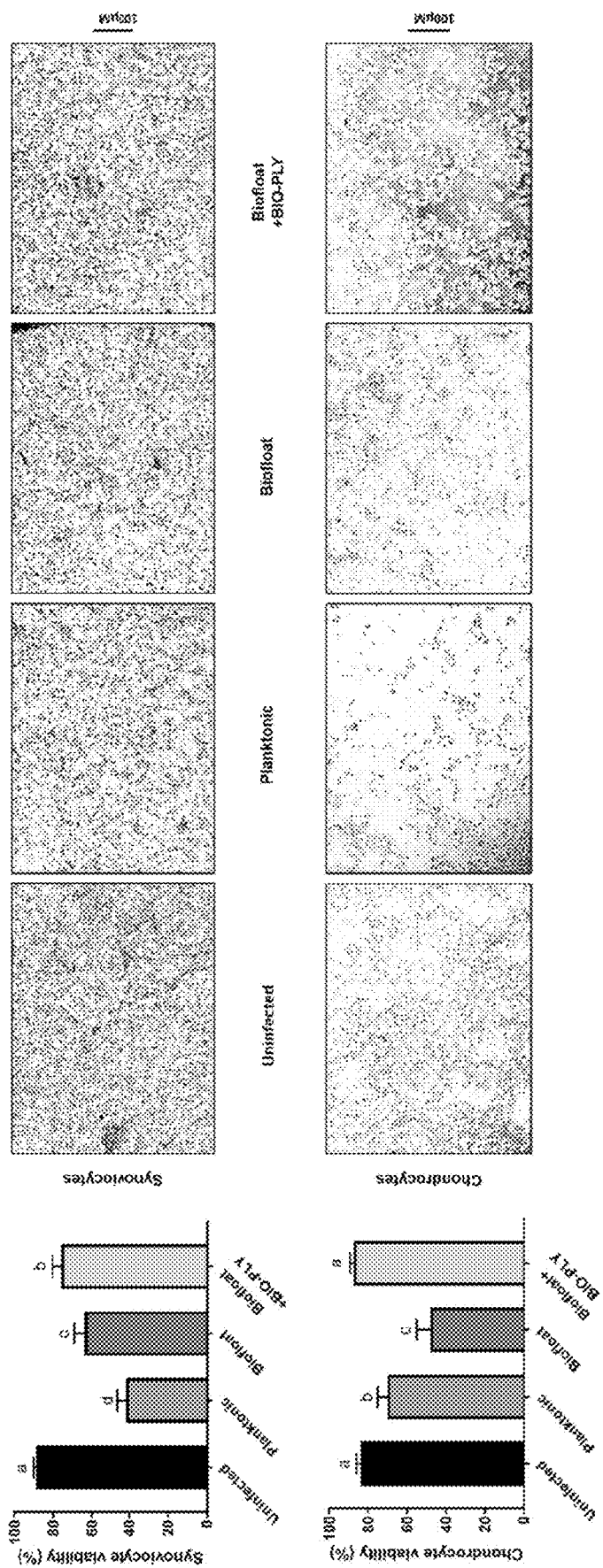

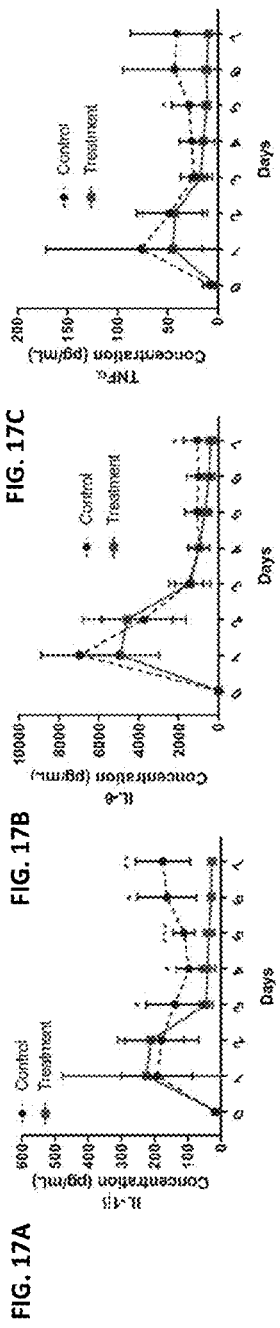
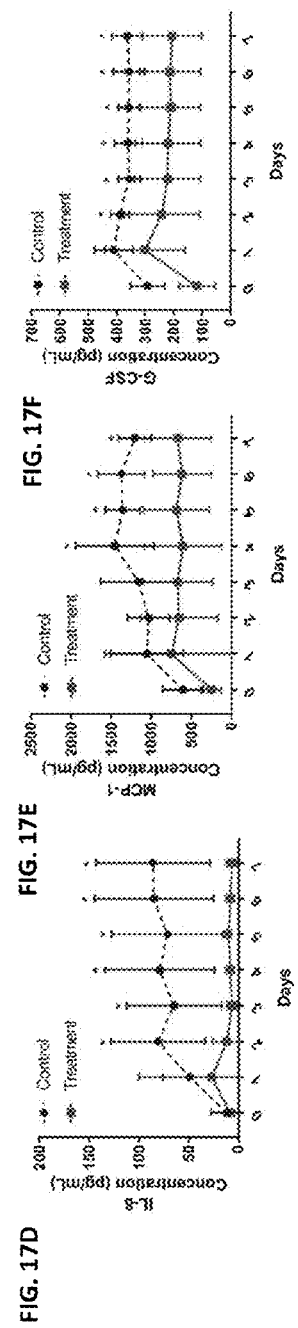
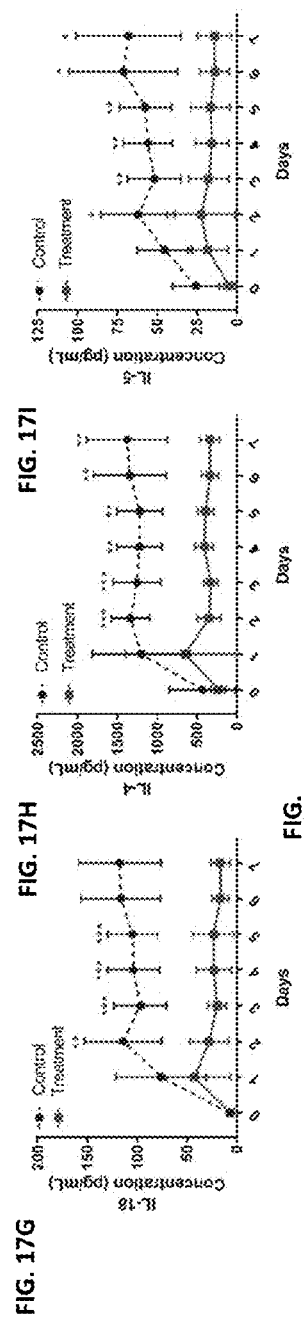
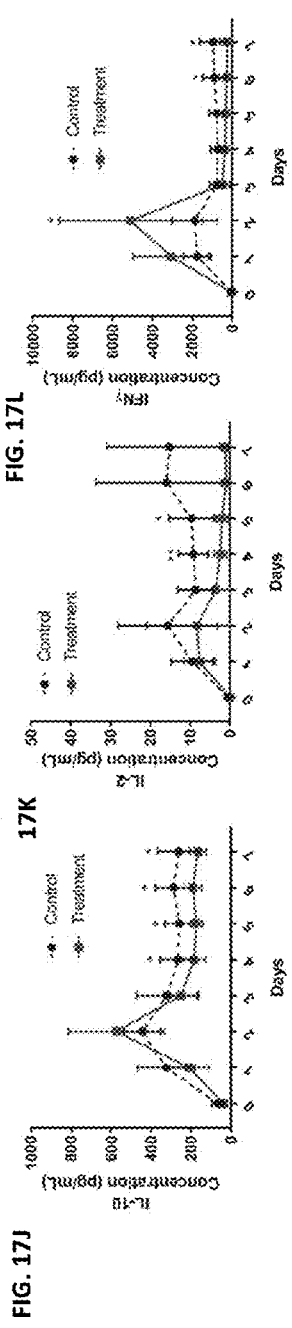
FIG. 17A FIG. 17B FIG. 17C
FIG. 17D FIG. 17E FIG. 17F
FIG. 17G FIG. 17H FIG. 17I
FIG. 17J FIG. 17K FIG. 17L

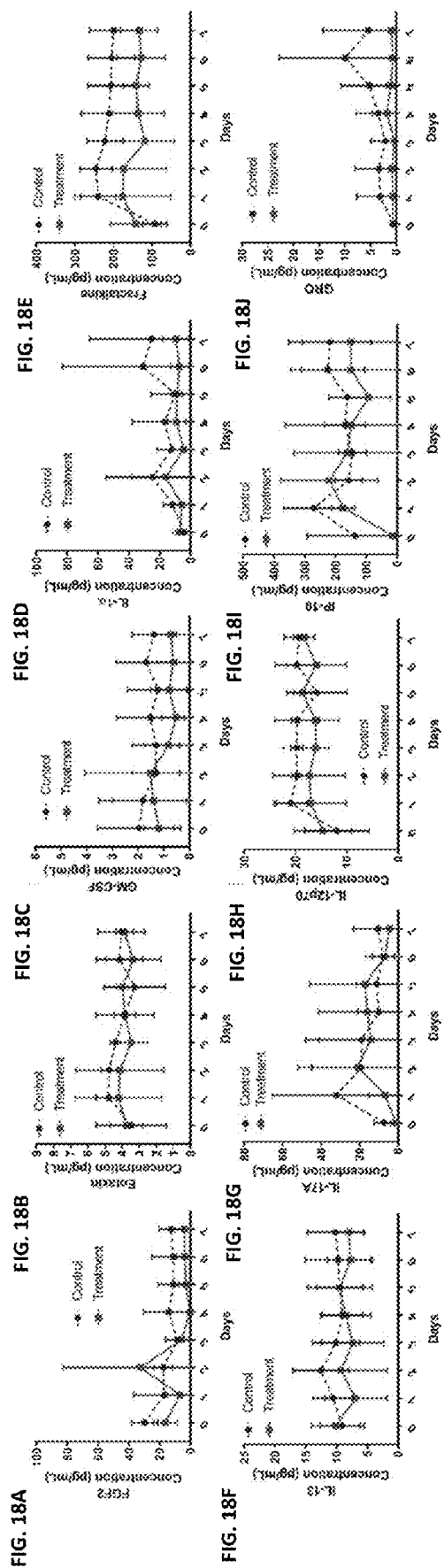

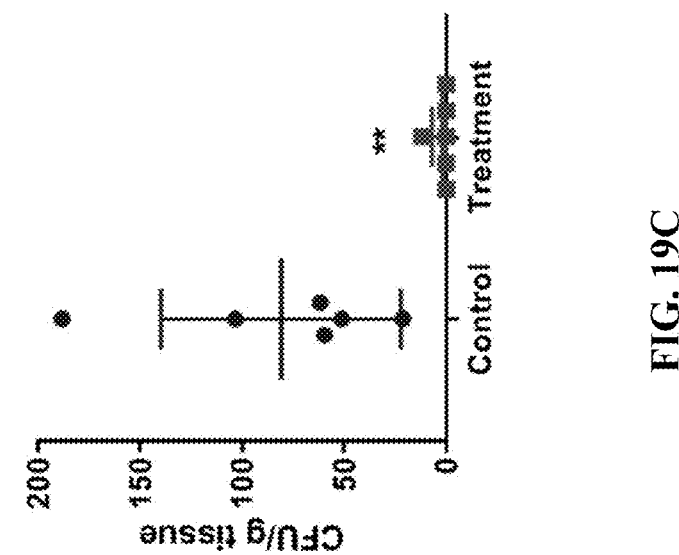
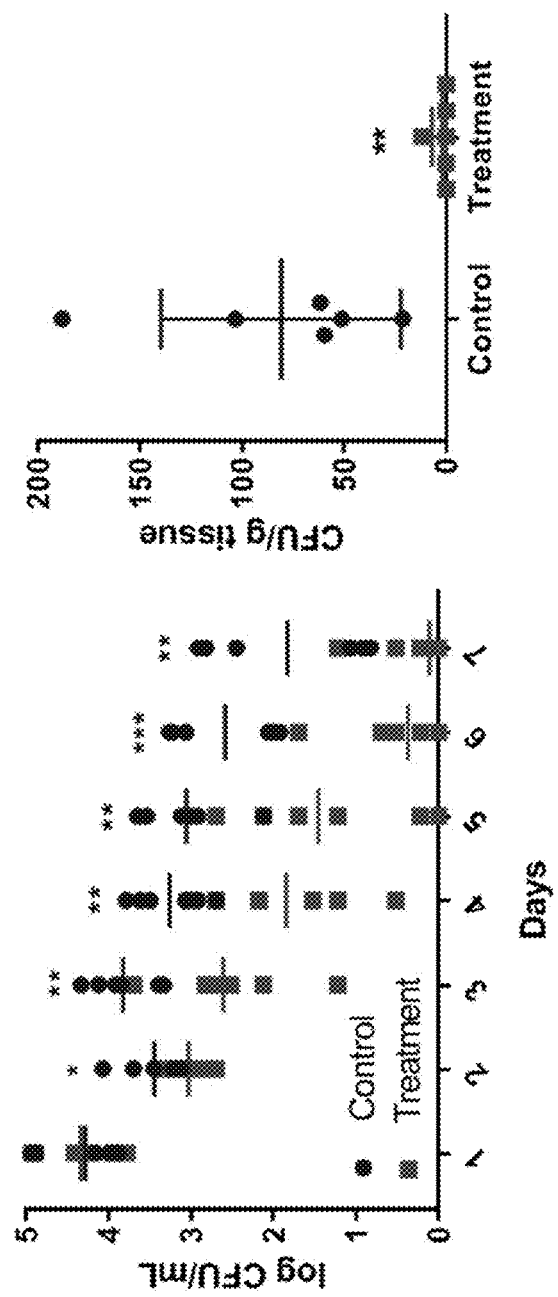
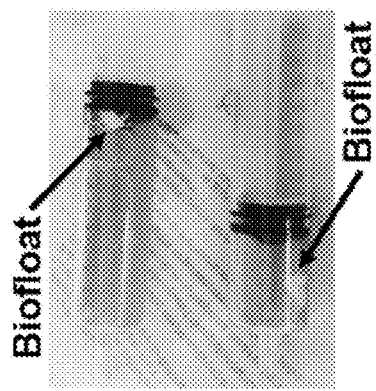
FIG. 19C
FIG. 19B
FIG. 19A

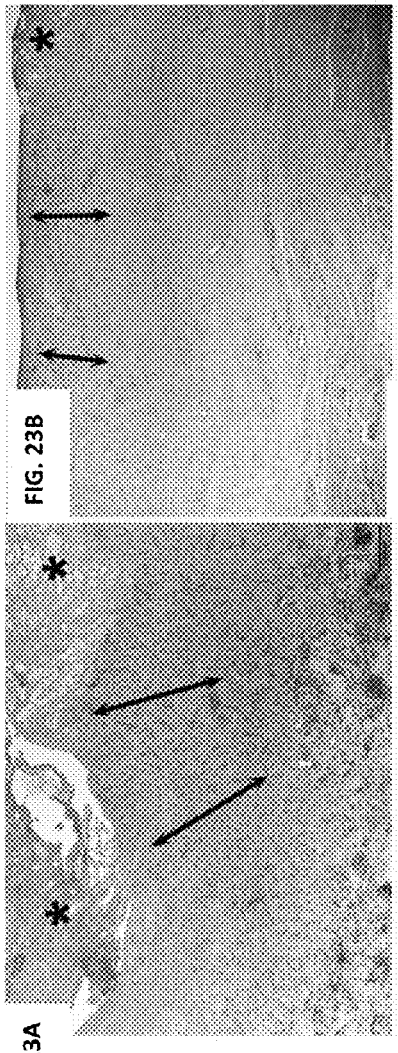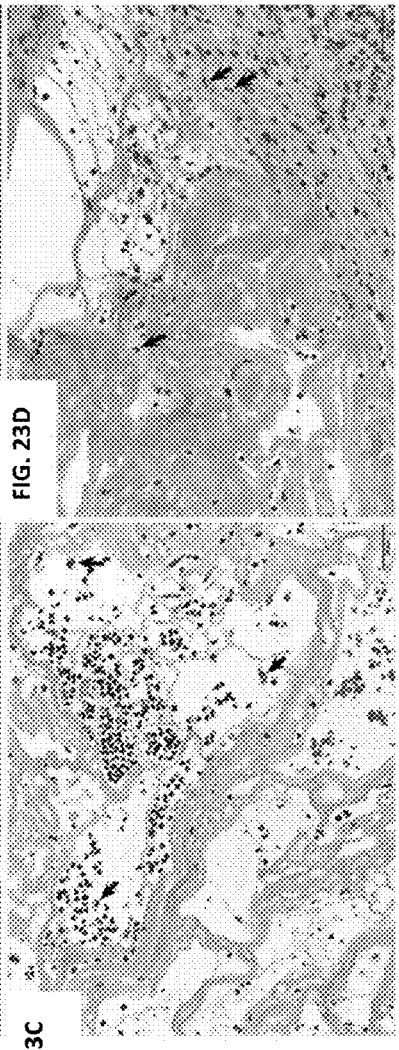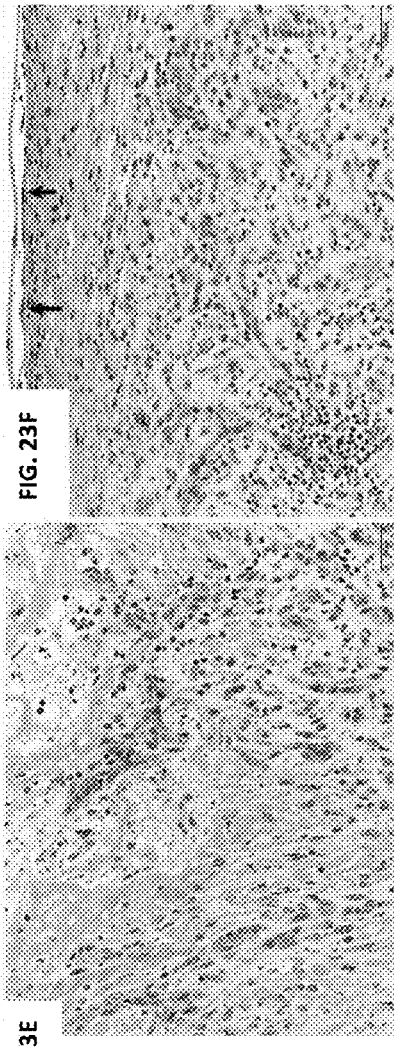

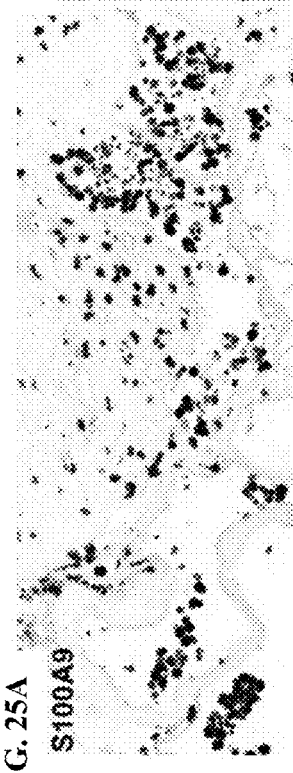
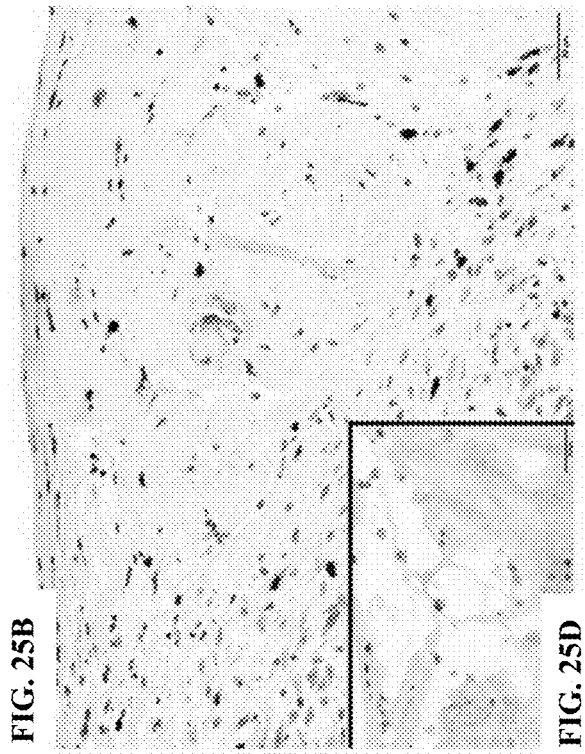
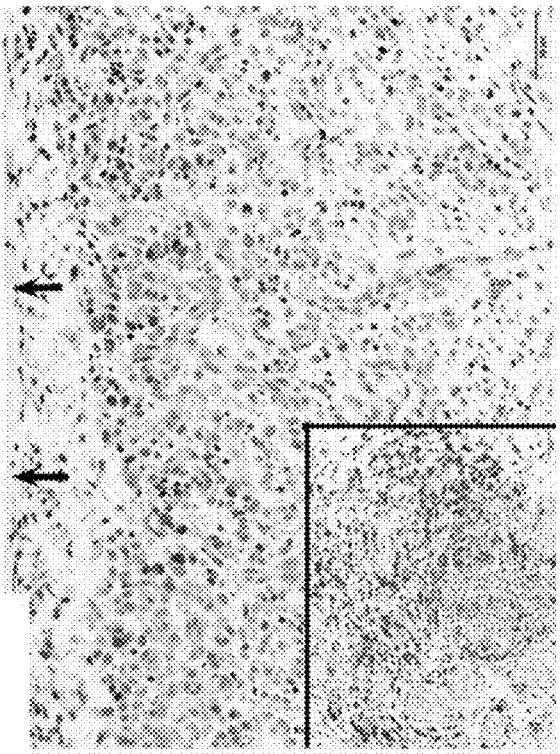
FIG. 25A S100A9
FIG. 25B
FIG. 25C CD20 Superficial / Deep
FIG. 25D
CD204

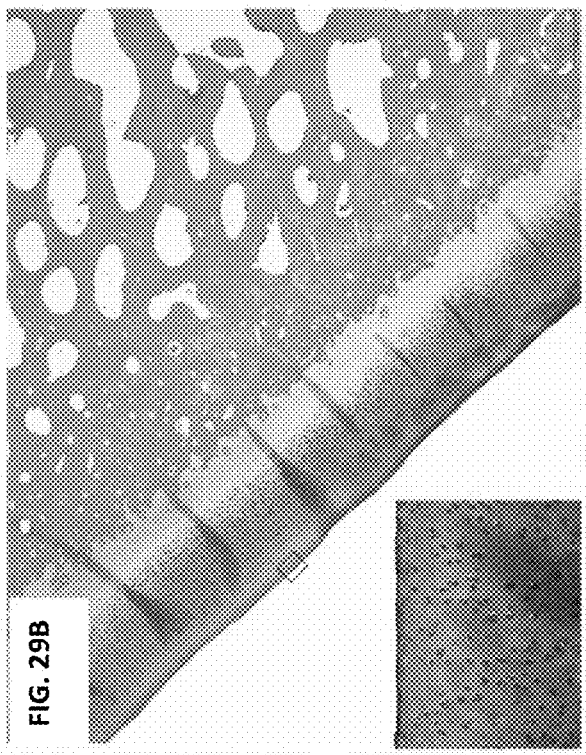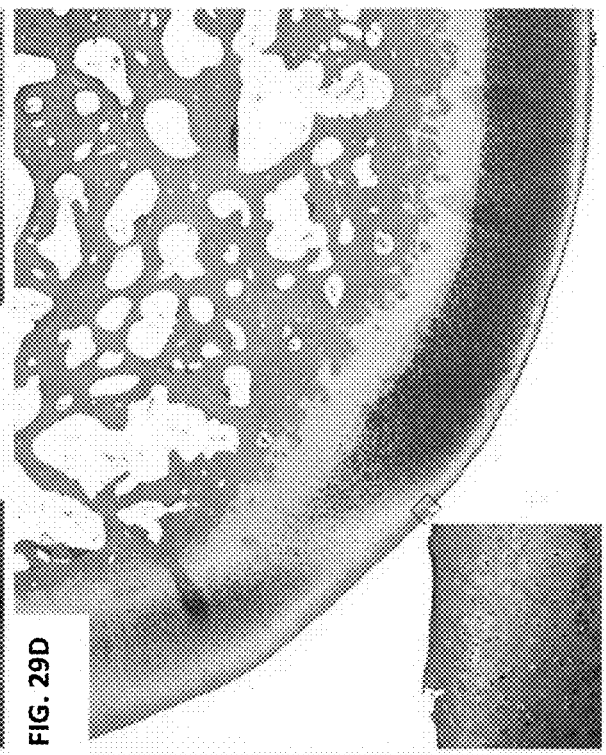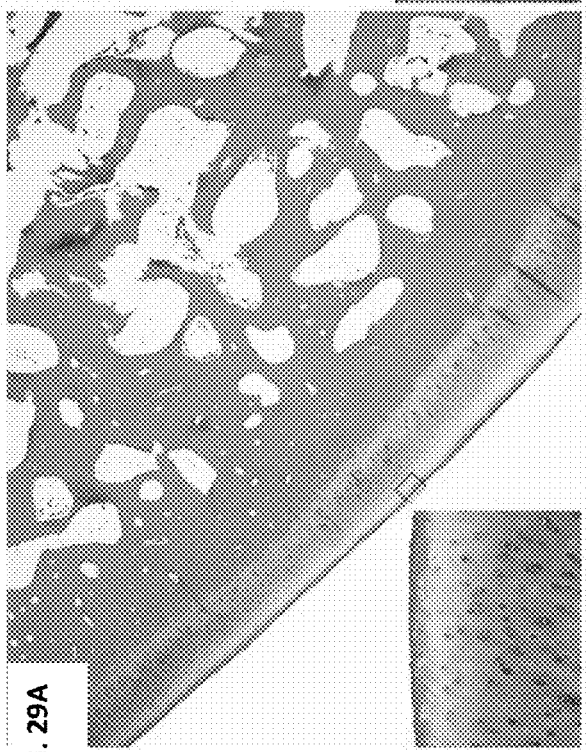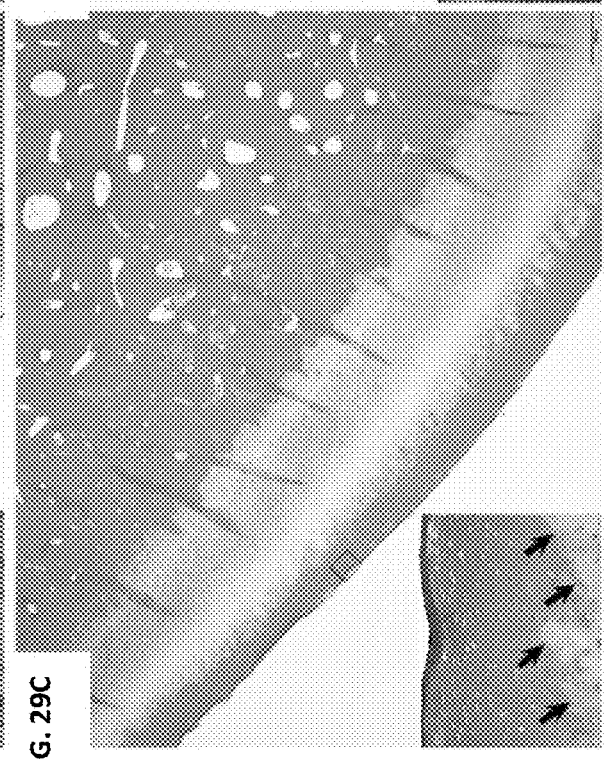

CATIONIC PLATELET LYSATE COMPOSITIONS AND RELATED METHODS

CROSS-REFERENCE TO RELATED APPLICATIONS

This application claims benefit of U.S. Provisional Patent Application Ser. No. 62/908,318, filed Sep. 30, 2019, the disclosure of which is incorporated by reference herein in its entirety.

STATEMENT OF GOVERNMENT SUPPORT

This invention was made with government support under grant numbers AR060875 and AR072513 awarded by the National Institutes of Health. The government has certain rights in the invention.

TECHNICAL FIELD

The presently disclosed subject matter relates to platelet-rich plasma lysate compositions and related methods of preparing and using the compositions.

BACKGROUND

Infectious arthritis is a life-threatening microbial colorization of a joint that carries a 7-15% mortality rate. Of those that survive, >50% will suffer long-term consequences such as cartilage damage. When bacteria enter a joint, they interact with synovial fluid and form free-floating bacterial aggregates, termed biofloats, which show strong antimicrobial recalcitrance and host immune tolerance. Compositions and methods that can be employed to treat infectious/septic arthritis, as well as other conditions including but not limited to periprosthetic joint infection and implant associated infections, are needed in the art.

SUMMARY

Provided in accordance with some embodiments of the presently disclosed subject matter is an acellular, anion-depleted platelet-derived peptide-rich composition comprising proteins, polypeptides and peptides <10 kDa in size, wherein the composition has anti-microbial and/or anti-inflammatory activity. In some embodiments, the composition is substantially free of non-active and immunogenic factors. In some embodiments, the composition has a platelet-to-bacteria ratio ≥1000:1. In some embodiments, the composition comprises plasma at a range of ≥10% to ≤50% plasma, optionally about 10% plasma.

Provided in accordance with some embodiments of the presently disclosed subject matter is a method of treating a microbial infection in a subject, the method comprising administering to the subject at the site of the infection an effective amount of a composition in accordance with the presently disclosed subject matter. In some embodiments, the microbial infection is infectious arthritis. In some embodiments, the microbial infection is caused by a gram-positive bacterium or a gram-negative bacterium.

Provided in accordance with some embodiments of the presently disclosed subject matter is a method of treating an inflammatory condition in a subject, the method comprising administering to the subject at the site of the inflammatory condition an effective amount of a composition in accordance with the presently disclosed subject matter.

Provided in accordance with some embodiments of the presently disclosed subject matter is a method of treating a wound in a subject, the method comprising administering to the subject at the site of the wound an effective amount of a composition in accordance with the presently disclosed subject matter.

Provided in accordance with some embodiments of the presently disclosed subject matter is a method for preparing an acellular platelet-derived peptide-rich composition having anti-microbial and/or anti-inflammatory activity. In some embodiments, the method comprises providing a starting material comprising platelet-rich plasma processed to contain ≥1,000,000 platelet/µL, ≤100 leukocytes/µL and ≤10 erythrocyte/µL in plasma; lysing and/or activating the starting material; contacting the starting material with an ion exchange matrix and/or a size exchange matrix; and isolating the acellular platelet-derived peptide-rich composition. Compositions prepared by the method are also disclosed.

In some embodiments, the starting material is provided from whole blood pooled from donor subjects. In some embodiments, the donor subject is an equine donor subject >1 year of age to <15 years of age. In some embodiments, the donor subjects comprise both female and male subject, optionally 50% females and 50% males. In some embodiments, the starting material is derived from whole blood collected in a citrate buffer. In some embodiments, the lysing is accomplished by exposing the starting material to one or more freeze/thaw cycles and/or mechanical homogenization.

In some embodiments, the method comprises testing for anti-microbial activity after the step of lysing and/or activating the starting material, the step of contacting the starting material with an ion exchange matrix and/or a size exchange matrix, and/or the step of isolating the acellular platelet-derived peptide-rich composition. In some embodiments, the method comprises adjusting plasma concentration in the composition to a range of ≥10% to ≤50% plasma, optionally about 10% plasma.

Accordingly, it is an object of the presently disclosed subject matter to provide platelet-rich plasma lysate (PRP-L) and/or BIO-PLY compositions and related methods of preparing and using the compositions. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting Examples and Figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows infected synovial fluid treated with platelet-poor plasma (PPP), leukocyte-reduced platelet-rich plasma (PRP) or leukocyte-rich platelet-rich plasma (L-PRP). FIG. 1B shows infected synovial fluid treated with varying concentrations (1×, 2×, 4×, 10× and 50×) of PRP. FIG. 1C shows 50× PRP activated with 20 mM $CaCl_2$ for 1 hour (A-PRP) or lysed by three consecutive freeze/thaw cycles (PRP-L) before centrifugation to remove any cellular debris. These acellular PRP formulations were used to treat infected synovial fluid alongside the original 50× PPP or PRP. Platelet formulations were generated from individual horses (n=8). Bars are means and standard deviations. Statistical analysis was performed by a 1-way ANCOVA with individual horse as a covariate and Tukey's post hoc test. Differing letters indicate statistical significance of $p<0.05$.

FIGS. 3A and 3B are bar graphs showing synergism of PRP-L with aminoglycosides against antimicrobial tolerant synovial fluid biofloats. Infections and treatments were carried out as previously described. Synovial fluid infected with *S. aureus* ATCC 25923 (FIG. 3A) or the four clinical isolates shown in FIG. 2 (FIG. 3B) was treated v/v with PBS (untreated control; NONE) or 50× platelet-rich plasma lysate (PRP-L) with or without the addition of 40 μg/mL or 10× MIC amikacin (ABX). Platelet formulations were generated from individual horses (n=6). Bars are means and standard deviations. Statistical analysis was performed by a 1-way (FIG. 3A) or 2-way (FIG. 3B) ANCOVA with individual horse or bacterial isolate as a covariate and Tukey's post hoc test. Differing letters indicate statistical significance of $p<0.05$.

(FIG. 4A) Platelets from 50× PRP were washed, suspended in PBS at equivalent volume (PLT) and subsequently lysed by three consecutive freeze thaw cycles (PLT-L). These formulations were used alongside PRP and PRP-L at the same 50× platelet concentration. (FIG. 4B) PRP-L was generated in different percentages of plasma as indicated by the percent (%) following PRP-L and compared to untreated PBS control (NONE), 10× MIC Amikacin (ABX) or plasma. (FIG. 4C) PRP-L was compared to PRP treated with proteinase inhibitors prior to lysis (PRP-L PI) and to PLT combined with plasma that was heat inactivated at either 65° C. or 95° C. for 30 minutes prior to lysis (PRP-L HIP65 or PRP-L HIP95, respectively). Platelet formulations were generated from individual horses (n=6). Bars are means and standard deviations. Statistical analysis was performed by a 1-way ANCOVA with individual horse as the covariate and Tukey's post hoc test. Differing letters indicate statistical significance of $p<0.05$.

FIGS. 8A through 8C is a bar graph and sets of images showing *S. aureus* within synovial fluid biofloats induced extracellular trap formation by neutrophils that can be reversed by the addition of BIO-PLY. *S. aureus* (ATCC® 25923) was grown as a single cell suspension (planktonic) in RMPI or as aggregates in synovial fluid (biofloat) for 3 hours. Neutrophils were isolated from healthy horses and incubated with each bacterial phenotype for 4 hours at a MOI of 10:1 with or without the addition of BIO-PLY at sub-antimicrobial concentrations. (FIG. 8A) Bar graph showing NET formation was quantified by the addition of 5 μM of the cell impermeable DNA binding dye (SYTOX® Green Nucleic Acid Stain, ThermoFisher Scientific Waltham, Mass.) for 10 minutes before fluorescence was measured with area scan settings on a microtiter plate reader. (FIG. 8B) Images showing immunofluorescent labeling (scale bar 20 μM) was performed using fluorescent stained *S. aureus* (green), anti-CitH3 (red) (NETs) and DAPI (PMN nuclei; blue). (FIG. 8C) Higher magnification of the immunofluorescent labeling (scale bar 10 μM). Data is shown as the mean±standard deviation of n=3. Differing letters indicate significant differences between groups ($p<0.05$); statistical analysis was performed by one-way ANCOVA with Tukey post-hoc and individual horse as the covariate.

(FIG. 9A) After 1 hour of incubation, phagocytosis was measured by quantifying extracellular and intracellular bacterial load. (FIG. 9B) Respiratory burst was evaluated 2 hours post infection by adding 10 μM DHR for 30 minutes prior to measuring fluorescence on a microtiter plate reader. (FIG. 9C) Bacterial survival was determined 8 hours post-infection. Bacterial load was quantified by serial dilutions and plate counting. Data is shown as the mean±standard deviation of n=3. Differing letters indicate significant differences between groups (p<0.05); statistical analysis was performed by one-way ANCOVA with Tukey post-hoc and individual horse as the covariate.

FIGS. 10A through 10D are bar graphs and sets of images showing treatment with BIO-PLY protected chondrocytes from biofloat induced chondrotoxicity. Synoviocytes and chondrocytes were isolated from the stifle of young horses (<5 years of age) by enzymatic digestion. Synoviocytes were seeded the top of a transwell insert while chondrocytes were seeded in the base well. After 72 hours in culture, $S.$ $aureus$ as biofloats or planktonic cells were introduced into the transwell insert containing synoviocytes. Co-cultures were left untreated or treated with BIO-PLY at sub-antimicrobial concentrations. Viability synoviocytes (FIG. 10A) and chondrocytes (FIG. 10C) were calculated as a percentage for each condition compared to seeding concentration. Images of both (FIG. 10B) synoviocytes and (FIG. 10D) chondrocytes were collected at 24 hours post-treatment and displayed as grayscale images. Data is shown as the mean±standard deviation of n=3. Differing letters indicate significant differences between groups (p<0.05); statistical analysis was performed by one-way ANCOVA with Tukey post-hoc and individual horse as the covariate.

(FIG. 13A) Line graph showing each horse was evaluated and scored for clinical signs of infection (pain score) on a scale of 0-3 (0=most normal, 3=most abnormal): lameness, tarsocrural swelling, distal limb edema, pain to palpation of the joint, and heat at the site of infection. Pain scores were lower for treatment horses at days 3-7, 14 and 21. (FIGS. 13B-13C) Photographic images showing experimental limbs were photographs at day 7 and a notable reduction in joint and distal limb effusion was appreciated in treatment horses (FIG. 13C) compared to control horses (FIG. 13B). Means and standard deviations of each group (control vs treatment; n=6), and significant differences*p<0.05p<0.01*p<0.001****p<0.0001 were determined by the Wilcoxon rank-sum test comparing control and treatment at each day (0-7, 14, and 21).

(FIG. 14A) Fibrinogen (mg/dL) was reported by the Clinical Pathology Laboratory at North Carolina State University. (FIG. 14B) D-dimer and (FIG. 14C) serum amyloid A (SAA) was measured in serum samples by the MILLIPLEX MAP Human Cardiovascular Disease (CVD) Magnetic Bead Panel (MilliporeSigma, MA, USA). Fibrinogen was lower in treatment horses at day 2-3, 6-7 and 21. D-dimer levels were lower in treatment horses from day 2-7, 14, and 21. No differences were noted in SAA between treatment and control. Means and standard deviations of each group (control vs treatment; n=6), and significant differences*p<0.05p<0.01*p<0.001****p<0.0001 were determined by the paired t-tests comparing control and treatment at each day (0-7, 14, and 21).

(FIG. 15A) No difference in synovial fluid total nucleated cell counts was appreciated from days 1-7 nor (FIG. 15B) total protein; however, lower neutrophil (FIG. 15C) and higher mononuclear cell percentages (FIG. 15D) were observed in the synovial fluid of BIO-PLY treated horses at days 6-7. Means and standard deviations of each group (control vs treatment; n=6), and significant differences*p<0.05p<0.01*p<0.001****p<0.0001 were determined by the paired t-tests comparing control and treatment at each day (0-7, 14, and 21).

(FIG. 16A, line graph) At days 7, 14, and 21 ultrasound scores were lower for BIO-PLY treated horses compared to control horses. Less fibrin deposition, synovial effusion and joint capsule thickening were observed in ultrasonographic images from BIO-PLY treated horses at the dorsomedial (FIG. 16B) and plantolateral (FIG. 16C) aspect of the tarsocrural joint. Means and standard deviations of each group (control vs treatment; n=6), and significant differences*p<0.05p<0.01*p<0.001****p<0.0001 were determined by the paired t-tests comparing control and treatment at each day (0, 1, 7, 14, and 21).

FIGS. 17A through 17L are line graphs showing BIO-PLY treatment altered cytokine parameters in synovial fluid. Concentrations of predominate inflammatory cytokines found in synovial fluid was quantified with the MILLIPLEX MAP Equine Cytokine/Chemokine Magnetic Bead Panel (MilliporeSigma, MA, USA) according to manufacturers' instructions. BIO-PLY treatment decreased (FIG. 17A) IL-1β at days 3-7, (FIG. 17B) IL-6 at day 7, (FIG. 17C) TNFα at day 5, (FIG. 17D) IL-8 at days 2-7, (FIG. 17E) MCP-1 at days 4-7, (FIG. 17F) G-CSF at days 2-7, (FIG. 17G) IL-18 at days 2-7, (FIG. 17H) IL-4 at days 2-7, (FIG. 17I) IL-5 at days 2-7, (FIG. 17J) IL-10 at days 4-7, and (FIG. 17K) IL-2 at days 4-5. (FIG. 17L) IFNγ was increased in BIO-PLY treated horses at day 2 but decreased in BIO-PLY treated horses at days 6-7. Means and standard deviations of each group (control vs treatment; n=6), and significant differences*p<0.05 p<0.01*p<0.001****p<0.0001 were determined by the paired t-tests comparing control and treatment at each day (0-7).

FIGS. 18A through 18J are line graphs showing BIO-PLY treatment did not alter concentrations of select cytokines. (FIG. 18A) FGF2, (FIG. 18B) eotaxin, (FIG. 18C) GM-CSF, (FIG. 18D) IL-1α, (FIG. 18E) fractalkine, (FIG. 18F) IL-13, (FIG. 18G) IL-17A, (FIG. 18H) IL-12p70, (FIG. 18I) IP-10, or (FIG. 18J) GRO were not different in the synovial fluid of control versus treatment horses from day 0-7. RANTES was the only biomarker that was not detectable in synovial fluid from any condition on any day.

FIGS. 19A through 19C are a photographic image and two plots showing treatment with BIO-PLY decreased bacterial load in the synovial fluid and synovial tissue at end-term. (FIG. 19A, photographic image) Synovial fluid biofloats were observed macroscopically in all horses prior to treatment or day 1. (FIG. 19B, plot) Bacterial load was measured in the synovial fluid from day 1-7 by enzymatic digestion, serial dilutions and plate counting. (FIG. 19C, plot) Synovium was collected from four sites in the joint (dorsomedial, dorsolateral, plantomedial, plantolateral), weighed, gently homogenized and enzymatically digested. Bacterial load was determined by serial dilutions and plate counting. BIO-PLY treated horses had a lower bacterial load (CFU/mL) in synovial fluid from day 2-7 and less bacteria within the synovial tissue at end-term or day 23-24. Means and standard deviations of each group (control vs treatment; n=6), and significant differences*p<0.05p<0.01 *p<0.001****p<0.0001 were determined by the paired t-tests comparing control and treatment at each day (0-7) and at end-term.

(FIG. 22A) Overall total synovium OARSI scores. (FIG. 22B) The individual synovial membrane outcome parameters that comprise the microscopic OARSI scoring system. Of all parameters, synovial vascularity and subintimal fibrosis showed the greatest differences between BIO-PLY treated and control horses.

FIGS. 23A through 23F show synovium inflammatory exudates. Low (2×) magnification (FIG. 23A, FIG. 23B) and high (20×) magnification (FIG. 23C-FIG. 23F) H&E stained photomicrographs of synovium from the plantarolateral region of tarsocrural joints from control (FIG. 23A, FIG. 23C, FIG. 23E) and BIO-PLY treated (FIG. 23B, FIG. 23D, FIG. 23F) horses. Although not a component of the OARSI scheme but compatible with ultrasound findings, the control horses often featured a thick fibrinocsuppurative exudate (FIG. 23A, asterisks) overlying an ulcerated synovial intima, as compared to the BIO-PLY treated horses which often had scant, paucicellular fibrinous exudate (B, asterisk) overlying focal intimal ulcers. OARSI scores in control horses also had more extensive areas of increased vascularity and fibrosis (FIG. 23A, double-headed arrows) as compared to BIO-PLY treated horses (FIG. 23A, double-headed arrows). Higher magnification of exudate from control horses had large aggregates of segmented neutrophils with rare cells (FIG. 23C, arrows) as compared to BIO-PLY treated horses which had rare neutrophils (FIG. 23D, arrows) within a predominant population of mononuclear cells. Control horses had thick disorganized beds of fibrovascular tissue that extended into the fibrinous exudate (FIG. 23E, arrows) and into the deeper layers of synovial stroma as compared to BIO-PLY treated horses that had comparatively more organized fibrovascular tissue limited to narrow bands immediately subtending the intimal surface (FIG. 23F, arrows). (2× mag, scale bar=500 μm; 20× mag, scale bar=50 μm).

FIGS. 25A through 25D display BIO-PLY treatment altered inflammatory cell infiltrates. High (20×) magnification photomicrographs of synovium from control (FIG. 25A, FIG. 25C) and BIO-PLY (FIG. 25B, FIG. 25D) treated horses stained with immunohistochemical stains including (FIG. 25A, FIG. 25B) S100A9 (myeloid leukocyte antibody) and (FIG. 25A, FIG. 25B-insets) CD204 (macrophage antibody), and (FIG. 25C, FIG. 25D) CD20 (B cell antibody). Photomicrographs correspond to same horses and synovial location depicted in FIGS. 23A through 23F. Control horses have large numbers of S100A9+ cells with segmented nuclei (i.e. neutrophils) concentrated within superficial fibrin exudates (FIG. 25A) and fewer numbers of CD204+ mononuclear cells (i.e., macrophages) (FIG. 25A-inset) as compared to BIO-PLY treated horses that have few scattered S100A9+ neutrophils localized to focal surface fibrin exudate and subintimal stroma (FIG. 25B); rare CD204+ mononuclear cells are identified within superficial exudate (FIG. 25B-inset). In control horses, rare CD20+ B cells are identified within superficial synovial stroma (FIG. 25C) as it merges with the superficial fibrin exudate (asterisks); deep stromal tissue contains small clusters associated with lymphoid aggregates (FIG. 25C-inset). In contrast, BIO-PLY treated horses have numerous CD20+ B cells concentrated within the superficial stroma (FIG. 25D) subtending the intimal lining (arrows); more numerous CD20+ B cells diffusely infiltrate and concentrate within lymphoid aggregates (FIG. 25D-inset) in deep layers of the synovial stroma. (20× mag; scale bar=50 μm).

FIG. 26A shows overall total OARSI scores. FIG. 26B shows the individual outcome parameters that makes up the microscopic OARSI scoring system.

FIGS. 29A through 29D show BIO-PLY treatment protected cartilage from proteoglycan loss predominantly within plantar joint compartments. Low magnification photomicrographs with high magnification insets of osteochondral sections stained with Safranin-O that highlight cartilage proteoglycan content from Control (FIGS. 29A and 29C) and BIO-PLY treated (FIGS. 29B and 29D) horses representing dorsomedial (FIGS. 29A and 29B) and plantarolateral (FIGS. 29C and 29D) regions of the tarsocrural joints. Although cartilage from dorsal locations of the joint has relatively similar proteoglycan content from control versus BIO-PLY treated groups, cartilage from plantar regions in the joint shows less severe depletion of proteoglycan content from BIO-PLY treated as compared to control horses where Safranin O depletion uniformly extends into the deeper layers of articular cartilage (FIG. 29C—inset, arrows). (Low 2× mag, scale bar=500 μm; High 20× mag inset, scale bar=50 μtm).

DETAILED DESCRIPTION

Infectious arthritis is a challenging condition that can lead to persistent infection necessitating euthanasia in veterinary patients or to degenerative joint disease in veterinary and human patients that survive. Using a clinically relevant translational animal model in the horse, we have recently shown that several arthrotropic pathogens, including *Staphylococcus aureus*, aggregate within equine synovial fluid to form free-floating biofilms, termed "biofloats". These biofloats are extremely difficult to eradicate and show antimicrobial resistance even when treated with antimicrobials at 100× the minimum inhibitory concentration (MIC). With overuse of antimicrobials and increasing bacterial resistance on the mind of veterinary and human clinicians alike, novel therapies are of particular interest. Autologous therapies, such as platelet-rich plasma (PRP), derived from equine and other species that are used regularly in the regenerative medicine industry have recently been reported to be antibacterial in vitro. Platelets are powerful players in innate immunity and, upon activation, produce an abundance of bioactive factors that can be directly bactericidal.

In accordance with the presently disclosed subject matter, the use of platelet-rich plasma (PRP) has been observed to be antibacterial against biofloats in vitro. Several different formulations of PRP were prepared and evaluated by a unique manual centrifugation method. Aspects of the method include mitigation of extraneous platelet activation and reduction of contamination with erythrocytes and leukocytes while optimizing antibacterial properties.

Figure 1C:
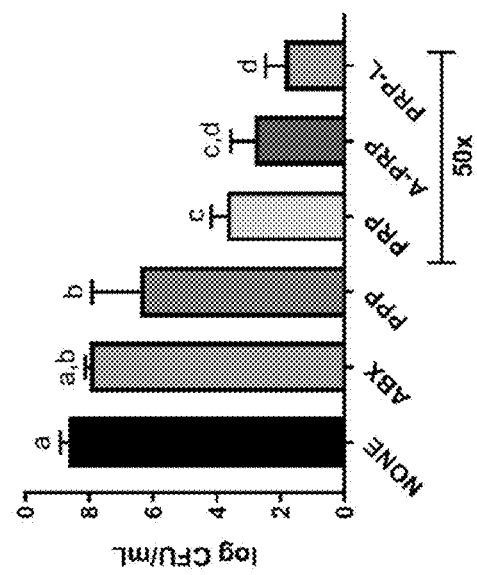
FIGS. 1A-1C are bar graphs showing anti-biofilm properties of platelet-rich plasma (PRP) formulations against *Staphylococcus aureus* synovial fluid biofilms termed biofloats.
Figure 1B:
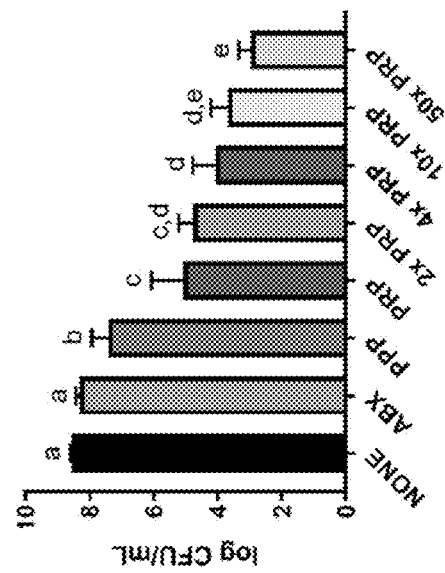
Figure 4C:
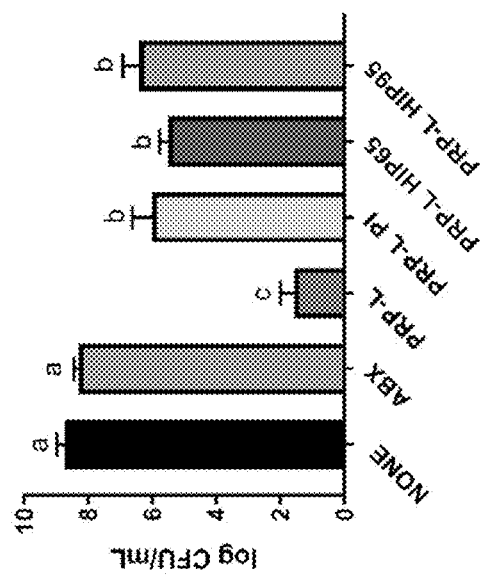
FIGS. 4A through 4C are bar graphs showing anti-biofilm effects of PRP-L are dependent upon proteolytic activity within the plasma. Synovial fluid infection with *S. aureus* ATCC 25923 and treatments were carried out as previously described with the standard untreated PBS control (NONE), 10× MIC Amikacin (ABX) and platelet-poor plasma (PPP).

In accordance with some embodiments of the presently disclosed subject matter, it was determined that the PRP formulation with high platelet concentrations (>10 fold over traditional PRP) were the most efficacious (FIG. 1B; $p<0.01$). This was confirmed by a strongly negative correlation between platelet count and bacterial load ($p<0.004$). Thereafter, lysis by freeze/thawing was used to extract the proteins within platelets and remove the cellular component of the PRP. The acellular lysis product of PRP (PRP-L) was significantly more bactericidal then the cellular PRP (FIG. 1C; $p<0.008$). It was also found that the presence of plasma in PRP-L, not just platelets alone, was more bactericidal (FIG. 4A; $p<0.002$). The efficacy of PRP-L was also tested against other pathogens (*Pseudomonas aeruginosa, Escherichia coli*, and *Streptococcus zooepidemicus*) and activity was found against all 3 pathogens compared to the untreated control (FIG. 2; $p<0.001$). Additionally, it was observed that the combination of traditional antimicrobials and PRP-L restored efficacy against previously antimicrobial tolerant biofloats (FIGS. 3A and 3B; $p<0.0001$). During processing it was observed that proteolytic activity in plasma during lysis plays a role in the anti-biofilm activity of PRP-L as the addition of protease inhibitors during lysis or heat inactivation of plasma prior to lysis removed the antimicrobial activity (FIG. 4C). Due to the published variation potential in autologous PRP and PRP-L, the effects of pooling PRP-L from multiple donors was tested. It was demonstrated here that pooled PRP-L was more potent and less variable then individual PRP-L (FIG. 5; $p<0.0001$).

In certain situations, bacteria can use large molecular weight anionic proteins such as fibrinogen to build biofilm communities. Therefore, it was desired to determine if removal of the anionic proteins in PRP-L would increase its efficacy. Ion exchange was performed to remove the anions or cations from PRP-L and discovered that the cationic fraction of PRP-L was more bioactive than the anionic component ($p<0.0001$) and the parent product (FIG. 6; $p<0.008$). Thus, the term "anion-depleted" refers to the removal of anionic proteins larger than 40 kDa.

In order to use a pooled allogenic product clinically, the potentially immunogenic immunoglobulins need to be removed. Immunoglobulins are typically >150 kDa but if cleaved by proteolysis can be ~25-50 kDa; thus, the cationic PRP-L fraction was passed through a size exclusion filter at 10 kDa. We tested the flow through (<10 kDa) fraction and the retentate (>10 kDa) fraction and determined that the <10 kDa cationic fraction of PRP-L was more bactericidal than the >10 kDa cationic fraction (FIG. 6; $p<0.002$). The conclusion of the in vitro studies was that the cationic, low molecular weight fraction of PRP-L was the most effective at combating bacteria grown in synovial fluid. Moving forward the bioactive fraction (cationic, <10 kDa) of pooled equine PRP-L is called BIO-PLY to stand for the BIOactive fraction of Platelet-rich plasma LYsate.

Subsequently, the in vitro findings were translated into an in vivo equine model of *S. aureus*-induced infectious arthritis. Using this model, it was hypothesized that the combination of BIO-PLY and amikacin will decrease bacterial burden and improve outcome parameters in an equine *S. aureus* infectious arthritis model compared to horses treated with amikacin alone. A highly concentrated (>50 fold), pooled PRP-L was generated from 8 healthy donor horses and processed to have the anionic fraction, including fibrinogen, removed and passed through a 10 kDa molecular weight cutoff filter to remove proteins >10 kDa termed BIO-PLY as stated above (IACUC protocol #16-189 of NC State University, Raleigh, N.C.). Bactericidal efficacy was confirmed in vitro prior to use in the study. Study horses (n=12; 7 mares, 4 geldings, 1 stallion; ages 2-14 years; multiple breeds) with normal physical examinations, bloodwork, and tarsocrural radiographs were randomly allocated into treatment or control groups (IACUC protocol #16-194 of NC State University). On day 0, epidural analgesia (buprenorphine and detomidine) was administered understanding sedation. *S. aureus* at $\times 10^6$ CFU in 1 mL sterile saline was then introduced via intra-articular injection into one randomly assigned tarsocrural joint. Twenty-four hours post-infection, horses were treated with BIO-PLY (5 mL) and 500 mg amikacin (treatment; n=6) or 500 mg of amikacin and sterile saline (5 mL) (control; n=6) daily for 7 days.

All horses received systemic antimicrobials (potassium penicillin and gentamicin) for 10 days post-infection as well as a tapering course of phenylbutazone for the duration of the study. Physical examinations were performed daily and pain scores based on lameness, hock swelling, distal limb swelling, pain to palpation, and presence of heat were calculated at days 0-7, 14 and 21. Ultrasound exams were performed on days 0, 1, 7, 14 and 21. Blood was collected on days 0-7, 14, and 21 for complete blood count, fibrinogen, D-Dimer and serum amyloid A (SAA) analyses. Synovial fluid was collected on day 0-7 and assessed for total protein (TP), total nucleated cell count (TNCC), cellular differential, and bacterial load determination, as well as biomarker analysis (EMD Millipore MILLIPLEX MAP Equine Cytokine/Chemokine Magnetic Bead Panel). Post-study radiographs were performed on Day 21. At end-term on day 24, horses were euthanized, and synovium and cartilage samples were collected for histopathology and tissue bacterial load determination in the infected tarsocrural joint.

Figure 14C:
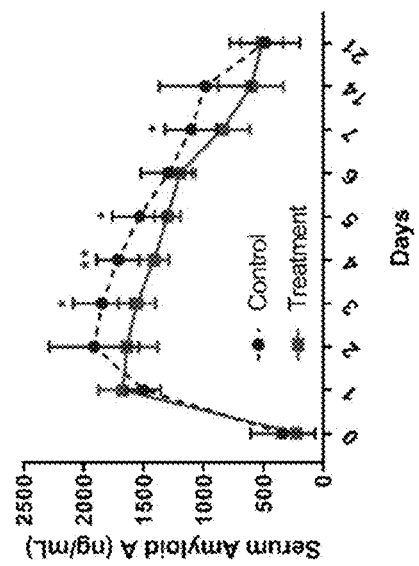
FIGS. 14A through 14C are line graphs showing BIO-PLY treated horses had lower systemic inflammation. Serum was collected on day 0-7, 14 and 21.
Figure 14B:
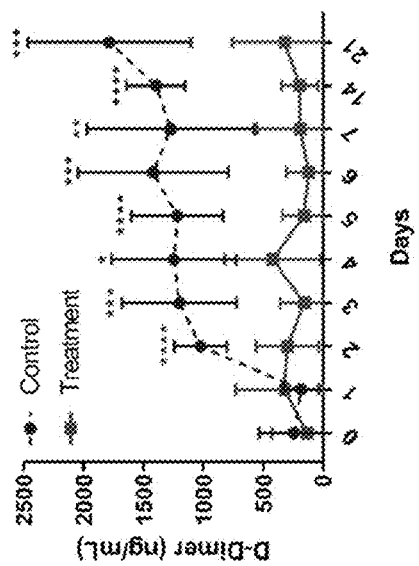
Figure 14A:
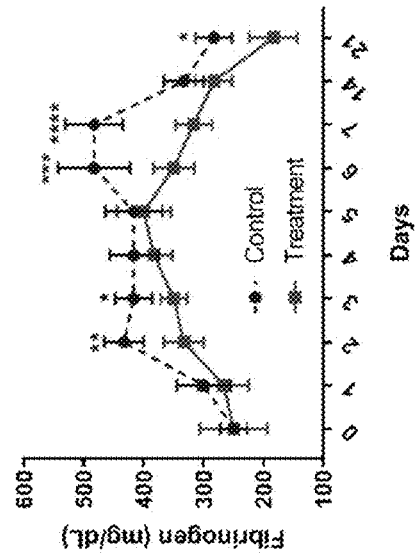
Figure 15B:
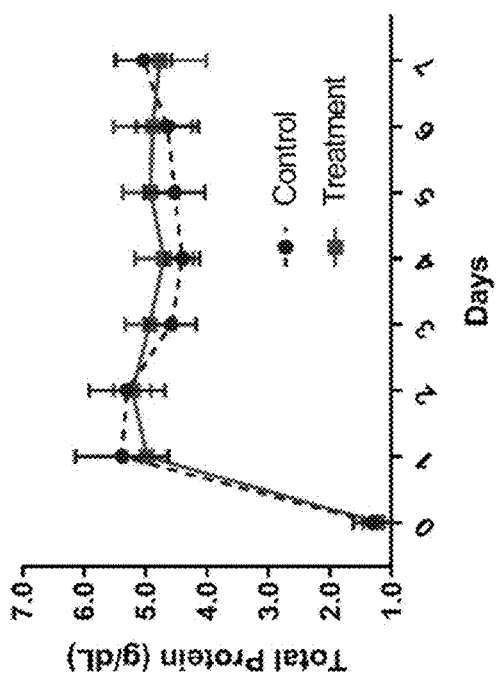
FIGS. 15A through 15D are line graphs showing BIO-PLY treatment altered cellular populations in the synovial fluid. Synovial fluid was collected from day 0-7 by arthrocentesis prior to infection at day 0 and prior to daily treatment from day 1-7 and submitted for analysis of total protein, total nucleated cell count and cellular differential to the Clinical Pathology Laboratory at North Carolina State University.
Figure 15D:
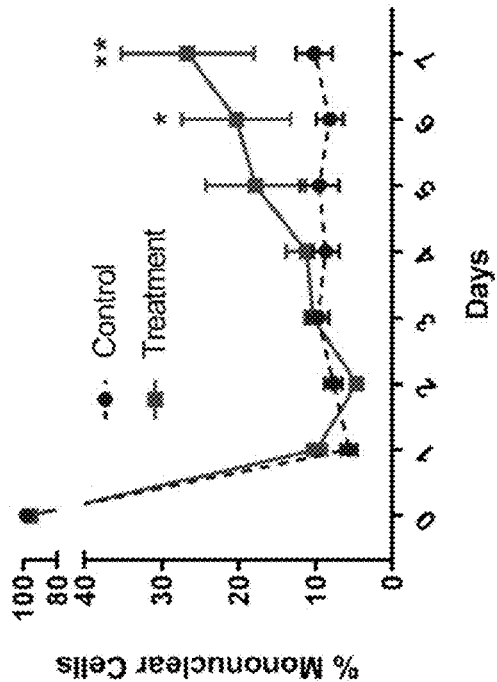
Figure 15A:
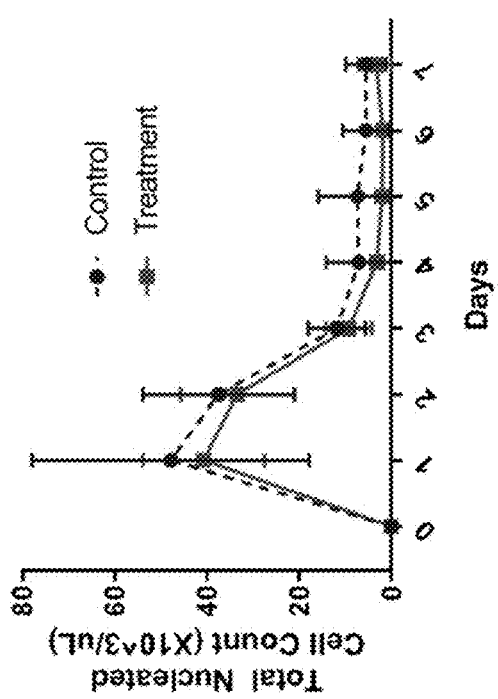
Figure 15C:
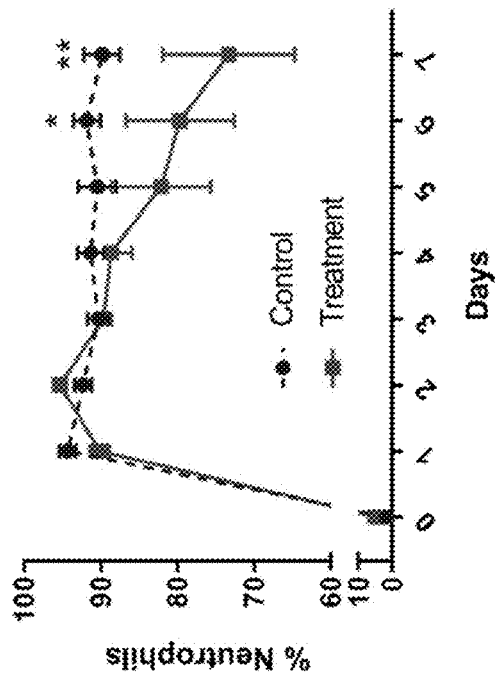
Figure 16B:
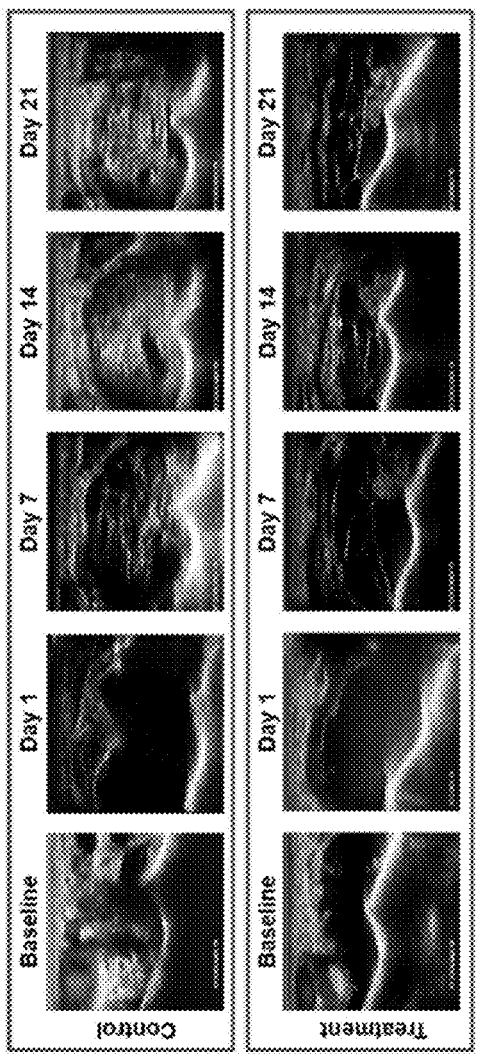
FIGS. 16A through 16C are a line graph and sets of ultrasound images showing treatment with BIO-PLY decreased ultrasound scores and altered appearance at day 7, 14 and 21. Ultrasonography was performed at day 0, 1, 7, 14, and 21 using the Aplio 500 system (Canon Medical Systems, CA, USA) with a linear 12 MHz broadband transducer. Transverse and longitudinal grayscale images of the dorsomedial and plantolateral recesses of the tarsocrural joint were acquired with the limb weight bearing. All images were evaluated by a radiologist unaware of treatment group. Ultrasound images were assessed using established criteria for infectious arthritis with each category scored on a scale of 0-3 (0=most normal, 3=most abnormal): degree of distension; degree of synovial thickening; character of synovial effusion; and presence of fibrinous loculations.
Figure 20:
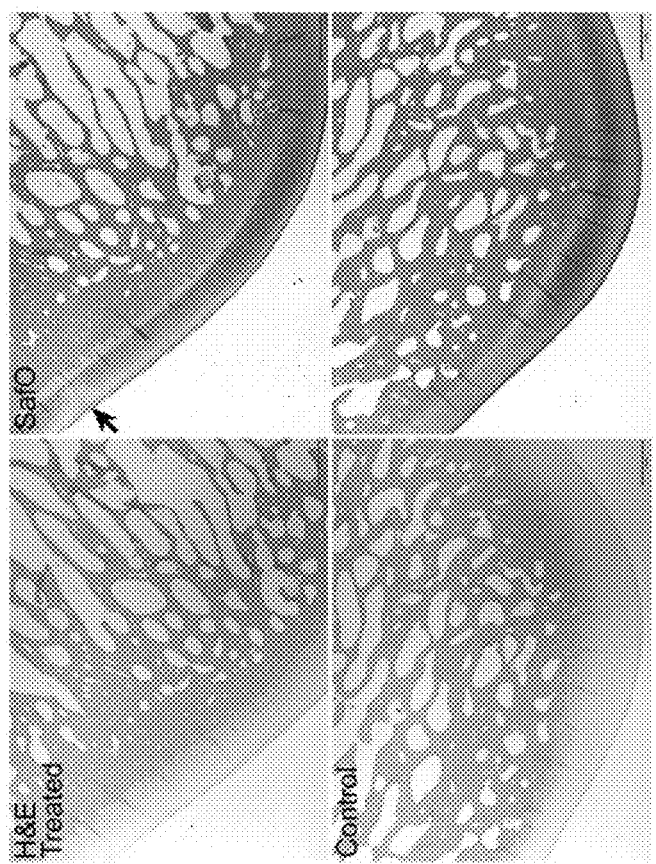
FIG. 20 is a set of images showing BIO-PLY treatment protected cartilage from proteoglycan loss. H&E (left panels) & Safranin-O (right panels) stained, formic-acid decalcified osteochondral sections explanted from site 1 of treated (A,B) and control (C,D) horses. The explant from the treated joint shows focal loss of Safranin-O staining that extends beyond the superficial layers of cartilage (arrow); however, the explant from the control joint shows regionally extensive loss of Safranin-O staining that extends into the deep layers of cartilage [1× mag; scale bar=1 mm].
Figures 21A, 21B, 21C:
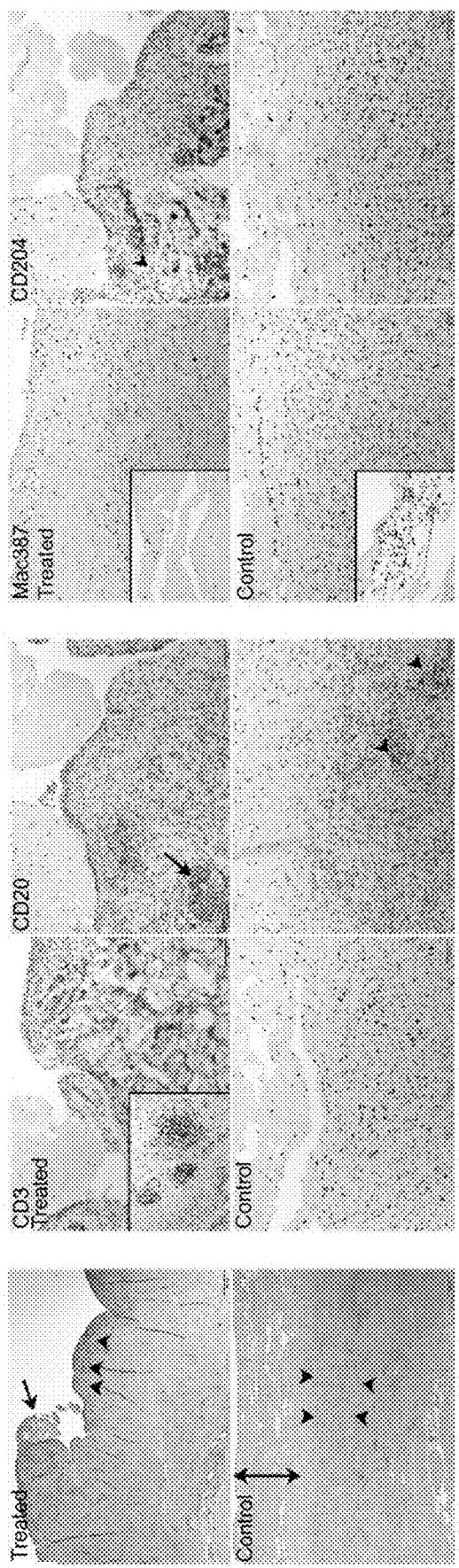
FIGS. 21A through 21C are a set of images showing BIO-PLY treatment altered cellular infiltrate and decreased fibrosis in the synovial tissue. H&E stained sections (left upper and lower panels) of synovium from a treated joint shows only a single focal erosion of the intimal layer with mild accumulation of fibrinous exudate (arrow), compared to diffuse erosion of the synovial intima with accumulation of a thick fibrinous exudate (double-headed arrow) in the control joint. Also, compared to the treated joint, the control joint has a thicker bed of granulation tissue (G) expanding the subintimal layers between the outer collagenous stroma (C) [2× mag; scale bar=500 μm]. Sections of synovium stained with immunohistochemical stains including CD3 (T cell antibody), CD20 (B cell antibody), and CD204 (macrophage antibody) show rare scattered T and B cells within the superficial layers of synovium of treated joints with occasional perivascular clusters of B cells (CD20, arrows), and T cell clusters (CD3, inset) within the deep synovial layers. Moderate numbers of CD204+ macrophages are scattered throughout the subintimal layers of treated joints with rare individual cell staining within the intimal layer. In contrast, synovium from control joints shows moderate diffuse infiltrates of T cells, B cells and macrophages within the subintimal layers and superficial exudate [10× mag; scale bar =100 μm].

All horses completed the study and maintained an acceptable comfort level. Tarsocrural joint sepsis was clinically evident in all horses following inoculation with *S. aureus* and synovial fluid TNCC increased from a mean of $133\pm77$ cells/µL on day 0 to a mean of $38,989\pm13,276$ cells/µL on day 1. Horses treated with BIO-PLY had lower pain scores at days 4-7, 14, and 21 ($p<0.05$; FIG. 13A) with most notable differences in hock and distal limb swelling (FIG. 13B). BIO-PLY treatment also substantially improved joint appearance on grey scale ultrasound imaging and ultrasound scores were lower in BIO-PLY treated horses at day 7, 14, and 21 ($p<0.05$; FIG. 16). Systemic fibrinogen was significantly lower in BIO-PLY treated horses at days 6 and 7 ($p<0.001$; FIG. 14A), as was D-dimer concentration at days 3-7, 14 and 21 ($p<0.05$; FIG. 14B). Serum amyloid A concentrations were not significantly different between BIO-PLY treated and control horses (FIG. 14C). Although no differences in synovial fluid TNCC or TP were appreciated between treated and control horses, BIO-PLY treated horses had a lower percentage of neutrophils ($p<0.01$; FIG. 15C) and higher percentage of mononuclear cells ($p<0.01$; FIG. 15D) at day 7 compared to control horses. Additionally, synovial fluid from BIO-PLY treated horses had lower concentrations of IL-18 ($p<0.01$; FIG. 17G), IL-4 ($p<0.008$; FIG. 17H), IL-5 ($p<0.02$, FIG. 17I), IL-8 ($p<0.03$, FIG. 17D), and G-CSF ($p<0.05$, FIG. 17F) from days 2-7; lower concentrations of MCP-1 ($p<0.03$, FIG. 17E) and IL-10 ($p<0.02$, FIG. 17A) from days 4-7; and lower concentrations of IFNγ ($p<0.02$, FIG. 17L) from days 6-7. No differences in concentrations of TNF-α (FIG. 17B) or IL-6, (FIG. 17C) were appreciated. Importantly, BIO_PLY treated horses had significantly lower concentrations of bacteria in synovial fluid at days 3-7 ($p<0.006$; FIG. 19B) and significantly less bacteria within the synovial tissue at end-term ($2.06\pm4.86$ CFU/g tissue) compared to horses treated with amikacin alone ($80.95\pm58.77$ CFU/g tissue) ($p<0.009$; FIG. 19C). The cartilage from horses treated with BIO-PLY had improved Safranin-O staining compared to control horses indicating increased proteoglycan content within the cartilage (FIG. 20). Treatment with BIO-PLY decreased erosion and fibrinous exudate along the intimal layer of the synovium (FIG. 21A; (arrow for treatment, double headed arrow for control)). In addition, treatment with BIO-PLY decreased the extent of granulation tissue in the subintimal layer of the synovium (FIG. 21A; indicated by the arrow heads). Treatment with BIO-PLY caused clustering of T and B cells (CD3+ and CD20+ respectively) compared to diffuse staining of T and B cells in control horses (FIG. 21B). BIO-PLY treated horses had a higher ratio of macrophage type 1 (M1, MAC387+) to macrophage type 2 (M2, CD204+) infiltrate compared to control horses (FIG. 21C).

The findings of this in vivo study to date strongly support the use of BIO-PLY in combination with antimicrobials to treat *S. aureus* infectious arthritis, among other embodiments. Although acellular, removal of immunoglobulins and major histocompatibility complex (MEW) fragments is confirmed and donor horses are screened for viral diseases which can be transmitted through biologics.

Despite a clear need for antimicrobials that target antimicrobial tolerant bacteria within biofilms/biofloats, currently there are no FDA-approved drugs that affect such bacteria. PRP-L or BIO-PLY show great promise as therapy against antimicrobial tolerant infections and makes the treatment of infected joints more effective, thereby decreasing the morbidity and mortality associated with these infections.

The presently disclosed subject matter will now be described more fully hereinafter with reference to the accompanying Examples and Figures, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art. Certain components in the figures are not necessarily to scale, emphasis instead being placed upon illustrating the principles of the presently disclosed subject matter (in some cases schematically).

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

While the following terms are believed to be well understood by one of ordinary skill in the art, the following definitions are set forth to facilitate explanation of the presently claimed subject matter.

Following long-standing patent law convention, the terms "a", "an", and "the" refer to "one or more" when used herein, including in the claims.

As used herein, the term "about", when referring to a value or an amount, for example, relative to another measure, is meant to encompass variations of in some embodiments ±20%, in some embodiments ±10%, in some embodiments ±5%, in some embodiments ±1%, and in some embodiments ±0.1% from the specified value or amount, as such variations are appropriate. The term "about" can be applied to all values set forth herein.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed in some embodiments as a "p-value". Those p-values that fall below a user-defined cutoff point are regarded as significant. In some embodiments, a p-value less than or equal to 0.05, in some embodiments less than 0.01, in some embodiments less than 0.005, and in some embodiments less than 0.001, are regarded as significant.

As used herein, an "effective amount" or means an amount sufficient to produce a selected effect, such as inhibiting the growth of a microbe or a microbial biofloat, or disrupting a microbial biofloat, including on a surface. In the context of administering compositions in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

In some embodiments, a composition in accordance with the presently disclosed subject matter is referred to as BIO-PLY. The BIO-PLY (cationic low molecular weight fraction of highly concentrated, pooled PRP-L) product is a novel, innovative biological treatment that will not only reduce morbidity and mortality in patients afflicted with chronic and/or persistent infections but will also combat antimicrobial resistance and tolerance. New treatments that can combat bacteria in biofilm formation are increasingly needed in both human and veterinary medicine. The isolation of the bioactive components of PRP-L shows great promise to provide a more effective and more targeted drug therapy against chronic infections such as infectious arthritis, and to mitigate the deleterious effects of persistent infection and inflammation associated with this disease. The presently disclosed subject matter is highly translatable, not only greatly helping veterinary species, but humans suffering from infectious arthritis, periprosthetic joint infection or other implant associated biofilm infection as well. Recently, the World Health Organization has reported a significant drop in the number of new antimicrobials in development since 2000. Therefore, in this an era of widespread concern over antimicrobial resistance, the development of new antimicrobial drugs that combat tolerant bacterial infections while improving traditional antimicrobial efficacy is increasingly important.

The BIO-PLY product is a bioactive component of allogenic lysed platelet-rich plasma (PRP), which has potent bactericidal activity against antimicrobial tolerant infections. By isolating the cationic, low molecular weight fraction a pooled PRP preparation, an innovative treatment is formulated, which will not only reduce morbidity and mortality in patients afflicted with chronic infections, but also provide a product that combats antimicrobial resistance and tolerance. Currently, there are no drugs available on the market and little in development that directly combat bacteria within biofilms or a persister cell phenotype. Most new antimicrobials that have been developed since the 1980s are simply derivatives of already available drugs without novel mechanisms of action. As all currently available antibiotics are unable to effectively combat bacteria within biofilms or persister cell phenotypes, the mechanism of action of PRP proteins, polypeptides or peptides is most likely distinct. Additionally, one of the major setbacks in bringing new drugs from bench to bedside are the side effects. As the proteins from PRP and BIO-PLY are natural antibiotics derived from a mammalian species, side effects of their use will most likely be diminished compared to drugs derived from non-mammalian sources. Also, the immunogenic component of the product is removed by removing the immunoglobulins. Thus, a composition in accordance with the presently disclosed subject matter addresses at least two obstacles facing most new anti-infective drugs, making it extremely novel and unique.

In some embodiments, the subject treated according to the presently disclosed subject matter is a human subject, although it is to be understood that the methods described herein are effective with respect to all mammalian species, which are intended to be included in the term "subject."

More particularly, provided herein is the treatment of mammals, such as humans, as well as those mammals of importance due to being endangered, of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, and the like.

In some embodiments, BIO-PLY is used as an adjunctive therapy for *Staphylococcus aureus* infectious arthritis, as supported inter alia with the substantial in vitro and in vivo data provided herein. Data to support use of BIO-PLY against other bacterial pathogens, such as *Pseudomonas aeruginosa*, is also available. BIO-PLY can be used against other bacterial diseases in which local delivery can be implemented. These include, but are not limited to, pneumonia, pleuropneumonia, pleuritis, wounds, peritonitis, abscesses, infected surgical implants, osteomyelitis, endometritis, ocular infections, amongst others.

In some embodiments, a BIO-PLY composition in accordance with the presently disclosed subject matter, which could comprise anti-microbial peptides, is employed in anti-bacterial, anti-protozoal, anti-fungal, anti-parasitic, anti-inflammatory, pro-regenerative, immunomodulatory, wound healing and/or anti-cancerous indications. Data in the joint show that BIO-PLY is anti-inflammatory and regenerative. It is also shown that BIO-PLY decreases inflammation in synoviocytes (the resident cell of the joint) and increases production of hyaluronic acid. Pilot data show that BIO-PLY increases chondrocyte differentiation. Therefore, BIO-PLY has the potential to combat osteoarthritis, to combat synovitis, and to help restore damaged cartilage. In an ex vivo model of infectious arthritis with *S. aureus*, BIO-PLY, at sub-antimicrobial concentrations, increased neutrophil antibacterial and antibiofilm activity by increasing neutrophil phagocytosis and bacterial clearance while decreasing the release of harmful inflammatory mediators. This observed immunomodulation could lead to a multimodal approach to combating bacterial infection by having direct antimicrobial activity, stimulating the host immune response to perform better and providing protection to the surrounding tissue through anti-inflammatory activity.

Infectious arthritis is a life-threatening microbial colonization of a joint that carries a 7-15% mortality rate. Of those that survive, >50% will suffer long-term consequences such as cartilage damage leading to joint degeneration. When bacteria enter a joint, they interact with synovial fluid and form free-floating biofilms or biofloats, that show severe antimicrobial recalcitrance and host immune tolerance. Platelet-rich plasma (PRP) is an autologous biologic made from a patient's whole blood that is most commonly used to treat musculoskeletal conditions such as osteoarthritis. Interestingly, recent reports suggest that PRP has bacteriostatic and immunological effects. Platelets are important players in innate immunity and, when activated, degranulate and release antimicrobial peptides (AMPs).

In some embodiments, the presently disclosed subject matter provides a platelet-derived biologic rich in AMPs termed BIO-PLY. Data shows a potent bactericidal effect of BIO-PLY both in vitro against *Staphylococcus aureus* biofloats and in vivo in a clinically relevant equine model of *S. aureus* infectious arthritis. In vitro, BIO-PLY exhibited a 5-6 log reduction of bacteria within antimicrobial recalcitrant biofloats of both gram-positive and gram-negative species. In vivo, BIO-PLY treatment decreased synovial fluid bacterial load by day 5 post infection and resulted in little to no bacterial burden within the synovial tissue at end-term.

It is also shown that BIO-PLY has immunomodulatory and chondroprotective properties. In an ex vivo model of infectious arthritis with *S. aureus*, BIO-PLY, at sub-inhibitory concentrations, increased neutrophil activity by increasing neutrophil phagocytosis and bacterial clearance while decreasing the release of harmful inflammatory mediators. In vivo, BIO-PLY treatment reversed the immunosuppression induced by *S. aureus* infectious arthritis. Additionally, BIO-PLY protected cartilage from damage induced by *S. aureus* infection ex vivo and in vivo. Ex vivo, in a synoviocyte-chondrocyte co-culture model it was observed that BIO-PLY treatment decreased release of inflammatory mediators by synoviocytes and increase extracellular matrix gene expression and proliferation of chondrocytes. In vivo, the cartilage of horses treated with BIO-PLY had fewer arthritic changes and an intact extracellular matrix. Taken together, compositions in accordance with the presently disclosed subject matter, rich in AMPs, possess multimodal properties that provide to a unique anti-infective, which can be translated into a therapeutic for veterinary or human clinical practice.

Thus, in some embodiments, a composition in accordance with the presently disclosed subject matter, referred to herein as BIO-PLY, is a platelet-derived peptide-rich biologic comprising proteins, polypeptides and peptides <10 kDa in size and/or with an isoelectric point (pI)≥7. The parent of BIO-PLY is platelet-rich plasma; however, BIO- PLY is acellular. The acellularity due to lysis is an advantage as several bacterial species can hijack platelets as virulence factors. The acellular nature also allows for the pooling of the product amongst several individuals, which capitalizes on the natural variability of individual to yield a more potent, consistent product. In some embodiments, the <10 kDa and/or ≥7 pI of BIO-PLY removes several non-active and immunogenic factors. The non-active factors that are removed by ion exchange, such as fibrinogen, can be inflammatory to tissues and can also be utilized by bacteria as virulence factors. Therefore, removal of the non-active, typically coagulation proteins is advantageous to the final product. In addition, the ion exchange and size exclusion remove immunogenic factors such as antibodies that could be inflammatory to recipient subjects due to the pooled nature of the product.

In some embodiments, a starting material for BIO-PLY is platelet-rich plasma processed to contain ≥1,000,000 platelet/µL, ≤100 leukocytes/µL and ≤10 erythrocyte/µL in plasma. The platelet concentration is at least 10-fold higher than normal platelet counts in whole blood. Current PRP tends to have platelet counts 1-4-fold higher than whole blood. A composition in accordance with the presently disclosed subject matter is significantly more concentrated. In addition, a composition in accordance with the presently disclosed subject matter is much purer as in some embodiments, processing is adjusted to exclude significantly more erythrocytes and leukocytes into the final product than traditional PRP formulations. The platelet concentration plays a role in that in some embodiments, to be bactericidal platelet-to-bacteria ratios are ≥1000:1 to generate >95% bacterial killing. In general, most bacterial infections are $\sim 1 \times 10^6$ CFU/mL; therefore, in some embodiments, a composition in accordance with the presently disclosed subject matter is generated at an average platelet-to-bacteria ratio of >1000:1. In addition, most PRP formulations are made in 100% plasma. However, in accordance with an aspect of the presently disclosed subject matter, it has been found that a range of ≥10% to ≤50% is more efficacious than 100% plasma. Therefore, in some embodiments, BIO-PLY is generated from PRP-L in 10% plasma. This also aids in processing as it puts less stress on the ion exchange and size exclusions steps due to less high molecular weight plasma proteins and anionic coagulation proteins present within BIO-PLY.

In some embodiments, the starting material is provided from whole blood from one or more donor subjects, such as whole blood pooled from donor subjects. Ages can vary for the donor subjects. Donor subjects can include adult donor subjects, such as but not limited to young adult donor subjects.

In some embodiments, the donor subjects are equine donor subjects, human donor subjects, canine donor subjects, or porcine donor subjects. By way of example and not limitation, in equine donor subjects, the ages of the equine donor subjects can fall in the range of >1 year of age to <15 years of age. In some embodiments, the donor subjects comprise both female and male subject, optionally 50% females and 50% males. In some embodiments, the starting material is derived from whole blood collected in a citrate buffer. In some embodiments, the lysing is accomplished by exposing the starting material to one or more freeze/thaw cycles or mechanical homogenization.

In some embodiments, in order to generate a desired amount of BIO-PLY, whole blood is collected from a minimum of 6 healthy horses >1 year of age and <15 years of age. Horses that are too young or old produce ineffective PRP. in some embodiments, the blood donors comprise 50% females and 50% males to capitalize on the sex differences in PRP. Whole blood is collected into 60 mL syringes containing 1:9 parts acid citrate dextrose A (ACD-A). Blood collection can be performed in fasted animals to provide low blood glucose levels, if desired. In addition, blood can be collected in a particular fashion to ensure horses are quiet and the blood collection is performed slowly. Platelets can be activated by a plethora of factors including shear stress. Therefore, large diameter extensions sets and syringes as well as needles with a minimum gauge of 18 are employed, in some embodiments. In some embodiments, the first 10 mL of blood is wasted during collection to ensure tissue factor does not contaminate the product as that protein is generated during venipuncture and can activate platelets as well. Whole blood is collected a minimum of three times from each horse once per week to decrease day-to-day variability in platelet activity (older platelets in circulation will be less antibacterial). A minimum of 500 mL is collected from each horse at each blood collection.

Processing steps can be slightly different depending on the mammalian species. For example, in horses, erythrocytes are very heavy and settle quickly but in cattle and pigs this does not occur, so an additional centrifugation step is employed.

After collection, whole blood is rested for 30-60 minutes, which allows erythrocytes to settle in the syringe. Thereafter, the layer above the erythrocytes containing the leukocytes, platelets and plasma, also called leukocyte-rich platelet-rich plasma or L-PRP, is gently transferred to a 50 mL conical tube. The L-PRP is centrifuged at 250 g for 15 minutes to generate PRP or the layer containing platelets and plasma above the leukocyte pellet. The PRP is gently transferred to a new 50 mL conical tube and centrifuged at 1500 g for 15 minutes to pellet the majority of platelets. The supernatant above the platelet-pellet, or platelet-poor plasma (PPP), is removed and saved. The remaining platelet pellet is then re-suspended in 2% of the original PPP volume to generate PRP containing ≥1,000,000 platelet/µL. The concentrated PRP is centrifuged at 100 g for 10 minutes to remove any remaining leukocyte or erythrocyte contaminants. Leukocyte, erythrocyte and platelet concentrations in each formulation are counted. If leukocyte concentrations are >100 leukocytes/µL, the PRP is centrifuged again at 100 g for 10 minutes until the derived leukocyte reduction is achieved. If platelet concentrations are <1,000,000 the product is centrifuged again at 1500 g for 15 minutes and resuspended in less PPP. To generate PRP lysate (PRP-L), concentrated PRP is subjected to five freeze/thaw cycle at −80° C. for a minimum of 1 hour and 37° C. for a minimum of 15 minutes. The majority of cell debris is removed from PRP-L after freeze/thaw by centrifugation at 20,000 g for 20 minutes. The resulting PRP-L is clarified by passing the product through a 0.2 µM bottle-top filter. The PRP-L is pooled within the individual and tested for efficacy. PRP-L that decreases bacterial load >95% is pooled amongst multiple individuals. The pooled PRP-L (pPRP-L) undergoes anion depletion by incubating pPRP-L with loose strong anionic exchange media for 1 hour. After incubation, the pPRP-L/anion exchange media slurry is passed thru a 0.2 µM bottle-top filter to remove anion exchange media. The resulting anion-depleted pPRP-L is tested for efficacy as before and if the >95% bacterial killing is maintained the product undergoes size exclusion with molecular weight cutoff filters at 10 kDa per manufacturers' instructions. The <10 kDa product is passed thru a 0.1 µM bottle-top filter to remove any pathogen contamination. The final product is screened for removal of antibodies and fibrinogen by ELISA and is verified at physiologic electrolyte concentrations using a handheld blood gas analyzer. The final product is also, once again, tested for >95% bacterial killing before use in an experiment or in clinical cases.

BIO-PLY has been validated and proven efficacious for use in equine infectious/septic arthritis. It is effective against both lab-adapted and drug-resistant clinical strains of both gram-positive and gram-negative bacteria; however, it is more efficacious against gram-positive bacteria by 2-3 logs. Other local equine infections that can be treated using BIO-PLY including but not limited to pneumonia, osteomyelitis, endometritis, peritonitis, ocular infections, abscesses, infected implants and catheters and infected wounds. BIO-PLY is also employed as an osteoarthritis drug as it has more than just antibacterial properties. It is an extremely robust anti-inflammatory and has regenerative properties as well. These functions of BIO-PLY are similar to what has been reported for traditional PRP; however, due to the nature of BIO-PLY it is more consistent, less variable, and more potent than current PRP formulations. For these alternative uses, the components and processing methods do not change for BIO-PLY, Currently, BIO-PLY can be delivered locally at the site of infection such as direct injection into infected joints, topically for wounds or nebulized to pneumonia cases. BIO-PLY has proven synergistic with traditional antimicrobials and has been shown to work especially well with aminoglycosides.

Currently, the present Examples show BIO-PLY being made and used in horses; nevertheless, other species such as pigs, cattle, dogs and humans have been used to generate BIO-PLY. Minor alterations to the processing techniques are required due to differences in mammalian blood components, sizes and weights. However, all mammalian species tested thus far have shown the same activity as equine BIO-PLY. In some embodiments, BIO-PLY is generated in pigs to combat pneumonia. In some embodiments, BIO-PLY is generated in cattle to combat mastitis (a major infection that effects the dairy industry). While BIO-PLY might vary in activity, potency and/or spectrum between species, it is expected to remain efficacious overall.

BIO-PLY was tested for antibacterial activity against both gram-positive and gram-negative drug-susceptible and drug-resistant species and have shown activity against all isolates. BIO-PLY was also tested for anti-inflammatory activities in synoviocyte-chondrocyte co-cultures (the main cell types in the joint) and for immunomodulatory properties with neutrophils (the main leukocyte at the site of joint infections). BIO-PLY shows not cytotoxicity or hemolytic activity proving it is safe to use in vivo.

Figures 11A, 11B, 11C:
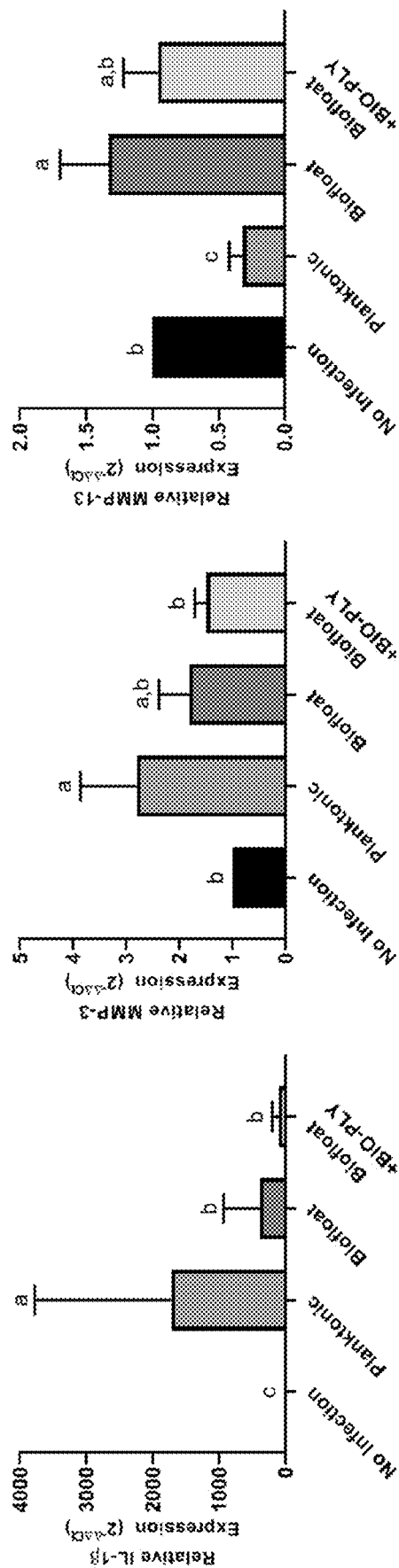
FIGS. 11A through 11C are bar graphs showing biofloats decreased IL-1β and increased MMP-13 gene expression in synoviocytes compared to planktonic $S.$ $aureus$. Total cellular RNA was extracted from synoviocytes. Quantitative real time RT-PCR (qPCR) was performed using previously published equine primers to amplify IL-1β, MMP-3, and MMP-13 with GAPDH used as a housekeeping gene. Relative gene expression of each infection and/or treatment was calculated as $2^{-\Delta\Delta Ct}$ compared to the untreated control. Data is shown as the mean±standard deviation of n=3. Differing letters indicate significant differences between groups (p<0.05); statistical analysis was performed by one-way ANCOVA with Tukey post-hoc and individual horse as the covariate.
Figure 12A:
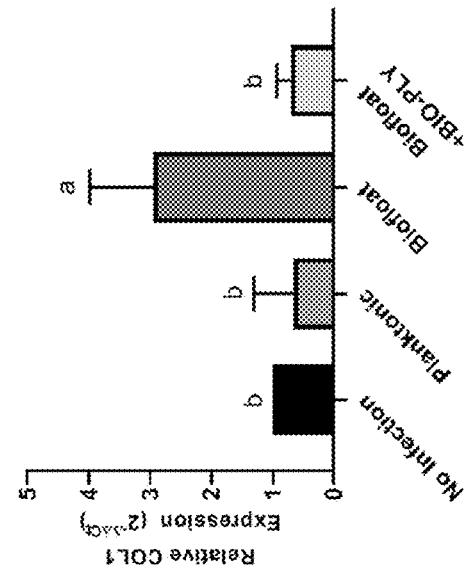
FIGS. 12A through 12C are bar graphs showing bacteria within biofloats caused dysfunctional chondrocyte collagen expression that is restored by BIO-PLY treatment. Total cellular RNA was extracted from chondrocytes. Quantitative real time RT-PCR (qPCR) was performed using previously published equine primers to amplify COL1 and COL2 with GAPDH used as a housekeeping gene. Relative gene expression of each infection and/or treatment was calculated as $2^{-\Delta\Delta Ct}$ compared to the untreated control. Data is shown as the mean±standard deviation of n=3. Differing letters indicate significant differences between groups (p<0.05); statistical analysis was performed by one-way ANCOVA with Tukey post-hoc and individual horse as the covariate.
Figure 12B:
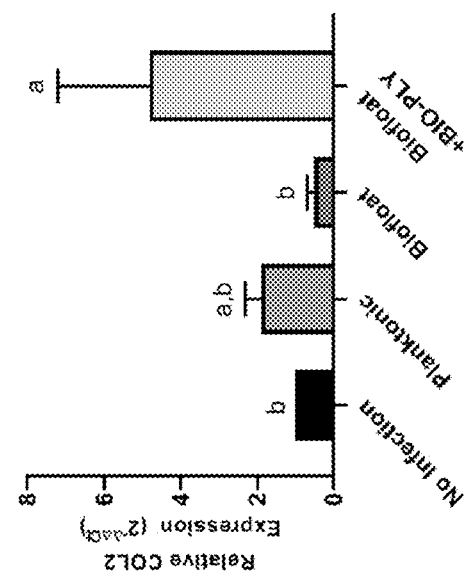
Figure 12C:
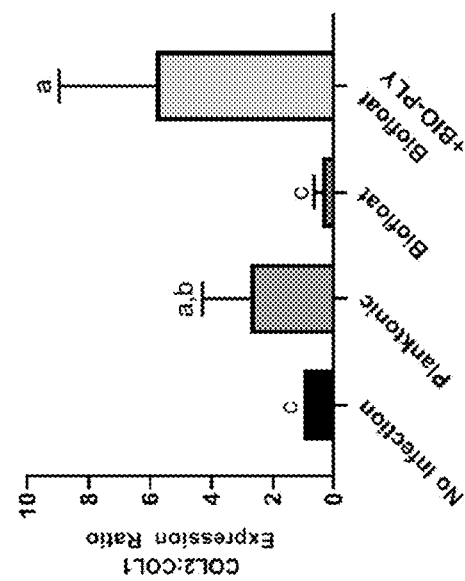

Provided herein are data showing the antibacterial activity of BIO-PLY against the aforementioned bacteria when grown in synovial fluid. Also provided herein are data showing that BIO-PLY decreases IL-1β and MMP production by synoviocytes in the presence of infection (FIGS. 11A, 11B, and 11C). Also provided herein are data showing that RIO-PLY protects cartilage during infection by maintaining the gene expression of normal extracellular matrix components such as type II collagen (FIGS. 12A, 12B, and 12C). Also provided herein are data showing that BIO-PLY balances neutrophil functionality by decrease the release of harmful inflammatory mediators while increase the neutrophil's antibacterial capacity (FIGS. 8A through 9C).

The presently disclosed subject matter provides a novel platelet-derived biologic, as no currently available products are as potent and well-defined as BIO-PLY. To date, no other disclosures in the art have validated the multi-modal properties in the context of a single disease. Provided herein is a product, and methods of making and using the same, that is antibacterial, immunomodulatory, anti-inflammatory and chondroprotective both in vitro, ex vivo and in vivo. This product serves as a basis for development of similar products from other species and for use in other disease processes.

Methods used to generate equine BIO-PLY can be used to generate BIO-PLY from other species, such as but not limited to humans, dogs, pigs and cattle. The use of BIO-PLY to treat infectious arthritis in horses is shown herein, but this product can be used to treat any local infection or local sterile inflammation, such as osteoarthritis. Examples of local infections that can be treated with BIO-PLY include but are not limited to wounds, pneumonia, peritonitis, uveitis, sinusitis, endometritis, and mastitis. Thus, in addition to the use of equine BIO-PLY for the treatment of infectious arthritis, the uses of porcine BIO-PLY for pneumonia and bovine BIO-PLY for mastitis are also provided. A clinical trial in horses that validates the use of equine BIO-PLY to treat infectious arthritis in a clinical setting is being performed. Studies supporting the use of porcine and bovine derived BIO-PLY for the use in porcine pneumonia and bovine mastitis are also being performed.

The Examples and Figures provided herein have been included to provide guidance to one of ordinary skill in the art for practicing representative embodiments of the presently disclosed subject matter. In light of the present disclosure and the general level of skill in the art, those of skill can appreciate that the following Examples and Figures are intended to be exemplary only and that numerous changes, modifications, and alterations can be employed without departing from the scope of the presently disclosed subject matter.

EXAMPLE 1

Figure 1A:
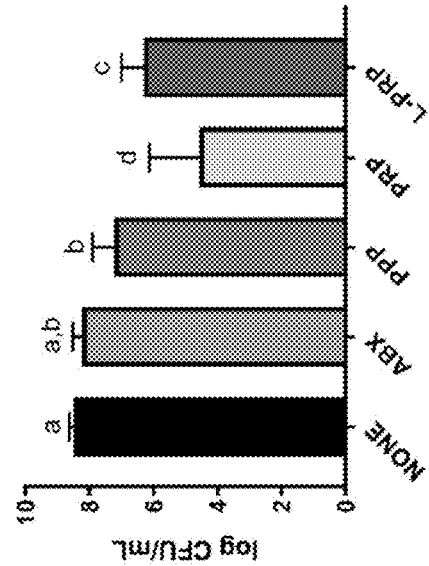

Anti-Biofilm Properties of Platelet-Rich Plasma (PRP) Formulations Against *Staphylococcus aureus* Synovial Fluid Biofilms Termed Biofloats Referring to FIGS. 1A to 1C, infected synovial fluid was subsequently treated with the respective PRP formulations v/v for 8 hours under the same conditions as the infective period. The untreated control (NONE) was treated v/v with phosphate buffered saline (PBS) while the antimicrobial control (ABX) was treated with 40 μg/mL or 10× MIC amikacin in the same volume of PBS. Thereafter, bacterial load was quantified by serial dilution and plate counting and displayed on the y-axis of each graph as a log transformed CFU/mL. Treatments are described along the x-axis. Referring to FIG. 1A, infected synovial fluid was treated with platelet-poor plasma (PPP), leukocyte-reduced platelet-rich plasma (PRP) or leukocyte-rich platelet-rich plasma (L-PRP). Referring to FIG. 1B, infected synovial fluid was treated with varying concentrations (1×, 2×, 4×, 10× and 50×) of PRP. Referring to FIG. 1C, 50× PRP was activated with 20 mM $CaCl_2$ for 1 hour (A-PRP) or lysed by three consecutive freeze/thaw cycles (PRP-L) before centrifugation to remove any cellular debris. These acellular PRP formulations were used to treat infected synovial fluid alongside the original 50× PPP or PRP. Platelet formulations were generated from individual horses (n=8). Bars are means and standard deviations. Statistical analysis was performed by a 1-way ANCOVA with individual horse as a covariate and Tukey's post hoc test. Differing letters indicate statistical significance of p<0.05.

EXAMPLE 2

Figure 2:
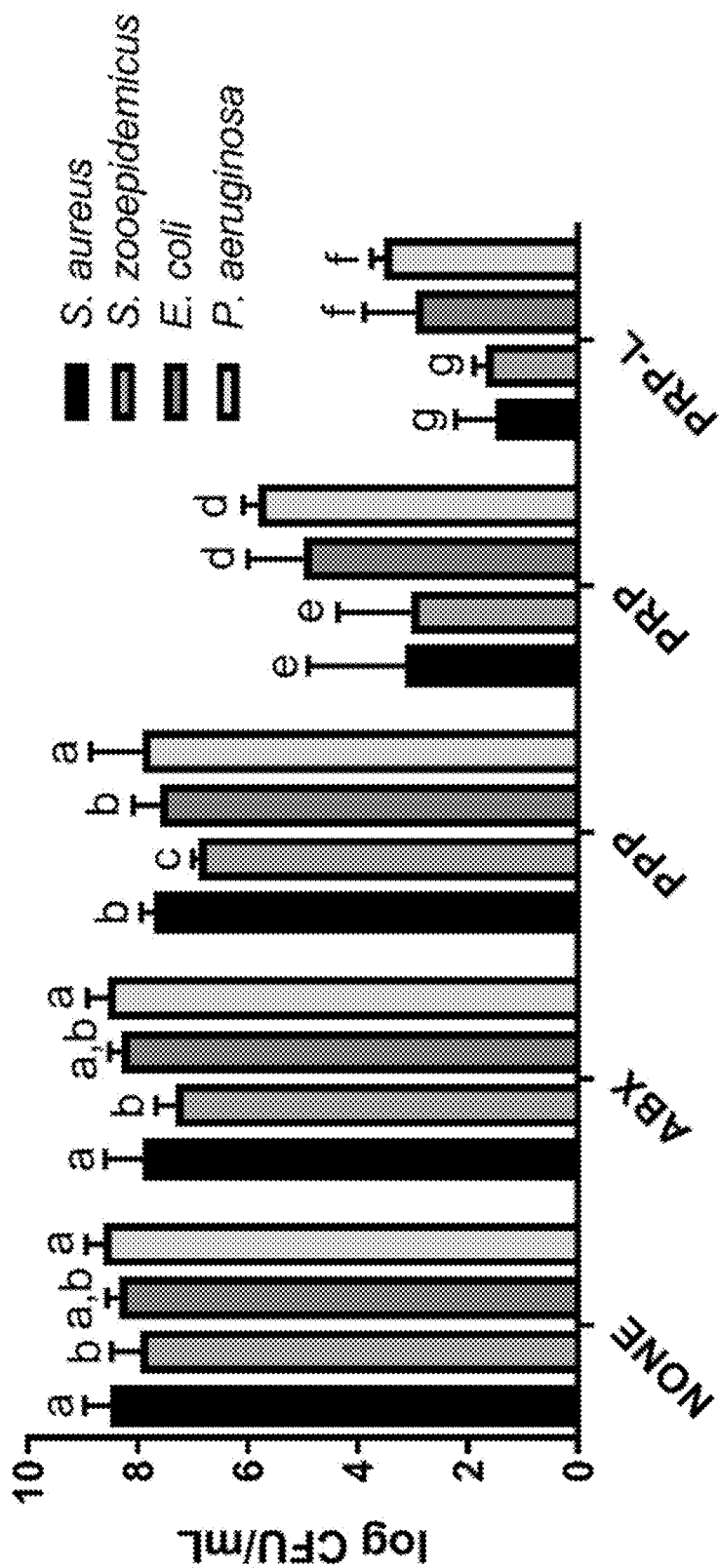
FIG. 2 is a bar graph showing efficacy of PRP and PRP-L against gram-positive and gram-negative clinical isolates that form biofloats in synovial fluid. Methodology of infection and treatment of synovial fluid was carried out as described for FIG. 1 but using four clinical isolates from equine infectious arthritis cases. Treatments were (v/v) as follows: PBS (untreated control; NONE), antimicrobial treatment with amikacin at 40 μg/mL or 10× MIC (ABX), platelet-poor plasma (PPP), 50× platelet-rich plasma (PRP) or 50× platelet-rich plasma lysate (PRP-L). Platelet formulations were generated from individual horses (n=6). Bars are means and standard deviations. Statistical analysis was performed by a 2-way ANCOVA with individual horse as a covariate and Tukey's post hoc test. Differing letters indicate statistical significance of $p<0.05$.

PRP-L is More Active Against Biofloats Formed in Synovial Fluid by Gram-Positive Than Gram-Negative Organisms We further explored whether PRP-L combats other bacterial species that form biofloats in synovial fluid besides *S. aureus*. To this end, we infected synovial fluid with the following isolates collected from clinical cases of equine infectious arthritis: *S. aureus, S. zooepidemicus, E. coli* and *P. aeruginosa*. Each isolate was grown as biofloats in synovial fluid (same method as FIGS. 1A-1C) and subsequently treated with PPP, PRP, and PRP-L. PRP-L showed anti-biofilm properties and maintained greater efficacy than PRP and PPP against all isolates evaluated (p<0.001) (FIG. 2). However, all platelet formulations were less effective against gram-negative strains than gram-positive strains (p<0.003).

EXAMPLE 3

PRP-L Increases the Sensitivity of Previously Antimicrobial Tolerant Biofloats to Aminoglycosides We tested the ability of PRP-L to increase the efficacy of aminoglycosides against tolerant biofloats in synovial fluid. PRP-L displayed synergism with the aminoglycoside, amikacin (p<0.0001) against biofloats formed by the laboratory *S. aureus* strain, ATCC 25923 (FIG. 3A). In addition, PRP-L showed a synergistic effect with the amikacin against all four clinical isolates (p<0.0001) (FIG. 3B). However, as seen in FIG. 2, gram-positive organisms were more susceptible to the combination of PRP-L and amikacin than gram-negative organisms (p<0.0003).

EXAMPLE 4

Figure 4B:
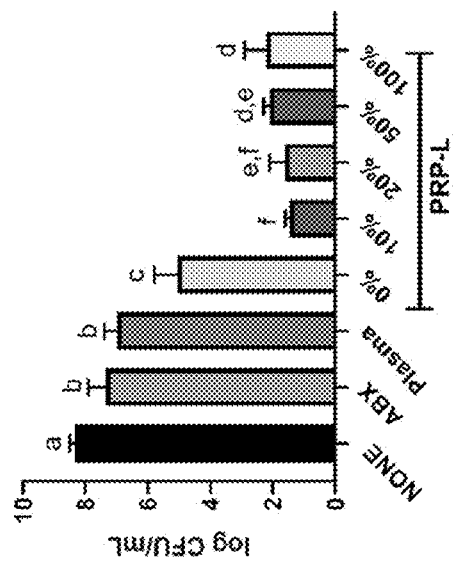
Figure 4A:
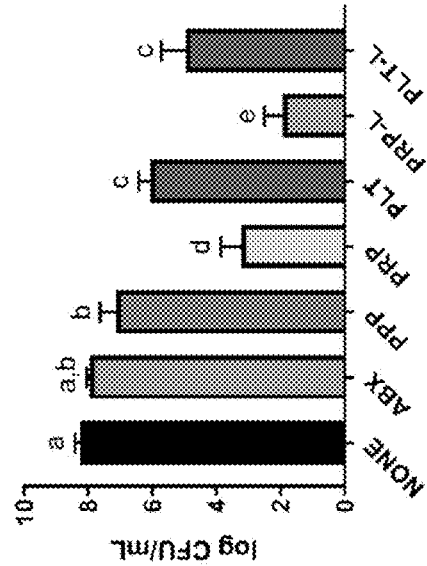

Observed Anti-Biofilm Properties of PRP are Dependent Upon a Synergism Between Platelets and Plasma We wanted to determine if the plasma component was necessary for the activity of PRP and PRP-L. We challenged bacteria in synovial fluid with platelets in plasma (PRP) or platelets in buffer (PLT) and platelets lysed in plasma (PRP-L) or platelet lysed in buffer (PLT-L). Both PLT and PLT-L were antimicrobial compared to PPP, amikacin treatment, or untreated biofloats (p<0.001) (FIG. 4A). However, PRP and PRP-L were more active than PLT and PLT-L (p<0.002 and p<0.001, respectively). We then measured the effect of different ratios of plasma and platelets within the PRP-L formulation and found that 10% plasma was more efficacious compared to 100% or 0% plasma (p <0.0001; FIG. 4B). We concluded that the combination of platelets and plasma during lysis is vital to the observed anti-biofilm activity and used 10% plasma in all following preparations.

EXAMPLE 5

Proteolytic Activity in Plasma During Lysis Plays a Role in the Anti-Biofilm Activity of PRP-L Most antimicrobial peptides are derived from proteolytic cleavage from larger precursors (Zhang L J, Gallo R L. Antimicrobial peptides. Curr Biol. Cell Press; 2016; 26: R14-R19); for example, LL-37 is processed by proteinase 3 from the larger cathelicidin (hCAP-18) (Sorensen et al., Blood. American Society of Hematology; 2001; 97: 3951-3959)). In order to determine if proteolytic activity was important to the activity of PRP-L, we added protease inhibitors to PRP prior to lysis (FIG. 4C). The PRP-L that was treated with protease inhibitors (PRP-L PI) lost significant anti-biofilm activity compared to untreated PRP-L (p<0.0001). In order to determine if the proteolytic activity was plasma derived, we heat inactivated plasma at 65° C. or 95° C. prior to platelet lysis within plasma. We found that heat inactivation of plasma decreased the anti-biofilm effects of PRP-L (FIG. 4C). We concluded that the proteolytic activity in plasma plays a role in the anti-biofilm activity of PRP-L.

EXAMPLE 6

Figure 5:
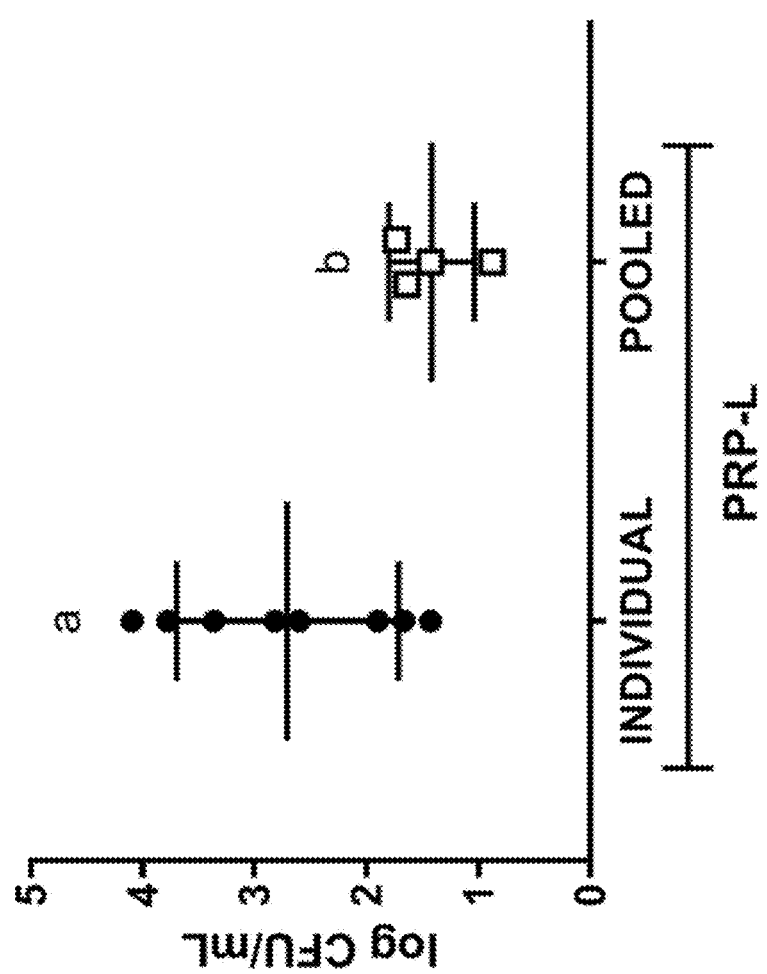
FIG. 5 is a is a plot showing increased anti-biofilm activity of pooled versus individual PRP-L. Synovial fluid was infected with *S. aureus* ATCC 25923 as previous described. (Plot A) Synovial fluid was treated with 50× PRP-L generated from individual horses (n=8, INDIVIDUAL) or (Plot B) PRP-L pooled amongst the same eight individual horses on four separate collection occasions (n=4, POOLED). Bars are means and standard deviations. Statistical analysis was performed by an unpaired t-test. Differing letters indicate statistical significance of $p<0.05$.

PRP-L Pooled From Multiple Individuals Decreases Variability and Increases the Antimicrobial Potency Use of pooled PRP-L is a common practice in the development of a serum substitute for culture of stem cells to reduce the variability observed in individual donors (Burnouf T, et al., Biomaterials. 2016; 76: 371-387; Chou M L, Burnouf T. et al., ISBT Sci Ser. 2017; 168-175). Therefore, we set out to determine if pooled PRP-L would be more efficacious than PRP-L from individual horses. Pooled PRP-L (pPRP-L) was generated from 8 horses pooled on four separate occasions and decreased bacterial load to a greater extent than PRP-L from individual horses (p<0.03) (FIG. 5). Pooled PRP-L was used in all following preparations.

EXAMPLE 7

Figure 6:
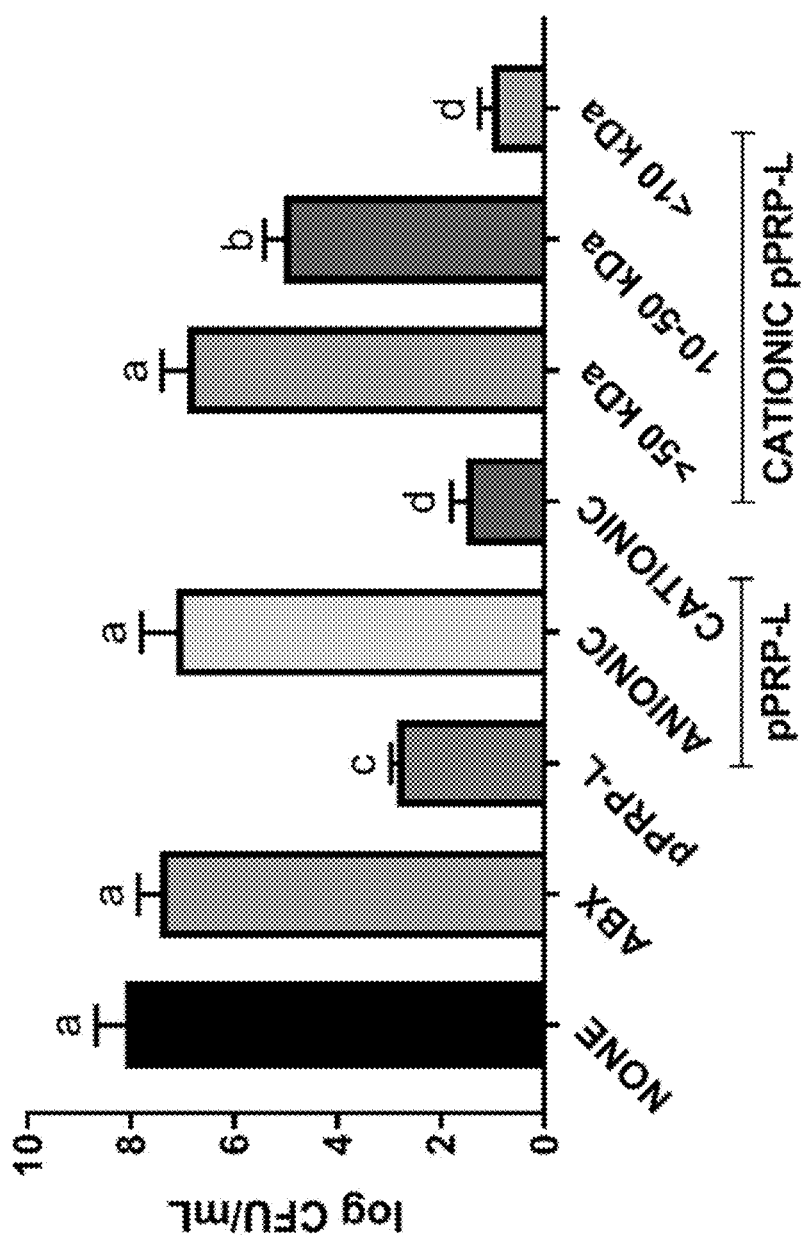
FIG. 6 is a bar graph showing crude protein fractionation of pooled PRP-L (pPRP-L) to determine the active anti-biofilm components. 50× pPRP-L was fractionated into its respective anionic and cationic components using ion exchange. The cationic fraction was subsequently passed consecutively through molecular weight filters (cutoffs 50 kDa and 10 kDa). The retentate of each passage was collected and the flow thru was placed on the next filter until 10 kDa from which the flow thru was recovered. Each fraction was tested for its anti-biofilm activity against synovial fluid infected with *S. aureus* ATCC 25923. Bars are means and standard deviations. Statistical analysis was performed by a 1-way ANOVA with Tukey's post hoc test. Differing letters indicate statistical significance of $p<0.05$.

The Bioactive Components of Pooled PRP-L are Cationic and Low Molecular Weight We hypothesized that the bioactivity of PRP-L was due antimicrobial peptides which are small (<10 kDa) and cationic (Tang Y-Q, et al., Infect Immun. 2002; 70: 6524-33). In order to test this hypothesis, we fractionated pPRP-L into its anionic and cationic components using ion exchange resin and tested each fraction for anti-biofilm properties. We found that the cationic fraction of pPRP-L was significantly more active than the anionic fraction (p<0.0001) and that the cationic fraction was more active than the parent pPRP-L (p<0.008) (FIG. 6). We then used centrifugation filters (50 kDa and 10 kDa) in sequential order to divide the cationic pPRP-L components into high, medium and low molecular weight fractions. From there we determined that the <10 kDa or low molecular weight enriched fraction had higher similar anti-biofilm activity than its parent cationic pPRP-L fraction (FIG. 6).

EXAMPLE 8

Figure 7:
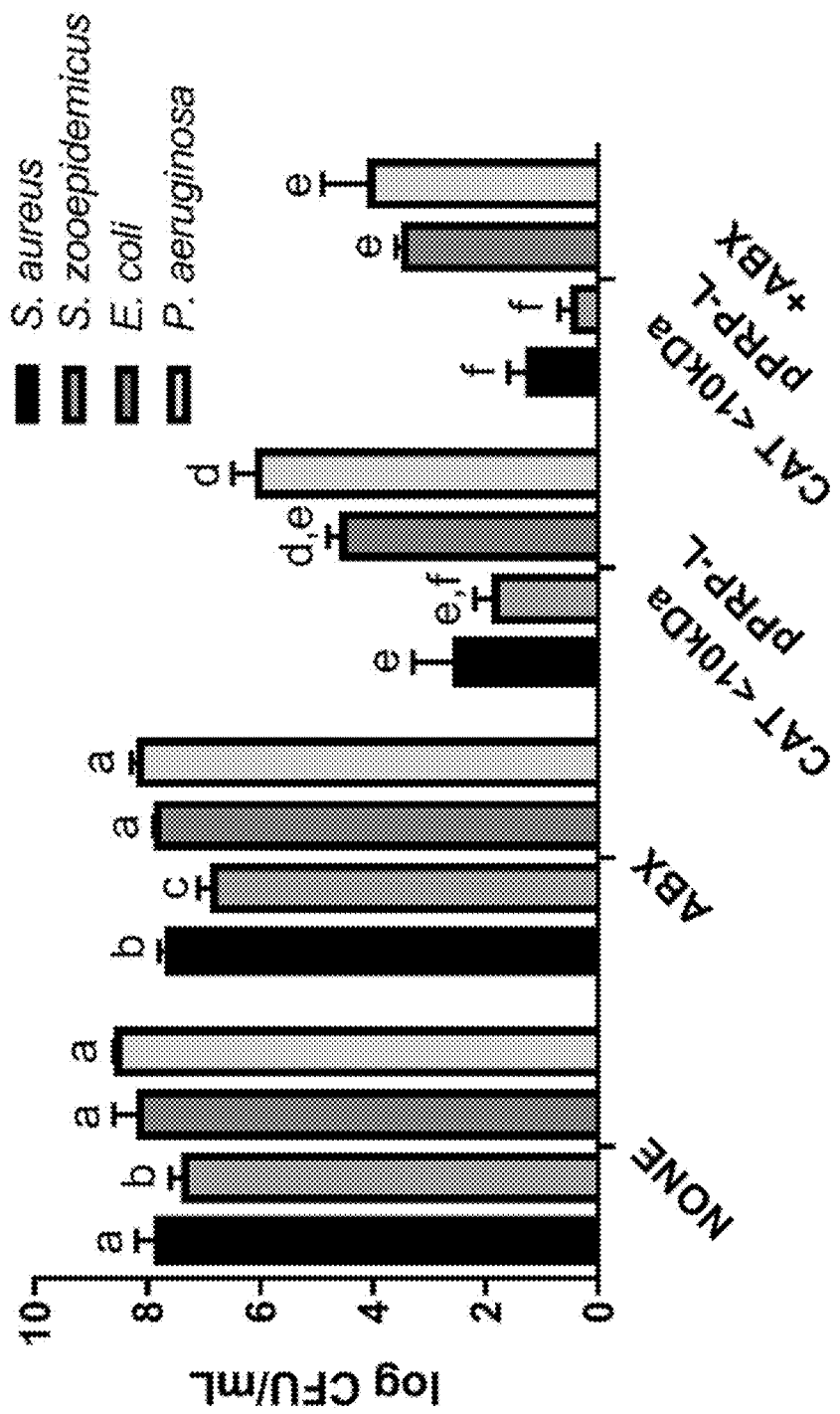
FIG. 7 is a bar graph showing efficacy of fractionated cationic, low-molecular weight pPRP-L and synergism with aminoglycosides against gram-positive and gram-negative biofloats. Methodology of infection and treatment of synovial fluid was carried out as previously described using the four clinical isolates from equine septic arthritis cases. Treatments were (v/v) as follows: PBS (untreated control; NONE), cationic low-molecular weight fractionated pooled 50× PRP-L (CAT, <10 kDa pPRP-L) alone or in combination with antimicrobial treatment with amikacin at 10× MIC (ABX). Bars are means and standard deviations. Statistical analysis was performed by a 2-way ANCOVA with individual bacterial isolate as a covariate and Tukey's post hoc test. Differing letters indicate statistical significance of $p<0.05$.

The Cationic, Low Molecular Weight Pooled PRP-L is Antimicrobial and Synergistic With Aminoglycosides Against Both Gram-Negative and Gram-Positive Species We wanted to ensure that the fractionated pPRP-L from FIG. 6 maintains activity and synergism with aminoglycosides against the clinical isolates that form biofloats in synovial fluid. We found that the cationic, low-molecular weight pPRP-L has anti-biofilm properties against all clinical isolates (p<0.02) (FIG. 7). However, as for PRP-L shown in FIG. 2, it was more active against gram-positive biofloats than gram-negative biofloats (p<0.05). We also showed that the fractionated pPRP-L maintained synergism with amikacin (p<0.03), albeit more so against gram-positive biofloats (p<0.02) (FIG. 7).

EXAMPLE 9

S. aureus Within Synovial Fluid Biofloats Induced Extracellular Trap Formation by Neutrophils That Can be Reversed by the Addition of BIO-PLY S. aureus (ATCC® 25923) was grown as a single cell suspension (planktonic) in RMPI or as aggregates in synovial fluid (biofloat) for 3 hours. Neutrophils were isolated from healthy horses and incubated with each bacterial phenotype for 4 hours at a MOI of 10:1 with or without the addition of BIO-PLY at sub-antimicrobial concentrations. Referring to FIG. 8A, NET formation was quantified by the addition of 5 µM of the cell impermeable DNA binding dye (SYTOX® Green Nucleic Acid Stain, ThermoFisher Scientific Waltham, Mass.) for 10 minutes before fluorescence was measured with area scan settings on a microtiter plate reader. Referring to FIG. 8B, immunofluorescent labeling (scale bar 20 µM) was performed using fluorescent stained S. aureus (green), anti-CitH3 (red) (NETs) and DAPI (PMN nuclei; blue). Referring to FIG. 8C, higher magnification of the immunofluorescent labeling (scale bar 10 µM). Data is shown as the mean±standard deviation of n=3. Differing letters indicate significant differences between groups (p<0.05); statistical analysis was performed by one-way ANCOVA with Tukey post-hoc and individual horse as the covariate.

EXAMPLE 10

Bacteria Within Biofloats Decreased Neutrophil Antibacterial Function

Figures 9A, 9B, 9C:
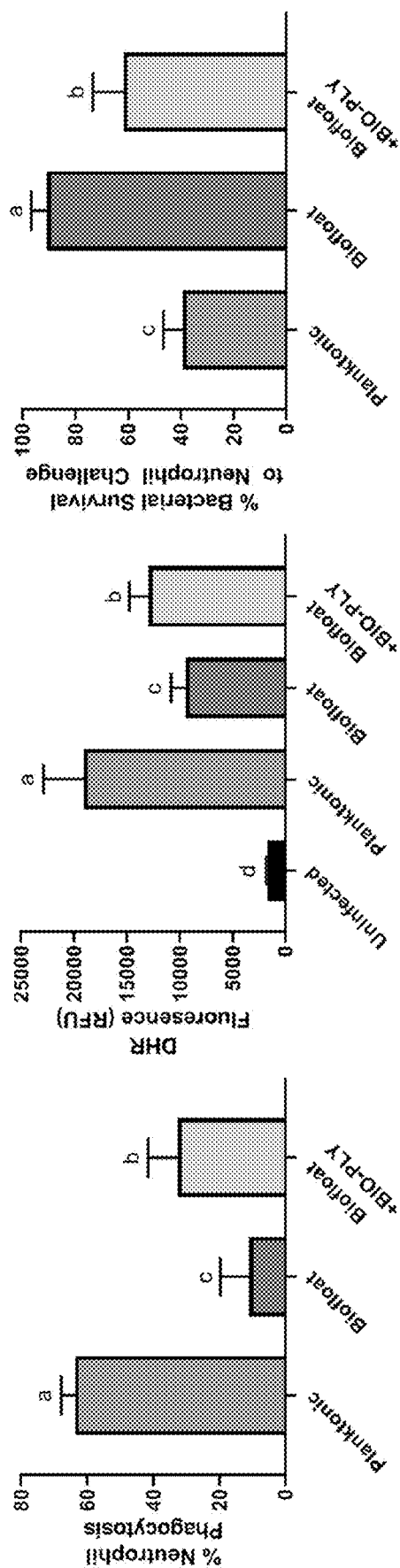
FIGS. 9A through 9C are bar graphs showing BIO-PLY treatment increased neutrophil phagocytosis and respiratory burst thereby increasing neutrophil antibacterial function against biofloats. Infections and treatments were carried out as in FIG. 1.

Neutrophils displayed decreased phagocytosis (p<0.0002; FIG. 9A) and subsequent respiratory burst (p<0.004; FIG. 9B) in response to bacteria within biofloats compared to planktonic bacteria. The increased NET formation and decreased phagocytosis resulted in higher survival of bacteria with biofloats compared to planktonic bacteria (p<0.0001; FIG. 9C).

EXAMPLE 11

BIO-PLY Treatment Shifted Neutrophil Responses to Bacteria Within Biofloats

Concurrent treatment of neutrophils with BIO-PLY during challenge with biofloats results in decreased NET formation (p<0.03;FIG. 8A), increased phagocytosis (p<0.008; FIG. 9A) and respiratory burst (p<0.05; FIG. 9B). Imaging of neutrophils showed subjectively less neutrophils positive for anti-CitH3 (FIG. 8B); also, larger biofloats displayed subjectively less anti-CitH3 incorporated within the mass of bacteria (FIG. 8C). The altered response induced by BIO-PLY resulted in decreased survival of bacteria within biofloats (p<0.003; FIG. 9C). As BIO-PLY was used a sub-antimicrobial concentration, the decreased bacterial load observed in FIG. 9C is due to increased neutrophil antibacterial function versus direct killing of bacteria within biofloats by BIO-PLY. This was verified by determining bacterial load of biofloats treated with the same concentration of BIO-PLY without neutrophils.

EXAMPLE 12

Bacteria Within Biofloats Had a Greater Impact on Chondrocyte Viability

Synoviocyte-chondrocyte co-cultures challenged with biofloats or planktonic bacteria resulted in decreased viability of both chondrocytes and synoviocytes by 24 hours post-infection (p<0.03; FIGS. 10A, 10B, 10C, and 10D); although biofloats decreased chondrocyte viability (p<0.002; FIGS. 10C and 10D) to a greater degree than synoviocytes compared to planktonic bacteria that had a greater impact on synoviocyte viability (p<0.005; FIGS. 10A and 10B).

EXAMPLE 13

Biofloats Altered Pro-Inflammatory and Catabolic Enzyme Gene Expression in Synoviocytes Planktonic bacteria produced high gene expression of IL-1β (p<0.02; FIG. 11A) in synoviocytes but bacteria within biofloats resulted in higher levels of MMP-13 (p<0.003;FIG. 11C). Levels of MMP-3 were similar between biofloats and planktonic bacteria (FIG. 11B).

EXAMPLE 14

Biofloat Infection Resulted in a More Dramatic Shift in Collagen Gene Expression Bacteria within biofloats higher collagen type 1 (p<0.03; FIG. 12A) and lower collagen type II (p<0.04; FIG. 12B) gene expression than planktonic bacteria. This shift resulted in a lower COL2:COL1 ratio by bacteria in a biofloat versus a planktonic phenotype (p<0.05; FIG. 12C).

EXAMPLE 15

BIO-PLY Treatment Decreased Inflammation in Synoviocytes and Restored Chondrocyte Function in Co-Cultures Infected With Biofloats BIO-PLY treatment of co-cultures infected with biofloats resulted in increased synoviocyte (p<0.03; FIGS. 10A and 10B) and chondrocyte viability (p<0.008; FIGS. 10C and 10D). A lower trend in MMP-13 gene expression was appreciated with BIO-PLY treatment (p<0.1; FIG. 11C); however, no differences were appreciated in IL-1β and MMP-3 gene expression by BIO-PLY treatment. BIO-PLY treatment decreased collagen type I (p<0.04; FIG. 12A) and increased collagen type II (p<0.02; FIG. 12B) gene expression resulting in an improved COL2:COL1 ratio (p<0.006; FIG. 12C).

EXAMPLE 16

BIO-PLY Treatment Reduced Clinical Signs of Infection

Referring to FIG. 13A, each horse was evaluated and scored for clinical signs of infection (pain score) on a scale of 0-3 (0=most normal, 3=most abnormal): lameness, tarsocrural swelling, distal limb edema, pain to palpation of the joint, and heat at the site of infection. Pain scores were lower for treatment horses from days 3-7, 14 and 21.

Figure 13C:
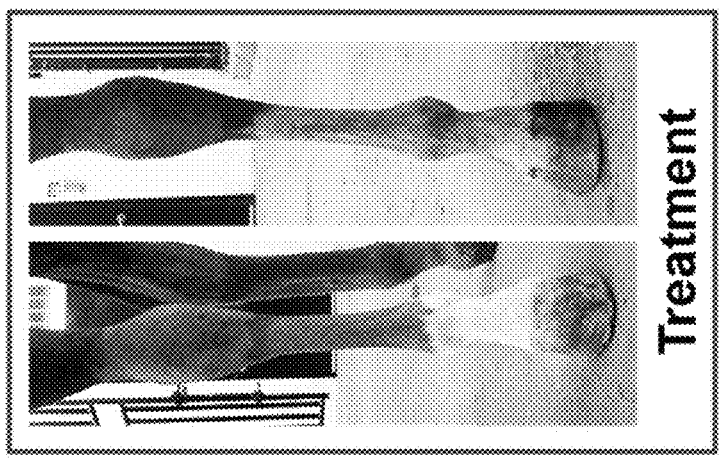
FIGS. 13A through 13C are a line graph and two photographic images showing BIO-PLY treatment reduced clinical signs of infection.
Figure 13B:
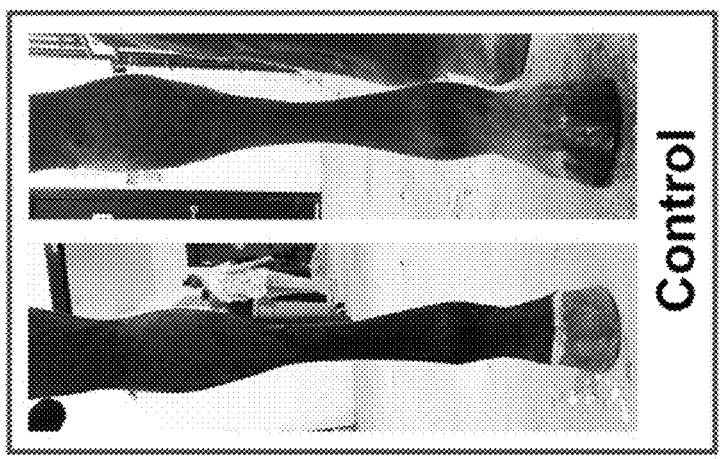
Figure 13A:
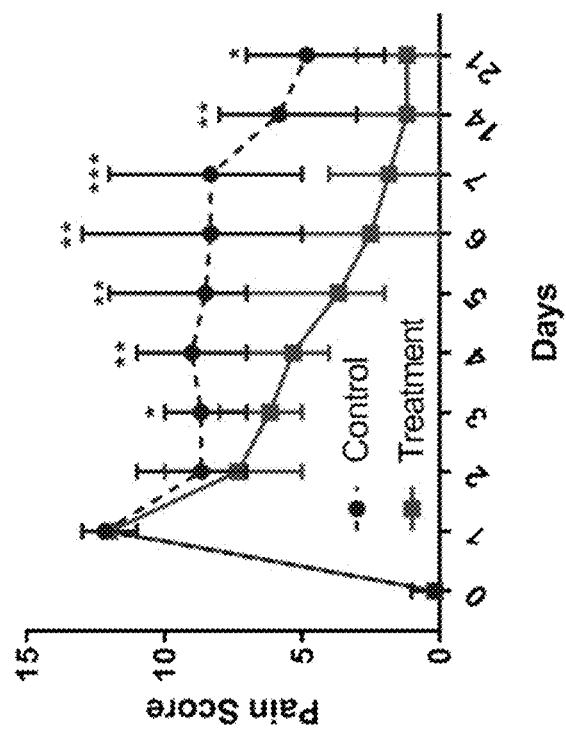

Referring to FIGS. 13B and 13C, experimental limbs were photographed at day 7 and a notable reduction in joint and distal limb effusion was appreciated in treatment horses (FIG. 13C) compared to control horses (FIG. 13B). Means and standard deviations of each group (control vs treatment; n=6), and significant differences *$p<0.05$ $p<0.01$ *$p<0.001$ ****$p<0.0001$ were determined by the Wilcoxon rank-sum test comparing control and treatment at each day (0-7, 14, and 21).

EXAMPLE 17

BIO-PLY Treated Horses Had Lower Levels of Systemic Inflammatory Markers

Systemic fibrinogen was significantly lower in BIO-PLY treated horses at days 2-3, 6-7, and 21 ($p<0.0003$; FIG. 14A) as was D-dimer concentration at days 3-7, 14 and 21 ($p<0.001$; FIG. 14B). Serum amyloid A concentrations were not significantly different between BIO-PLY treated and control horses (FIG. 14C).

EXAMPLE 18

BIO-PLY Treatment Altered Local Inflammatory Patterns

Synovial fluid samples were obtained from all horses at sufficient volume for analyses from days 0-7. Although no differences in synovial fluid TNCC or TP were appreciated between treated and control horses (FIGS. 15A and 15B), BIO-PLY treated horses had a lower percentage of neutrophils ($p<0.02$; FIG. 15C) and higher percentage of mononuclear cells ($p<0.01$; FIG. 15D) at day 7 compared to control horses.

EXAMPLE 19

BIO-PLY Treated Horses Had Improved Ultrasonographic Appearance

Figure 16C:
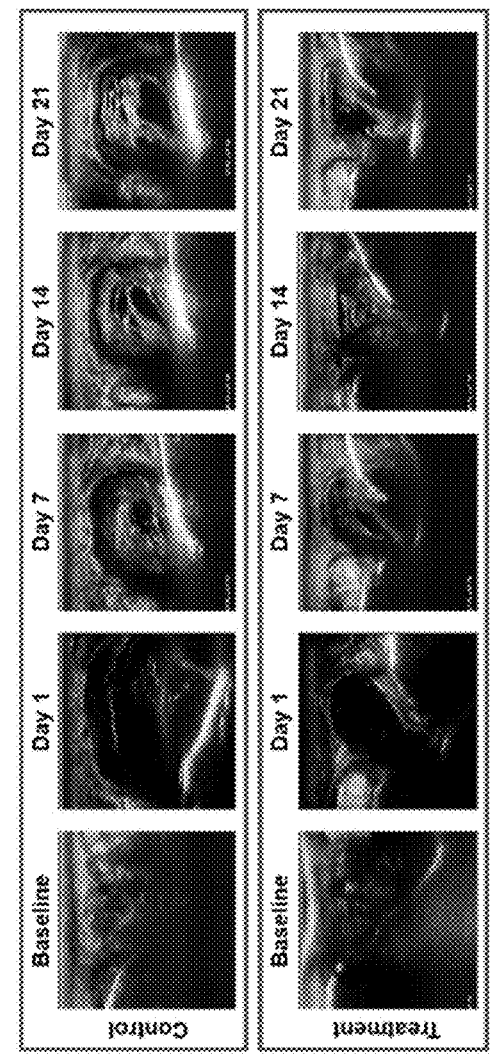
Figure 16A:
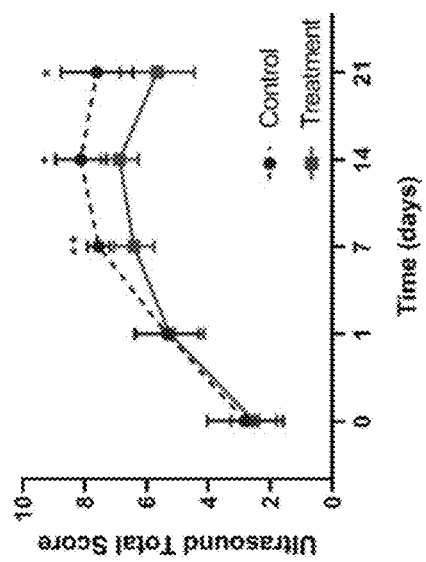

Horses treated with BIO-PLY had improved ultrasonographic scores compared to control horses (FIG. 16A). At both the dorsomedial (FIG. 16B) and plantolateral (FIG. 16C) location, BIO-PLY treatment resulted in improved ultrasonographic appearance. More specifically, BIO-PLY treatment resulted in less intracapsular hyperechoic lobular and striated material, that would be best described as fibrinous material, with an increased fluid component at day 7, 14 and 21. At day 14, the degree of joint distension has improved with BIO-PLY treatment. At day 21, the thickness of the joint capsule and synovial thickening is improved with BIO-PLY treatment. These observations were more evident at the dorsomedial location (FIG. 16B) compared to the plantolateral location (FIG. 16C).

EXAMPLE 20

BIO-PLY Treatment Shifted Synovial Fluid Cytokine Concentrations

Treatment with BIO-PLY resulted in altered cytokine concentration in the synovial fluid. BIO-PLY treatment decreased IL-1β at days 3-7 ($p<0.02$; FIG. 17A), IL-6 at day 7 ($p<0.05$; FIG. 17B), TNFα at day 5 ($p<0.04$; FIG. 17C), IL-8 at days 2-7 ($p<0.03$; FIG. 17D), MCP-1 at days 4-7 ($p<0.03$; FIG. 17E), G-CSF at days 2-7 ($p<0.04$; FIG. 17F), IL-18 at days 2-7 ($p<0.001$; FIG. 17G), IL-4 at days 2-7 ($p<0.0008$; FIG. 17H), IL-5 at days 2-7 ($p<0.02$; FIG. 17I), IL-10 at days 4-7 ($p<0.04$; FIG. 11J), and IL-2 at days 4-5 ($p<0.03$; FIG. 17K). IFNγ was increased in BIO-PLY treated horses at day 2 but decreased in BIO-PLY treated horses at days 6-7 ($p<0.04$; FIG. 17L). BIO-PLY treatment did not alter synovial fluid concentrations of FGF2 (FIG. 18A), eotaxin (FIG. 18B), GM-CSF (FIG. 18C), IL-1α (FIG. 18D), fractalkine (FIG. 18E), IL-13 (FIG. 18F), IL-17A (FIG. 18G), IL-12p70 (FIG. 18H), IP-10 (FIG. 18I), or GRO (FIG. 18J).

EXAMPLE 21

Treatment With BIO-PLY Decreased Bacterial Load in Synovial Fluid and Tissue All horses had obvious biofloats at day 1 (post-infection/pre-treatment) (FIG. 19A). BIO-PLY treated horses had significantly lower concentrations of bacteria in synovial fluid at days 3-7 ($p<0.006$; FIG. 19B) and significantly less bacteria within the synovial tissue at end-term (2.06±4.86 CFU/g tissue) compared to horses treated with amikacin alone (80.95±58.77 CFU/g tissue) ($p<0.009$; FIG. 19C).

EXAMPLE 22

BIO-PLY Treatment Exhibited Chondroprotective Effects

The cartilage from horses treated with BIO-PLY (FIG. 20) had improved Safranin-O staining compared to control horses indicating increased proteoglycan content within the cartilage.

EXAMPLE 23

BIO-PLY Treatment Altered Synovial Tissue Inflammation and Fibrosis

Treatment with BIO-PLY decreased erosion and fibrinous exudate (arrow for treatment, double headed arrow for control) along the intimal layer of the synovium (FIG. 21A). In addition, treatment with BIO-PLY decreased the extent of granulation tissue in the subintimal layer of the synovium (indicated by the arrow heads). Treatment with BIO-PLY caused clustering of T and B cells (CD3+ and CD20+ respectively) compared to diffuse staining of T and B cells in control horses (FIG. 21B). BIO-PLY treated horses had a higher ratio of macrophage type 1 (M1, MAC387+) to macrophage type 2 (M2, CD204+) infiltrate compared to control horses (FIG. 21C).

Histologically, joint infections are characterized by synovial inflammation with surface erosions and fibrinosuppurative exudates, subintimal infiltration by neutrophils and mononuclear cells, granulation tissue proliferation and fibrosis (C. J. Della Valle, et al., J. Bone Joint Surg. Am. 81, 684-9 (1999)). Bacteria were not identified on Brown and Brenn-stained sections in either BIO-PLY treated or control joints. Horses treated with BIO-PLY had lower (ie improved) total scores for synovial lesions based upon the OARSI scoring system for horses (C. W. McIlwraith, et al., Osteoarthr. Cartil. 18, S93-S105 (2010)) ($p<0.04$) (FIGS.

Figure 22A:
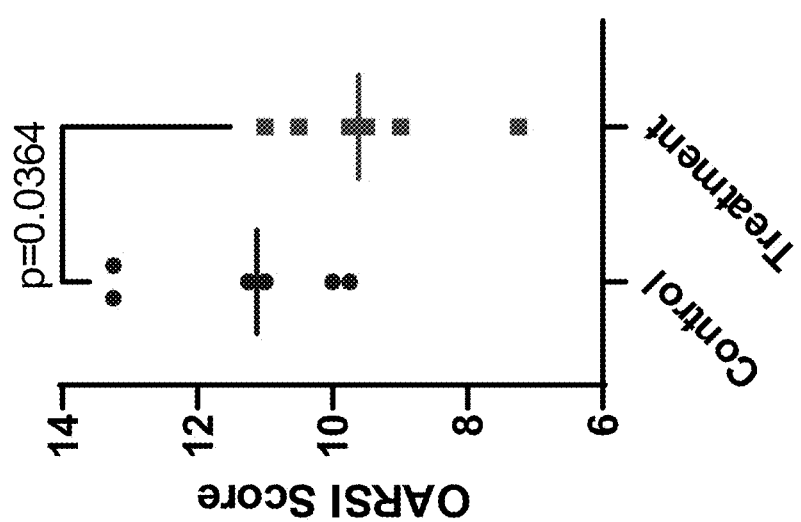
FIGS. 22A and 22B shown synovium OARSI (Osteoarthritis Research Society International) scores were lower in BIO-PLY treated horses. The OARSI system comprises a grading and a staging component, a higher grade indicates a more aggressive biologic progression and a higher stage indicates a wider disease extent. A particular feature of the OARSI system is the ability to identify differences within early or mild OA. Synovial samples from four different regions of the joint were evaluated for synovial membrane changes using the OARSI scoring system.
Figure 22B:
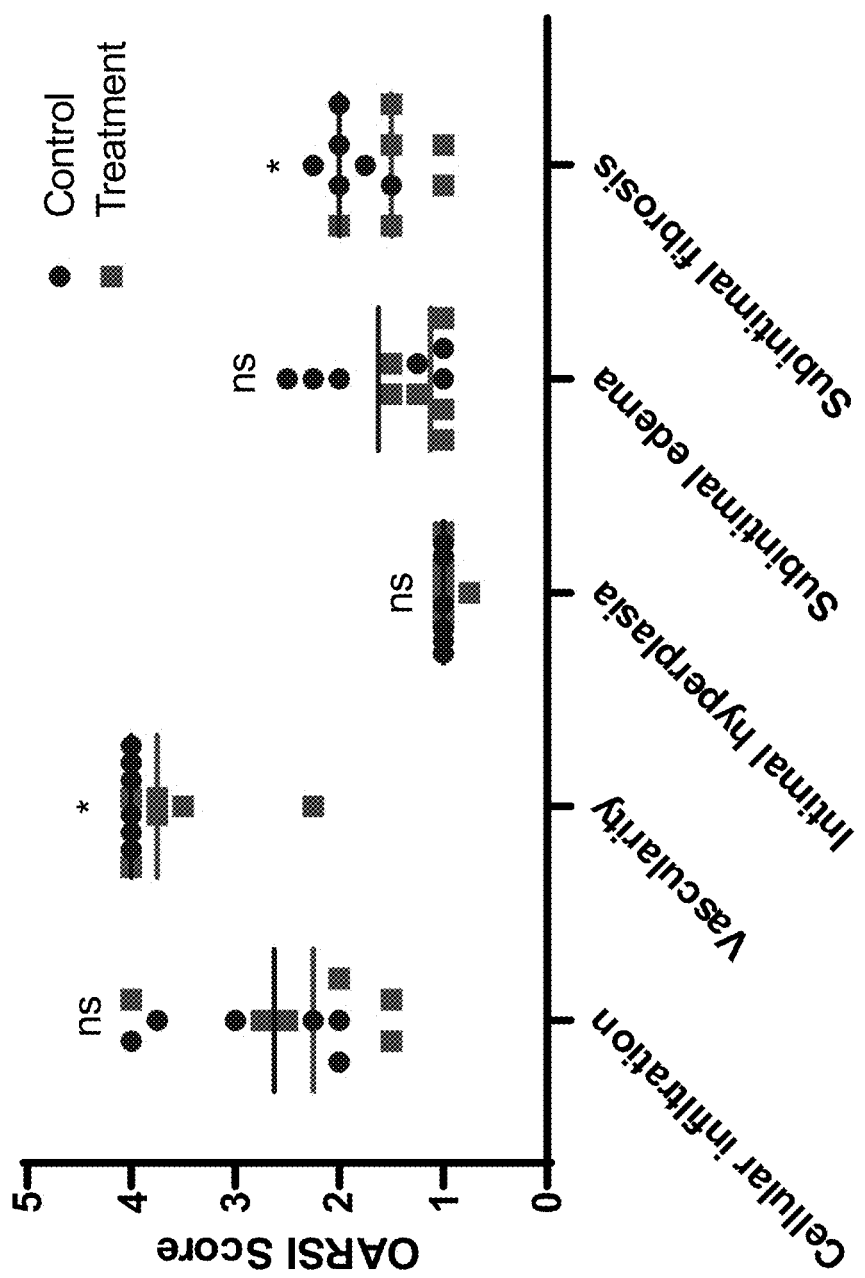
Figure 24A:
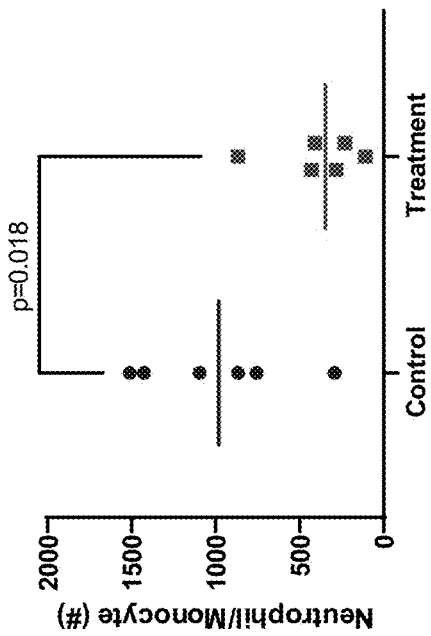
FIGS. 24A through FIGS. 24H display BIO-PLY treatment altered inflammatory cell infiltrates. Sections of synovium stained with immunohistochemical stains were evaluated for the absolute number and percentage of different inflammatory cell types including (FIGS. 24A/24B) calprotectin/S100A8/A9 (neutrophil antibody), (FIGS. 24C/24D) CD20 (B cell antibody), (FIGS. 24E/24F) CD204 (macrophage/dendritic cell antibody) and (FIGS. 24G/24H) CD3 (T cell antibody). Horses treated with BIO-PLY had lower numbers or decreased percentage of neutrophils and a higher number and increased percentage of B lymphocytes within the synovial tissue compared to control horses.
Figure 24B:
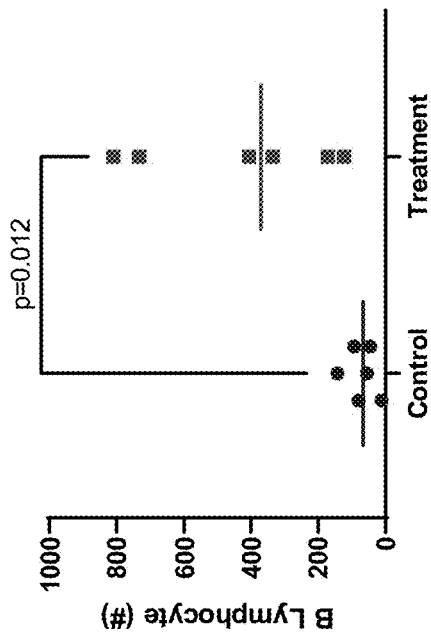
Figure 24C:
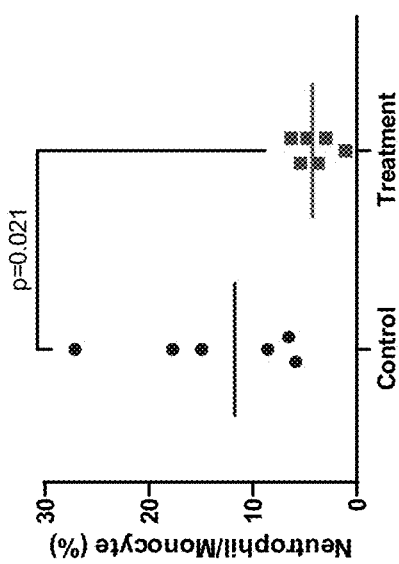
Figure 24D:
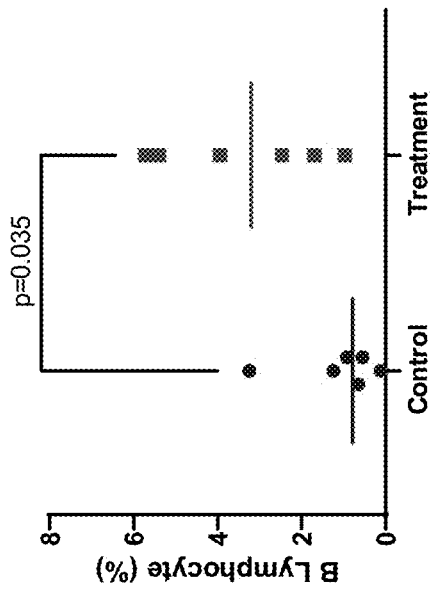
Figure 24E:
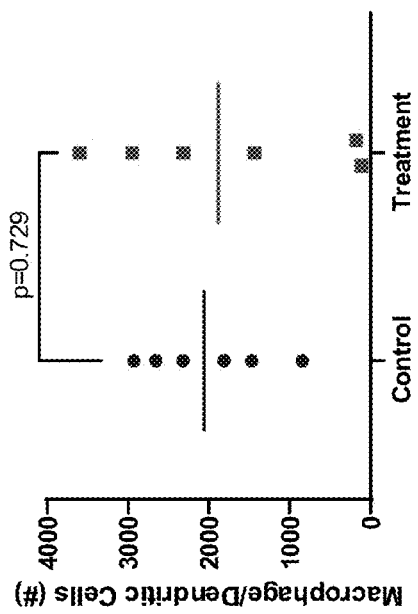
Figure 24F:
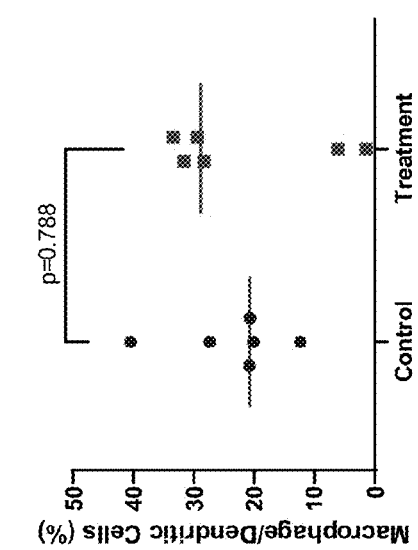
Figure 24G:
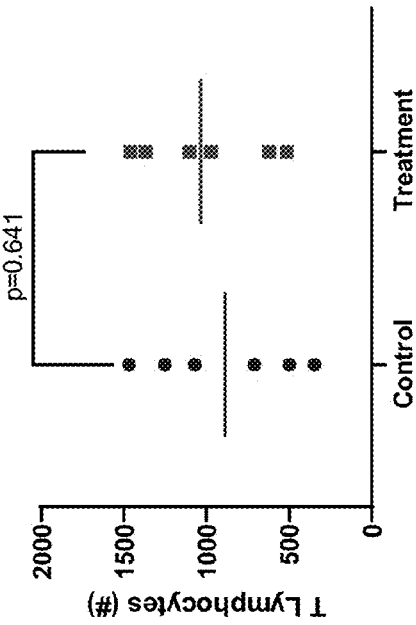
Figure 24H:
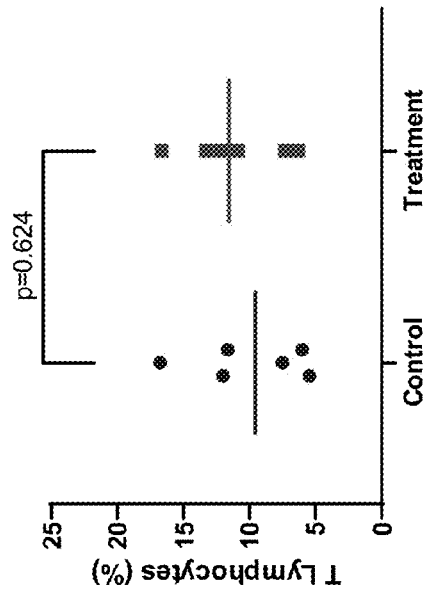

22A and 22B, 23A-23F). Specifically, when individual components of the grading scheme were compared between groups, BIO-PLY treated joints has significantly lower scores for both, vascularity and subintimal fibrosis (p<0.04) (FIG. 22B), even though other components (i.e. cellular infiltration, subintimal edema) also trended lower for BIO-PLY treated joints. Although not a component of the OARSI scheme, horses treated with BIO-PLY also showed decreased number and extent of intimal ulcers and accumulations of fibrinous exudate as compared to controls (FIG. 23A-23D). Because the OARSI scoring system does not further characterize inflammatory cell infiltrates, and because of the trend for reduced cell infiltrates (FIG. 22B) in conjunction with reduced molecular markers of inflammation in BIO-PLY treated joints (FIGS. 17A-17I), we used immunohistochemistry (IHC) to better characterize inflammatory cell populations within each synovial tissue sample (FIGS. 24A-24H, 25A-25D). Notably, BIO-PLY treated synovium had a lower numbers and percentage S100A9+ myeloid leukocytes (predominantly segmented neutrophils), in all layers of synovium, especially concentrated in the superficial intima and fibrinous exudates (p<0.03) (FIGS. 24A, 25A, 25B). In addition, BIO-PLY treated synovium had increased numbers and percentage of B-lymphocytes (CD20+) within the superficial synovial layers as compared to controls (p<0.04) (FIGS. 24B, 25C, 25D). No differences in numbers, percentage or distribution of either CD204+ cells (i.e. dendritic cells and macrophages) or CD3+ T-lymphocytes were identified between the BIO-PLY treated and control groups (FIGS. 24C, 24D, 25A, 25B-insets).

EXAMPLE 24

BIO-PLY Treatment Exhibited Chondroprotective Effects

Figure 26A:
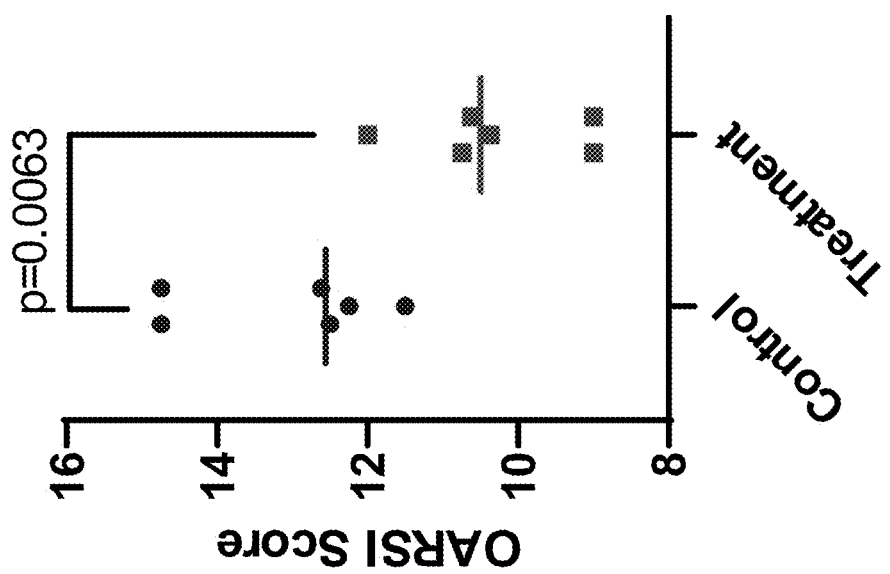
FIGS. 26A and 26B show osteochondral OARSI scores were lower in BIO-PLY treated horses. H&E stained, formic-acid decalcified osteochondral sections explanted from four sites within the tarsocrural joints of treated and control horses were evaluated for arthritic changes using the OARSI scoring system. See FIG. 20.
Figure 26B:
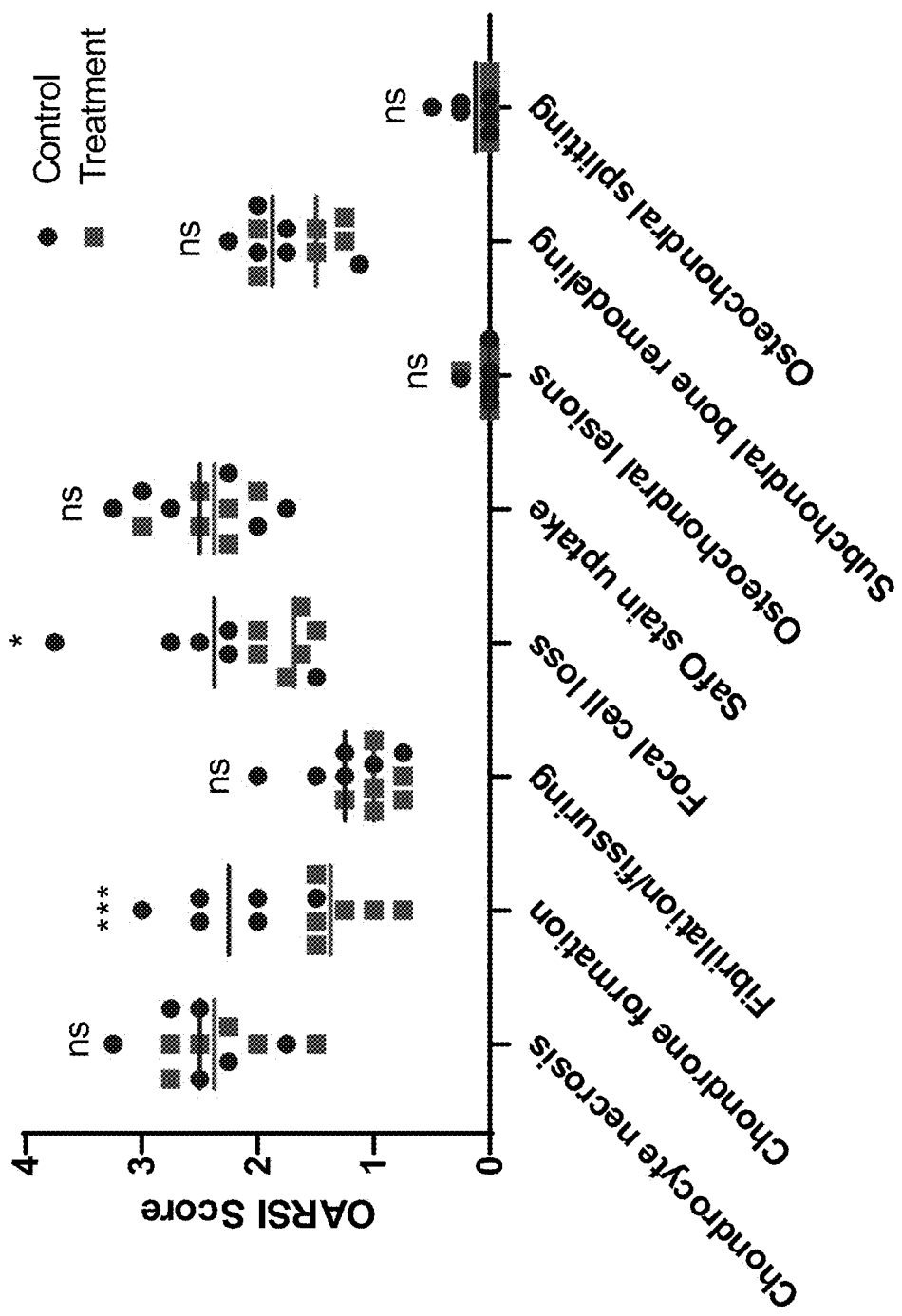
Figure 27B:
FIGS. 27A through 27D show osteochondral OARSI scores show reduced cell depletion and chondrones in BIO-PLY treated horses. High (20×) magnification H&E (FIGS. 27A-27C) and Safranin-O (Safranin O Staining/Basic Red 2) (FIG. 27D) stained photomicrographs that show articular cartilage from BIO-PLY treated horses (FIG. 27A) has a more uniform density of viable chondrocytes with rare chondrones having no more than 2 nuclei per lacuna. In contrast, articular cartilage from control has extracellular matrix with relatively increased cell loss (FIG. 27B, arrowheads) and frequent chondrones having greater that 4 nuclei per lacuna (arrows, FIG. 27C) frequently corresponding to regions of Safranin O (i.e. proteoglycan) staining depletion (FIG. 27D, arrows) within the extracellular matrix.
Figure 27D:
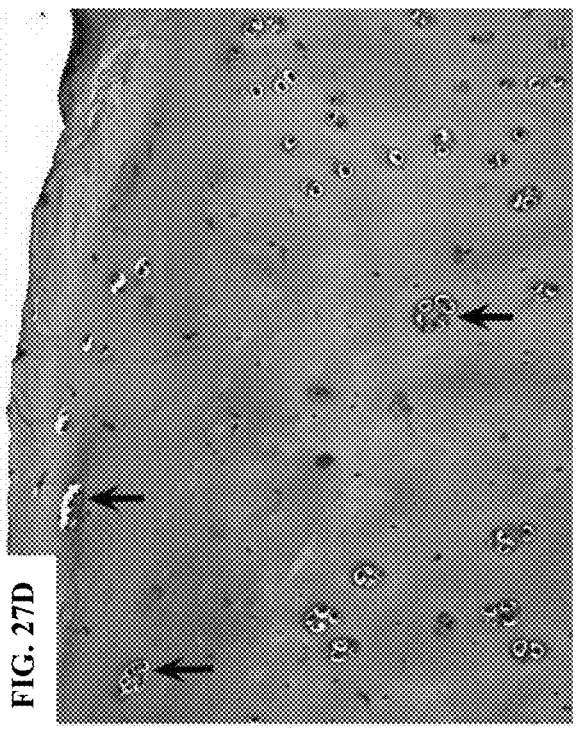
Figure 27A:
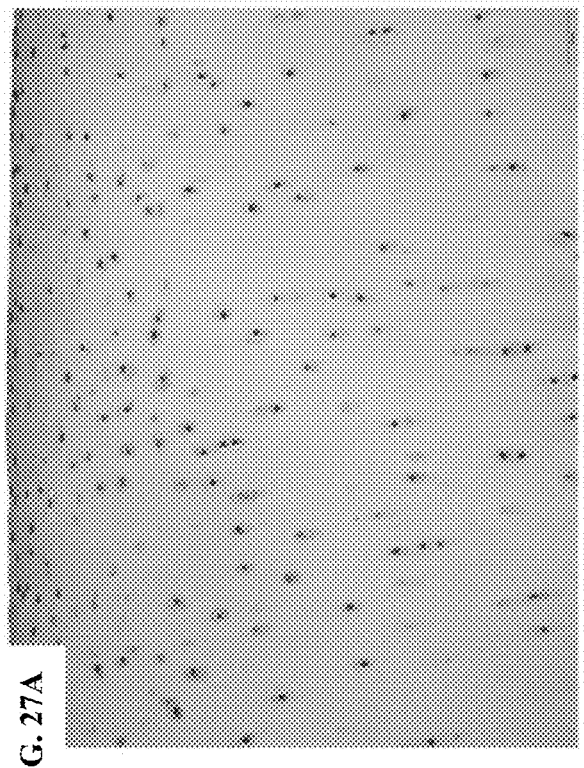
Figure 27C:
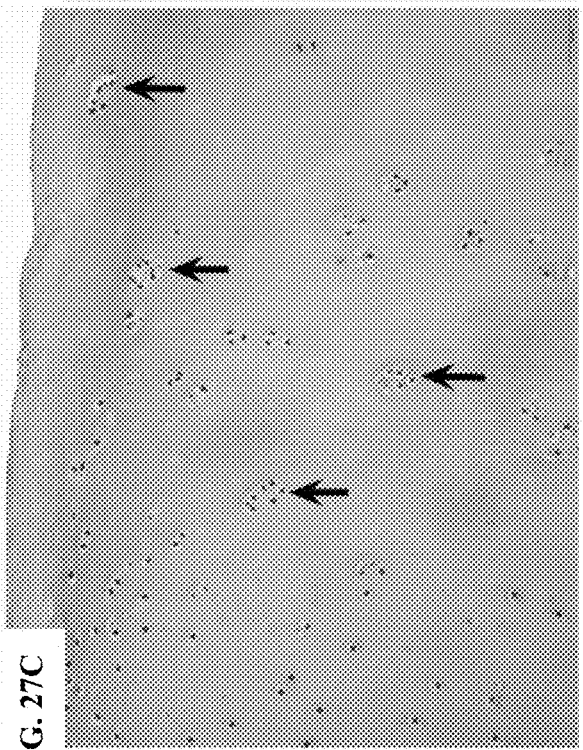
Figure 28A:
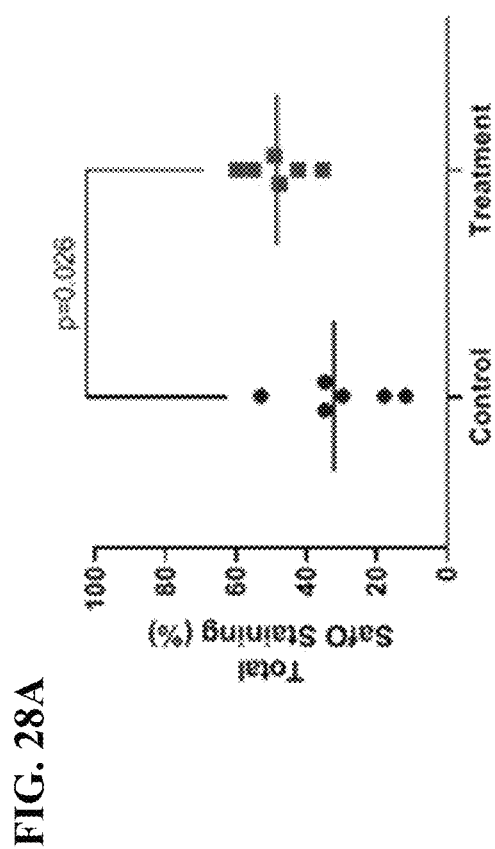
FIGS. 28A through 28E show BIO-PLY treatment protected cartilage from proteoglycan loss. Means and standard deviations of each group (control vs treatment; n=6), and significant differences *p<0.05 p<0.01 *p<0.001 ****p<0.0001 were determined by the paired t-tests comparing control and treatment at each day (0-7) and at end-term.
Figure 28B:
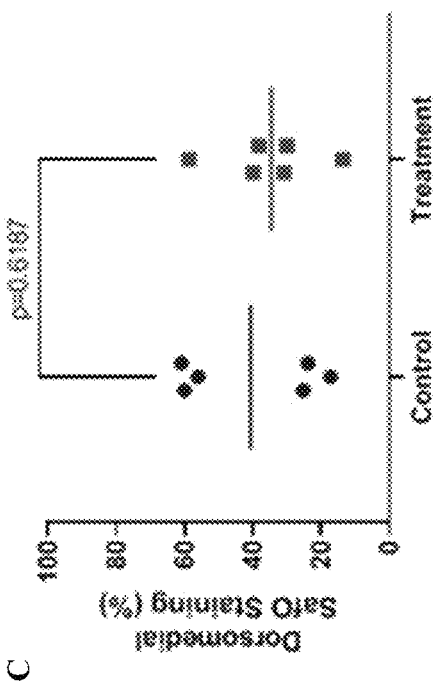
Figure 28C:
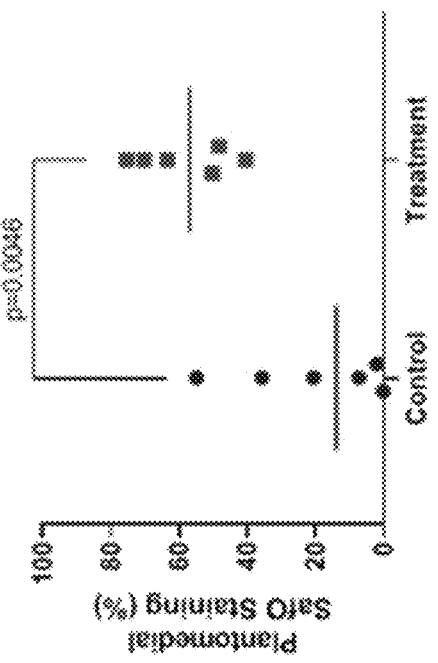
Figure 28D:
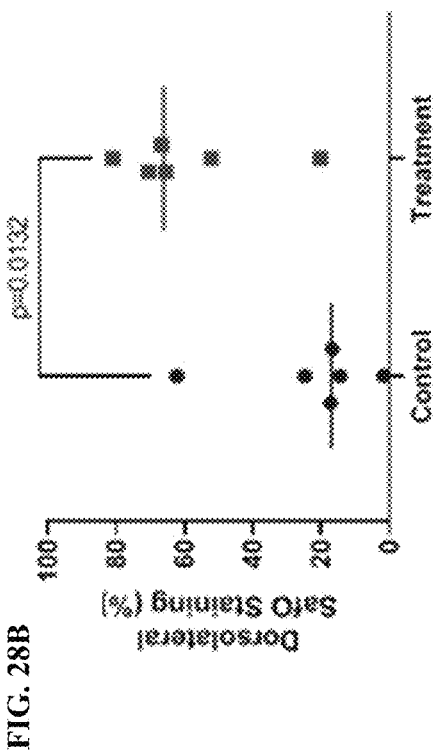
Figure 28E:
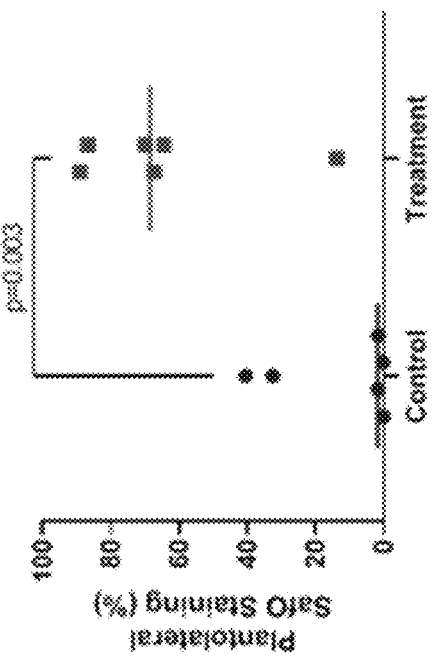

Bacterial infiltration into a joint leads to increased inflammatory markers that can result in the production of metalloproteases and other catabolic enzymes (T. N. Trumble, et al., Am. J. Vet. Res. 62, 1467-1477 (2001); J. Kidd et al., Vet. Rec. 161, 329-334 (2007); S. Sutton, et al., Vet. J. 179, 10-24 (2009); S. Spiers, et al, Equine Vet. J. 26, 48-50 (1994)). The end result of these inflammatory processes are increased degenerative (arthritic) changes comprising the cartilage extracellular matrix, chondrocytes and subchondral bone (A. J. Morton, Vet. Clin. North Am.—Equine Pract. 21, 627-649 (2005); R. J. Rose, D. N. Love, Equine Vet. J. 11, 85-89 (1979); S. Fietz, et al., Res. Vet. Sci. 84, 347-353 (2008)). Several studies in rabbits have demonstrated significant glycosaminoglycan and collagen loss as well as overt cartilage erosions as early as 8 hours post-infection, despite treatment with anti-microbials (P. Riegels-Nielsen, et al, Acta Orthop. Scand. 60, 113-5 (1989), R. L. Smith, et al., J. Bone Joint Surg. Am. 69, 1063-8 (1987), R. L. Smith, et al., J. Orthop. Res. 1, 136-143 (1983)). Therefore, we evaluated osteochondral explants representative of different locations within the joint to explore potential chondroprotective effects of BIO-PLY treatment in infected joints. Using the same OARSI grading scheme for equine cartilage and subchondral bone (C. W. McIlwraith, et al., Osteoarthr. Cartil. 18, S93-S105 (2010)), BIO-PLY treated osteochondral explants had improved total OARSI scores compared to control horses (FIG. 26A; p<0.007). Specifically, when individual components of the grading scheme were compared between groups, numbers of chondrocyte clones (i.e., chondrones) (p<0.005) and focal cell loss (p<0.02) were decreased in BIO-PLY treated horses as compared to controls (FIGS. 26B, 27). Although the OARSI scoring method was not able to detect differences in the intensity of Safranin-O (SafO) staining for proteoglycan content within the non-mineralized cartilage (N. Schmitz, et al., Osteoarthr. Cartil. 18, S113-S116 (2010)) (FIG. 26B), when morphometrical analyses were applied to evaluate the percentage of Safranin O staining per total area of articular cartilage, BIO-PLY treated horses had a relative increased percentage area of Safranin O staining (p<0.03) (FIG. 28A) compared to control horses, indicating that BIO-PLY treatment presented inflammation-associated loss of proteoglycan content within the cartilage extracellular matrix. Interestingly, when separate regions in the joint were evaluated separately, compared to control horses, reduced depletion of Safranin O staining in BIO-PLY treated horses was localized to dorsolateral (p<0.02) (FIG. 28B), plantaromedial (p<0.005) (FIG. 28D), and plantarolateral (p<0.04) (FIG. 28E) compartments of the joint, as compared to the dorsomedial compartment of the joint where Safranin O depletion was similar in both groups of horses (FIG. 28C) (FIG. 29).

Materials and Methods Employed in Examples

Animals

Healthy horses from our closed research herd at North Carolina State University College of Veterinary Medicine (NCSU-CVM) (n=8) free of systemic and orthopedic disease and not on any medications were used for synovial fluid and blood collection. These horses are regularly evaluated by veterinarians and have complete blood counts, chemistry panels, and fecal egg counts performed every 6 months. They included 4 geldings (3 Thoroughbreds, 1 Appendix Quarter Horse) and 4 non-parous mares (all Thoroughbreds) between the ages of 6 and 19 years. The Institutional Animal Care and Use Committee of North Carolina State University (16-189-O) approved the use of horses in these studies.

Bacterial Strains and Growth Conditions

The laboratory strain of *Staphylococcus aureus*, ATCC 25923, was used to initially screen the different PRP formulations. Significant findings were then validated using clinical isolates derived from cases of equine septic arthritis collected by the University of Pennsylvania School of Veterinary Medicine New Bolton Center Clinical Microbiology Laboratory and processed in accordance with their Standard Operating Procedures. In vitro antimicrobial susceptibility testing and microbial identification was performed using the ARIS Sensititre™ system, using the equine (EQUIN1F) antimicrobial susceptibility panel for veterinary organisms. Bacteria were saved in frozen stocks on glycerol at −80° C. Blood agar plates were streaked from frozen stocks and used for in vitro experiments for a maximum of 1 month. Overnight cultures were made from the blood agar plates by taking one colony and adding to 30 mL of tryptic soy broth (TSB); these cultures were made fresh for each experiment. On the day of an experiment, 100 μL of an overnight culture was inoculated into 10 mL of fresh TSB and grown to 0.5 McFarland (~3 hours) to ensure the bacteria is in the exponential phase of growth. Concentrations of cultures were confirmed using serial plate dilutions.

Synovial Fluid Collection

Both carpi were clipped and aseptically prepped along the dorsal aspect of the joints. 3-4 mL of synovial fluid was extracted from each joint. Synovial fluid from both the right and left carpi were pooled among each individual horse. Synovial fluid that was visually cloudy or contaminated with blood was discarded. Synovial fluid was centrifuged at 1500 g for 15 minutes to remove the cellular component and passed through a 40 μM cell strainer to remove any large protein aggregates. The samples were stored at −20° C. until use in the described experiments.

Platelet-Rich Plasma (PRP) Formulations

Whole blood was collected from fasted horses via jugular venipuncture into 60 mL syringes containing 6 mL of acid citrate dextrose (ACD). Syringes were incubated at room temperature for 30 minutes to allow erythrocytes to settle. Thereafter, the layer above the erythrocytes containing the leukocytes, platelets and plasma, also called leukocyte-rich platelet-rich plasma or L-PRP, was gently transferred to a 50 mL conical tube. The L-PRP was centrifuged at 250 g for 15 minutes to generate PRP or the layer containing platelets and plasma above the leukocyte pellet. The PRP was transferred to a new 50 mL conical tube and centrifuged at 1500 g for 15 minutes to pellet the majority of platelets. The supernatant above the platelet-pellet, or platelet-poor plasma (PPP), was stored. The remaining platelet pellet was then re-suspended at varying concentrations of PPP to generate different concentrations PRP. Leukocyte, erythrocyte and platelet concentrations in each formulation were determined by staining platelets with 1 μM Calcein-AM (Invitrogen™ Molecular Probes™, ThermoFisher Scientific, Waltham, Mass., USA), incubating for 20 min, and then counting the number of fluorescent cells using a Cellometer® Auto 2000 (Nexcelom Bioscience LLC, Lawrence, Mass., USA). White blood cell (WBC) counts in PPP and PRP samples were determined using a Cellometer® Auto 2000 and ViaStain™ AOPI Staining Solution (Nexcelom Bioscience LLC, Lawrence, Mass., USA). PPP samples were defined as containing less than 10,000 platelets/μL and 10 WBC/μL. PRP samples were defined as containing greater than 350,000 platelet/μL and less than 200 WBC/μL. L-PRP contained the same amount of platelets as PRP but with greater than 10,000 WBC/μL. To generate activated PRP (A-PRP) and PRP lysate, (PRP-L), concentrated PRP was activated with 22 mM $CaCl_2$ or subjected to five freeze/thaw cycles. The majority of cell debris was removed from the A-PRP and PRP-L by centrifugation at 20,000 g for 20 minutes. Capture of charged components was performed by incubation with cation and anion exchange resins, UNOsphere S and Q resin (Bio-Rad Laboratories, Hercules, Calif., USA), respectively, in equilibrium binding mode. Further fractionation by molecular weight was performed with molecular weight cutoff filters (Amicon® Ultra 15 mL Centrifugal Filters, 50 kDa and 10 kDa, MilliporeSigma, Burlington, Mass.).

Experimental Design

Synovial fluid pooled from three horses (n=3) was infected at $1\times10^5$ CFU/mL for Staphylococcus aureus (ATCC 25923) or for each clinical isolate (Staphylococcus aureus, Streptococcus zooepidemicus, Pseudomonas aeruginosa, and Escherichia coli) and incubated for 2 hours at 37° C. in a microaerophilic chamber on a shaker at 120 rpm to allow for biofloat formation. Infected synovial fluid was treated with the aminoglycoside amikacin at 40 μg/mL and/or designated PRP treatments under the same growth conditions as the infective period for 8 hours. Amikacin was chosen as all isolates used in this study were susceptible based on microbroth dilution. Amikacin is also the most commonly used intra-articular antimicrobial in clinical equine practice (Morton A J. Vet Clin North Am—Equine Pract. 2005; 21: 627-649) and would be the antimicrobial of choice for a future in vivo study. After treatment, the infected and/or treated synovial fluid was centrifuged at 8000 g for 5 min and the supernatant was removed. The bacterial pellet was washed 3× with PBS and resuspended in 1 mL of PBS with 20 μg/mL proteinase K to disperse any aggregated bacteria. Bacterial load was measured using serial dilutions and plate counting of colony forming units. The best PRP formulation in each experiment was carried into the next experiment.

Statistical Analysis

Data was analyzed using a 1-way or 2-way ANCOVA where the covariate was the individual horse or bacterial strain with Tukey's post hoc test. Correlations were calculated using Spearman correlation coefficient. Analysis was performed using JMP Pro 11.0 software (SAS Institute Inc., Cary, N.C.). For all comparisons, $p<0.05$ was considered statistically significant. All graphs were generated using GraphPad Prism (GraphPad Software Inc., La Jolla Calif. USA).

S. aureus Growth Conditions

S. aureus (ATCC® 25923) was grown in RPMI 1640 or synovial fluid 24-well microtiter plate (Corning® Costar® Ultra-Low Attachment Multiple Well Plate, MilliporeSigma, Burlington, Mass.) to establish a planktonic phenotype or biofloat phenotype respectively. S. aureus was stained with BacLight™ Green Bacterial Stain (ThermoFisher Scientific Waltham, Mass.) prior to infection for imaging. Growth was carried out for 3 hours at 37° C. under microaerophilic conditions. Planktonic bacteria was spun down at 8000 g for 1 minute, resuspended in fresh RPMI 1640 with 10% FBS and incubated for 30 minutes to opsonize bacteria. The bacteria concentration was adjusted to $1\times10^8$ CFU/mL using a McFarland reader. Biofloat bacteria was spun down at 8000 g for 1 minute, carefully resuspended in RPMI 1640 with 10% FBS without disturbing the biofloat phenotype. Based on previous growth curve analysis the biofloat bacteria should be approximately $5\times10^6$ CFU per well. Biofloats were enzymatically digested and back plated for CFU/well to confirm bacterial numbers.

Neutrophil Isolation

Whole blood was collected via jugular venipuncture from healthy horses in our closed research herd into four 60 mL syringes containing 6 mL of acid citrate dextrose (ACD), each for a total volume of 60 mL per horse. Erythrocytes were allowed to settle for 30 minutes in the syringe and the layer above the erythrocytes containing the leukocytes, platelets, and plasma (approximately 30 mL) termed L-PRP was then transferred to a 50 mL conical tube. L-PRP was carefully layered v/v over Ficoll Paque Plus (GE Healthcare-Life Sciences, Marlborough, Mass.) and centrifuged at 695 g for 15 minutes without brake. The cell pellet containing remaining erythrocytes and leukocytes was resuspended in 1 mL of 1× DPBS. Hypotonic lysis of the remaining erythrocytes was performed by adding 9 mL of sterile deionized water and inverting slowly 10 times before adding 1 mL of 10× DPBS to restore an isotonic solution. Neutrophils were pelleted via centrifugation at 400 g for 5 minutes and resuspended in 5 mL of RPMI 1640 with 10% FBS and counted using a Cellometer® Auto 2000 and ViaStain™ AOPI Staining Solution (Nexcelom Bioscience LLC, Lawrence, Mass., USA). Neutrophils were allowed to rest for 1 hour at 37° C., 5% $CO_2$, and 90% humidity prior to being challenged with bacteria.

Neutrophil Infection

Neutrophils were added to a 24-well plate at $5\times10^5$ in RPMI 1640 with 10% FBS at 37° C. under microaerophilic conditions. Neutrophils were stimulated with $5\times10^6$ CFU *S. aureus* in a planktonic or biofloat phenotype and treated with BIO-PLY at the indicated concentrations.

Respiratory Burst and NET Quantification

Isolated neutrophils were incubated in the presence or absence of *S. aureus* (MOI 10:1) in RPMI 1640 with 10% FBS in a 24 well tissue culture plate under microaerophilic conditions at 37° C. After 2 hours, 10 μM DHR (Dihydrorhodamine 123, ThermoFisher Scientific Waltham, Mass.) was added to each well and incubated for 30 minutes prior to measuring fluorescence (excitation 485 nm, emission 528 nm) on a microtiter plate reader (Synergy™ 2, BioTek Instruments Inc., Winooski, Vt.) as an indicator of respiratory burst. After 4 hours of incubation in a microaerophilic chamber, extracellular trap (NET) formation was measured using cell impermeable DNA binding dye (SYTOX® Green Nucleic Acid Stain, ThermoFisher Scientific Waltham, Mass.) to measure NET formation. 5 μM of SYTOX® was added and incubated for 10 minutes before measuring fluorescence (excitation 485 nm, emission 528 nm) using area scan settings (15×15 measurements per well).

Neutrophil Phagocytosis and Bacterial Survival

After 1 hour of incubation, phagocytosis was measured by quantifying extracellular and intracellular bacterial load. In brief, wells were treated with DNase (50 μg/mL) and proteinaseK (20 μg/mL) for 15 minutes to release any aggregated bacteria or bacteria within NETs. Well contents were centrifuged at 400 g for 5 minutes to pellet neutrophils. Supernatants containing bacteria were serial diluted for colony counts to quantify extracellular bacteria. Neutrophils pellets were treated with 2% Triton-X 100 for 15 minutes to lyse cells. Lysate was serial diluted for colony counts to quantify intracellular bacteria. Phagocytosis was calculated as a percentage ((intracellular CFU/(intracellular CFU+extracellular CFU))×100). Bacterial survival was determined 8 hours post-infection. Wells were treated with DNase and proteinaseK in RPMI containing 2% Triton-X 100 for 15 minutes. Cellular debris was removed by centrifugation at 400 g for 5 minutes. Bacterial load was quantified by serial dilutions and plate counting. Survival was calculated as a percentage ((CFU of specific bacterial phenotype with neutrophils±BIO-PLY treatment/CFU of specific bacterial phenotype without neutrophils or BIO-PLY treatment)×100).

Neutrophil Immunofluorescence

Neutrophils were infected as described above and left untreated or treated with BIO-PLY. After 4 hours of incubation at 37° C. under microaerophilic conditions, plates were centrifuged at 500 g for 5 minutes. Each well was fixed with 4% paraformaldehyde and permeabilized with 0.5% Triton-X 100. Immunofluorescent labeling was performed with the following after blocking with 5% BSA: 1:250 rabbit anti-CitH3 and 1:500 goat anti-rabbit AF555. Immunofluorescence control wells were incubated with 1:250 rabbit IgG and 1:500 goat anti-rabbit AF555. Nuclei were stained with DAPI. Images were collected on an Olympus IX73 inverted scope with DP80 camera using appropriate fluorescent channels (Olympus Corporation, Shinjuku, Tokyo, Japan).

Synoviocyte Isolation

Synovium was harvested from the femoropatellar joints of 5 systemically healthy horses (ages 2-14 years) euthanized for reasons other than this study and free of femoropatellar joint disease. The isolated synovium was weighed and digested for 2 hours at 37° C. under constant rotation with synoviocyte media (high glucose (4.5 g/L) DMEM medium with 10% fetal bovine serum (FBS), 2 mM 1-glutamine, 1 mM sodium pyruvate, 25 mM HEPES, penicillin (100 units/mL), and streptomycin (100 μg/ml)) added at 10 mL/g tissue and containing 1.5 mg/mL Gibco® collagenase type II (ThermoFisher Scientific, Waltham, Mass., USA) (Maher et al., Equine Vet J. American Medical Association (AMA); 2014; 46: 198-202; Gregg et al., Am J Vet Res. 2006; 67: 957-962). The resulting digest was passed through a 100 μm filter and centrifuged at 800 g for 10 minutes. The cell pellet was then washed twice with fresh synoviocyte media and live synoviocyte count was determined using a Cellometer® Auto 2000 and ViaStain™ AOPI Staining Solution (Nexcelom Bioscience LLC, Lawrence, Mass., USA). Synoviocytes were frozen in aliquots of $10\times10^6$ cells/mL in liquid nitrogen until use.

Chondrocyte Isolation

Cartilage was harvested from the femoral trochlear ridges of a 2-year-old Thoroughbred gelding free of orthopedic disease and euthanized for reasons other than this study. The isolated cartilage was weighed and digested overnight (16-18 hours) at 37° C. under constant rotation with chondrocyte media (Ham's F12 medium with 10% FBS, 25 mM HEPES, ascorbic acid (50 μg/mL), α-ketoglutarate (30 μg/mL), L-glutamine (300 μg/mL), penicillin (100 units/mL), and streptomycin (100 μg/ml)) containing 0.75 mg/mL of Gibco® collagenase type II (ThermoFisher Scientific, Waltham, Mass., USA) (Nixon et al., Am J Vet Res. 1992; 53: 2364-2370; Ortved et al., Arthritis. 2016; 2016: 3484961). The resulting digest was passed through a 100 μm filter and centrifuged at 800 g for 10 minutes. The cell pellet was then washed twice with fresh chondrocyte media. Cells were resuspended in chondrocyte media and live chondrocyte count was determined using a Cellometer® Auto 2000 and ViaStain™ AOPI Staining Solution. Chondrocytes were frozen in aliquots of $10\times10^6$ cells/mL in liquid nitrogen until use.

Synoviocyte-Chondrocyte Co-Culture Infection

Synoviocytes were seeded on a polyester transwell insert of a 12-well plate (Corning® Transwell®, MilliporeSigma, Burlington, Mass.) while chondrocytes were seeded in the tissue culture treated base well. Both cells were seeded at a density of $1\times10^5$ cells/cm². After 72 hours in culture with media changes every 24 hours, *S. aureus* as biofloats or planktonic cells were introduced into the transwell insert containing the synoviocytes. Infections were carried out for 24 hours prior to treatment. Co-cultures were left untreated or treated with BIO-PLY at concentrations lower than the minimum inhibitory concentration for 24 hours. After 24 hours of treatment, synoviocytes and chondrocytes were lifted with 0.5% trypsin/EDTA solution (ThermoFisher Scientific, Waltham, Mass.) and quantified using a Cellometer® Auto 2000 and ViaStain™ AOPI Staining Solution. Viability was calculated as a percentage ((# of live cell in each well/# of cells seeded into each well)×100). Images of both synoviocytes and chondrocytes were collected on an Olympus IX73 inverted scope with DP80 camera (Olympus Corporation, Shinjuku, Tokyo, Japan) prior to RNA extraction.

RNA Extraction

Total cellular RNA was extracted from synoviocytes or chondrocytes using the RNeasy Mini Kit (Qiagen Inc., Germantown, Md., USA) according to the manufacturer's instructions. The RNA purity and quantity were evaluated using UV microspectrophotometry (NanoDrop 2000 Spectrophptometer, ThermoFisher Scientific, Waltham, Mass., USA). RNA was stored at −80° C. until cDNA construction by RT-PCR using the QuantiTect Reverse Transcription Kit (Qiagen Inc., Germantown, Md., USA) according to the manufacturer's instructions.

qPCR

Previously published equine primers were used to amplify COL1, COL2, IL-1β, MMP-3, and MMP-13 with 18S used as a housekeeping gene (Gilbertie et al., Front Vet Sci. 2018; 5). Quantitative real time RT-PCR (qPCR) was performed using the QuantiFast® SYBR® Green PCR Kit (Qiagen Inc., Germantown, Md., USA) according to the manufacturer's instructions with the QuantStudio™6 Flex System (applied biosystems®, ThermoFisher Scientific, Waltham, Mass., USA). Relative gene expression, $2^{-\Delta\Delta Ct}$, was generated using Real-Time PCR Software v1.2 (Applied Biosystems®, ThermoFisher Scientific, Waltham, Mass., USA).

Statistical Analyses

All results were assessed for normality by means of Shapiro-Wilk test. Normally distributed data was analyzed by the analysis of covariance (ANCOVA) with horse as covariate, followed by the Tukey's test for multiple comparisons. Non-normally distributed data was analyzed by the non-parametric Wilcoxon rank sum test. Statistical analyses were performed within the non-treated group across stimulations to assess the effects of stimulation and then within each stimulation group to assess for treatment effects. Analyses were performed using JMP® Pro11 (SAS Institute Inc., Cary, N.C., USA) and significance set at $p<0.05$. All graphs were generated with GraphPad Prism 7 (GraphPad, La Jolla, Calif., USA).

BIO-PLY Preparation

BIO-PLY was prepared from eight healthy horses in our closed research herd at North Carolina State University College of Veterinary Medicine (NCSU-CVM) which includes 4 geldings (3 Thoroughbreds, 1 Appendix Quarter Horse) and 4 mares (all Thoroughbreds) between the ages of 6 and 19 years. The Institutional Animal Care and Use Committee of North Carolina State University (16-189-O) approved the use of these horses for BIO-PLY preparation. Whole blood was collected from fasted horses via jugular venipuncture into 60 mL syringes containing 6 mL of acid citrate dextrose (ACD). Syringes were incubated at room temperature for 30 minutes to allow erythrocytes to settle and the layer above the erythrocytes called leukocyte-rich platelet-rich plasma or L-PRP, was centrifuged in a 50 mL conical tube at 250 g for 15 minutes to remove the leukocytes. The supernatant or PRP was transferred to a new 50 mL conical tube and centrifuged at 1500 g for 15 minutes to the platelets. The platelet-poor plasma (PPP) or supernatant above the platelet-pellet was saved and platelet pellet was re-suspended in 1 mL PPP to generate 50× PRP. Leukocyte, erythrocytes and platelet concentrations were determined as previously described (J. M. Gilbertie, et al., *J. Orthop. Res.*, jor.24584 (2020). The 50× PRP, defined as containing greater than 1,000,000 platelet/µL, less than 100 WBC/µL and <10 RBC/µL. PRP lysate, (PRP-L), was generated by five freeze/thaw cycles. The platelet debris was removed from PRP-L by centrifugation at 20,000 g for 20 minutes. Capture of anionic components was performed by incubation with loose anion exchange resin (UNOsphere Q resin, Bio-Rad Laboratories, Hercules, Calif., USA). Fractionation by molecular weight was performed with a 10 kDa molecular weight cutoff filters (Amicon® Ultra 15 mL Centrifugal Filters, 10 kDa, MilliporeSigma, Burlington, Mass.). The filtrate containing proteins and peptides <10 kDa in size was collected, aliquoted into 5 mL aliquots, and stored at −80° C. until use in this study.

Experimental Design

Skeletally mature horses (n=12; 7 mares, 4 geldings, 1 stallion; ages 2-14 years; multiple breeds) with normal physical examinations, bloodwork, and tarsocrural radiographs were randomly allocated into treatment or control groups (IACUC protocol #16-194 of NC State University). Horses were quarantined for 14 days before entrance into the study including 5-7 days of stall acclimation. On day 0, horses underwent standing sedation with intravenous detomidine (0.005-0.01 mg/kg) and butorphanol (0.005-0.01 mg/kg) in order to administer epidural analgesia and then perform the tarsocrural joint inoculation. Sacrocaudal epidural injection was performed using a 20-gauge 3.5 inch spinal needle; placement of the needle within the epidural space was confirmed using the loss of resistance technique (B. L. Fischer, et al., *Vet. Anaesth. Analg.* 36, 67-76 (2009); L. R. Goodrich, et al., *Vet. Surg.* 31, 232-9; A. M. Sysel, et al., *Vet. Surg.* 25, 511-8). Buprenorphine (0.005 mg/kg) and detomidine (0.01 mg/kg) brought up to a total volume of 20 mL with sterile saline were administered epidurally for hindlimb pain control (B. L. Fischer, et al., *Vet. Anaesth. Analg.* 36, 67-76 (2009)). *S. aureus* (ATCC 25923) at $1\times10^6$ CFU in 1 mL sterile saline was then introduced via intra-articular injection into one randomly assigned tarsocrural joint using a standard dorsomedial approach and a 21-gauge 1.5 inch needle. Prior to withdrawal of the needle from the joint, an additional 1 mL of sterile saline was injected into the joint in order to limit *S. aureus* extravasation. Twenty-four hours post-infection, horses were treated with BIO-PLY (5 mL) and 500 mg amikacin (treatment; n=6) or 500 mg of amikacin and sterile saline (5 mL) (control; n=6) daily for 7 days. All horses received systemic antimicrobials by intravenous administration of potassium penicillin (22,000 U/kg every 6 hours) in combination with gentamicin (6.6 mg/kg every 24 hours) for 10 days post-infection as well as a tapering course of phenylbutazone (4.4 mg/kg every 12 hours for days 1-3, 2.2 mg/kg every 12 hours for days 4-10 and 2.2 mg/kg every 24 hours for the duration of the study).

Clinical Observations

Horses were examined twice daily by a veterinarian for comfort and any clinical signs of systemic infection or sepsis (change in general demeanor, fever, etc.). Horses were evaluated and scored daily for pain with each category scored on a scale of 0-3 (0=most normal, 3=most abnormal): lameness, tarsocrural swelling, distal limb edema, pain to palpation of the joint, and heat at the site of infection.

Sample Collection

Starting on day 0, whole blood, plasma and serum samples were collected, and plasma/serum saved. After day 7, blood was collected weekly until the end of the study. Whole blood and serum were analyzed for changes in white blood cell populations and biochemistry values using the Clinical Pathology Laboratory at NC State University College of Veterinary Medicine. Synovial fluid was aspirated prior to treatment. Portions of the synovial fluid samples collected daily were submitted for analysis of total protein, total nucleated cell count and cellular differential. A portion of that sample was processed as a cytospin as well for further analysis of cellular changes. Aliquots of clarified synovial fluid were also saved for biomarker/biochemical analysis at the conclusion of the study. All samples were stored at −80° C. until analysis.

Diagnostic Imaging

Horses had pre-infection radiographs performed (full series: lateromedial, dorsoplantar, medial oblique and lateral oblique) followed by end-term radiographs at 21 days post infection. Ultrasonography was performed at day 0 (pre-infection), day 1 (post-infection, pre-treatment), and days 7, 14, and 21 (post-treatment). Tarsocrural joints were imaged with grayscale using the Aplio 500 system (Canon Medical Systems, Calif., USA) with a linear 12 MHz broadband transducer. Transverse and longitudinal grayscale images of the dorsomedial and plantolateral recesses of the tarsocrural joint were acquired with the limb weight bearing. Images were stored in a DICOM format and evaluated in a dedicated DICOM viewer (eFilm, Merge Healthcare, Ill., USA). All images were anonymized and randomized prior to analyses. Grayscale images were assessed by a radiologist unaware of treatment group using established criteria for infectious arthritis with each category scored on a scale of 0-3 (0=most normal, 3=most abnormal): degree of distension; degree of synovial thickening; degree of fibrinous loculation, character of synovial effusion; presence of hyperechoic foci, and degree of vascularity as visualized with power Doppler (F. Beccati, et al., *Vet. Radiol. Ultrasound* 56, 68-76 (2015)). Radiographs were evaluated using a previously published scoring system for osteoarthritis on a scale of 0-4 (0=normal, 4=severe change): boney proliferation at the joint capsule attachment; subchondral bone lysis; subchondral bone sclerosis; and osteophyte formation (D. D. Frisbie, et al., *Vet. 1* 197, 824-829 (2013)).

Necropsy

At the conclusion of the study, horses were euthanized following IACUC and AVMA guidelines and the standard of care at the NC State University College of Veterinary Medicine. The infected tarsocrural joint was aseptically prepared and dissection of the tarsocrual joint was performed aseptically from the dorsomedial aspect. The joint was evaluated for gross morphology and photographed as a reference. Synovial membrane samples were collected from four different sites within the joint (dorsomedial, dorsolateral, plantomedial, and plantolateral) for histological and microbiological analysis. Four osteochondral samples were taken from both the lateral and medial trochlea of the talus from the dorsal and plantar aspects for histological analysis.

Histology

Tissues harvested from necropsy comprising four sections of synovium and osteochondral blocks representing different anatomic locations (dorsolateral, dorsomedial, plantarolateral and plantaromedial) within each tarsocrual joint were fixed in neutral-buffered 10% formalin and routinely processed for histologic examination. Osteochondral blocks were demineralized in an aerated solution of 10% formic acid prior to trimming. Osteochondral and synovial tissues underwent routine processing for paraffin histology, sectioning at 5 µm thickness and mounting on negatively charged glass slides prior to staining. Synovial tissue specimens were stained with Hematoxylin & Eosin (H&E) and Brown and Brenn histochemical stains to assess inflammatory lesions and presence of bacteria, respectively. Routine indirect immunohistochemistry was performed to further characterize inflammatory cell infiltrates. Monoclonal antibodies using DAB detection included CD3 for T lymphocytes (DAKO; 1:100 dilution), CD20 for B lymphocytes (Thermo Scientific 1:250 dillution), CD204 for dendritic cells and macrophages (TransGenic Inc.; 1:1000 dilution), and MAC387 (S100A9, calgranulin) for myeloid leukocytes (i.e. neutrophils and monocytes) (DAKO; 1:500 dilution). Osteochondral sections were stained with H&E and Safranin O histochemical stains for evaluation of degenerative lesions and cartilage proteoglycan content, respectively. Assessment and scoring of histology specimens were performed by a blinded board-certified pathologist at the University of Pennsylvania, Department of Pathobiology, New Bolton Center. Quantitative colorimetric calculations of percentage Safranin O staining within articular cartilage from each osteochondral section was performed with MetaMorph® image analysis software (Molecular Devices Corporation, San Jose, Calif., USA). The "Trace Region" tool was used to manually select the region of interest that included the entire area ($mm^2$) of non-mineralized articular cartilage ($mm^2$) within each osteochondral section. Safranin O staining was selected by color thresholding on the red color of the stain, and measurements of percent of the thresholded area to region area within the active region were calculated by the "Show Region Statistics" function. Quantitative analyses of synovial inflammatory cell infiltrates identified by immunohistochemical stains described above were made with the opensource image analysis software QuPath (Bankhead, P. et al. (2017). *Scientific Reports.* 7: 16878 (2017). For each immunohistochemical marker listed above, two separate uniformly-sized sections (830 $mm^2$) representing synovial intimal and subintimal regions having the highest concentrations of inflammatory cells were quantified using the "positive cell detection" command. Default settings for brightfield, Hematoxylin-DAB stained images were selected and "Nucleus: DAB OD mean" was applied for the score compartment within intensity threshold parameters setting to determine cell counts and calculate percentage positive cells per area. If necessary, intensity parameters for threshold and maximum background intensity were adjusted for each image to optimize detection of DAB positive versus negative cells.

Microbiology

Historically, it has been difficult to isolate and culture bacteria from the synovial fluid of patients with infectious arthritis (J. M. Gilbertie, et al., *Vet. Microbiol.* 226 (2018), doi:10.1016/j.vetmic.2018.10.009; A. H. Taylor, et al., *Equine Vet. J.* 42, 213-218 (2010); J. Gallo, et al., *New Microbiol.* 31, 97-104 (2008)). Therefore, we have developed novel experimental methods to accurately and effectively quantify *S. aureus* grown as synovial fluid biofilms in synovial fluid as CFU per milliliter of synovial fluid. We discovered that enzymatic digestion is required in order to appropriately quantify bacterial load in infected synovial fluid (S. S. Dastgheyb, et al., *Antimicrob. Agents Chemother.* 59, 2122-2128 (2015); J. M. Gilbertie, et al., *PLoS One* 14, e0221012 (2019)). In brief, synovial fluid was treated with 20 μg/mL proteinase K (QIAGEN, Hilden, Germany) for 1 hour before centrifugation at 300 g to remove host cells. The supernatant containing synovial fluid and dispersed bacteria from synovial fluid biofilms was then serially diluted and plated for colony counts. For end-term synovium, tissue was removed aseptically at necropsy and weighed in grams. Tissue was then gently homogenized and enzymatically digested for 1 hour in media containing proteinase K and collagenase type II (ThermoFisher Scientific). Tissue homogenate was then centrifuged at 300 g for 15 min to remove debris and the supernatant containing dispersed bacteria and media was then serially diluted and plated for colony counts.

Serum and Synovial Fluid Biomarker Analysis

Venous blood samples were used to determine concentrations of D-Dimer (A. Shahi, et al., *J. Bone Jt. Surg.—Am. Vol.* 99, 1419-1427 (2017)) and serum amyloid A (E. K. Ludwig, et al., *Vet. Surg.* 45, 859-867 (2016)) using the MILLIPLEX MAP Human Cardiovascular Disease (CVD) Magnetic Bead Panel (MilliporeSigma, MA, USA) that the manufacturer predicted to have cross reactivity with equine samples (E. K. Ludwig, et al., *Vet. Surg.* 45, 859-867 (2016); C. S. Robinson, et al., *Vet. Rec.* 181, 425-425 (2017)). Concentrations of the predominate inflammatory cytokines found in synovial fluid was quantified with the MILLIPLEX MAP Equine Cytokine/Chemokine Magnetic Bead Panel (MilliporeSigma, MA, USA) (E. Curto, et al., *Vet. Immunol. Immunopathol.* 182, 43-51 (2016); J. M. Gilbertie, et al., *Front. Vet. Sci.* 5, 150 (2018)).

Statistical Analysis

All statistical analyses were performing using Stata 14.1MP, StataCorp, State College Tex., with two-sided tests of hypotheses and a p-value<0.05 as the criterion for statistical significance. Systemic and synovial fluid cell parameters and biomarkers, and bacterial load were analyzed using multivariate statistical methods. Principle component analysis was performed to examine intrinsic clusters and obvious outliers within the observations. Discriminant analysis was conducted to establish a set of biomarker concentrations based on variable selection to distinguish between groups. All scores (imaging and histology) were compared between control and treatment groups using Wilcoxon rank-sum tests. Continuous data from ultrasonography, biomechanical testing and cytokine analyses was compared between control and treatment groups using t-tests or non-parametric tests based on normality. A generalized linear mixed model was performed to compare among groups. Sex and other covariates were included as fixed effects in the model where indicated.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. An acellular cationic platelet lysate composition derived from platelet-rich plasma processed to contain ≥1,000,000 platelet/μL, ≤100 leukocytes/μL and 10 erythrocyte/μL, wherein platelets are lysed in plasma having proteolytic activity and cellular debris is removed, wherein the composition comprises cationic proteins, polypeptides and peptides <10 kDa in size, is depleted of anionic proteins, polypeptides and peptides >10 kDa in size, and comprises ≥10% plasma.

2. The composition of claim 1, wherein the composition is substantially free of non-active and immunogenic factors.

3. The composition of claim 1, comprising plasma at a range of ≥0% to ≤50%.

4. The composition of claim 1, wherein the composition is derived from multiple donors.

5. The composition of claim 1, wherein ≥1,000,000 platelet/μL are lysed in 10% plasma having proteolytic activity.

6. A method of treating a microbial infection in a subject, the method comprising administering to the subject at the site of the infection an effective amount of the composition of claim 1.

7. The method of claim 6, wherein the microbial infection is a biofilm infection.

8. The method of claim 7, wherein the biofilm infection is selected from the group consisting of infectious arthritis, a periprosthetic joint infection, and a combination thereof.

9. The method of claim 6, wherein the microbial infection is caused by a gram-positive bacterium or a gram-negative bacterium.

10. A method of treating an inflammatory condition in a subject, the method comprising administering to the subject at the site of the inflammatory condition an effective amount of the composition of claim 1.

11. A method of treating a wound in a subject, the method comprising administering to the subject at the site of the wound an effective amount of the composition of claim 1.

* * * * *